United States Patent
Croteau et al.

(10) Patent No.: US 7,402,417 B2
(45) Date of Patent: Jul. 22, 2008

(54) P450 OXYGENASES AND METHODS OF USE

(75) Inventors: Rodney B. Croteau, Pullman, WA (US); Robert Long, Moscow, ID (US); Stefan Jennewein, Alfdorf (DE)

(73) Assignee: Washington State University Research Foundation, Pullman, WA (US)

( * ) Notice: Subject to any disclaimer, the term of this patent is extended or adjusted under 35 U.S.C. 154(b) by 144 days.

(21) Appl. No.: 10/565,233

(22) PCT Filed: Jul. 21, 2004

(86) PCT No.: PCT/US2004/023656

§ 371 (c)(1),
(2), (4) Date: Jan. 18, 2006

(87) PCT Pub. No.: WO2005/010166

PCT Pub. Date: Feb. 3, 2005

(65) Prior Publication Data

US 2006/0179507 A1    Aug. 10, 2006

Related U.S. Application Data

(60) Provisional application No. 60/489,597, filed on Jul. 22, 2003.

(51) Int. Cl.
| | |
|---|---|
| *C12N 9/02* | (2006.01) |
| *C12N 1/20* | (2006.01) |
| *C12N 15/00* | (2006.01) |
| *C12P 7/66* | (2006.01) |
| *C12P 21/04* | (2006.01) |
| *C12Q 1/26* | (2006.01) |
| *C07H 21/04* | (2006.01) |
| *C12Q 1/68* | (2006.01) |
| *C12Q 1/00* | (2006.01) |

(52) U.S. Cl. .............. 435/189; 435/4; 435/6; 435/25; 435/69.1; 435/71.1; 435/132; 435/252.3; 435/320.1; 435/440; 536/23.2

(58) Field of Classification Search .............. None
See application file for complete search history.

(56) References Cited

U.S. PATENT DOCUMENTS 6,043,072 A    3/2000    Croteau et al.

(Continued)

FOREIGN PATENT DOCUMENTS

WO    WO 98/40470    9/1998

(Continued)

OTHER PUBLICATIONS

Branden et al. Introduction to Protein Structure, Garland Publishing Inc., New York, p. 247, 1991.*

(Continued)

*Primary Examiner*—Yong D Pak
(74) *Attorney, Agent, or Firm*—Paula A. DeGrandis; Klarquist Sparkman, LLP

(57) ABSTRACT

This disclosure provides the nucleic acid and protein sequences of novel P450 oxygenases that utilize, at least, taxoid substrates, including taxadiene isomers. The disclosed oxygenases, such as a taxoid 5α-hydroxylase, hydroxylate, at least, the C5 position of a taxoid. Also provided are methods of introducing oxygen at the C5 position of a taxoid and methods of producing the anti-cancer drug, paclitaxel (also known as Taxol™), and other taxoids, such as paclitaxel intermediates.

13 Claims, 7 Drawing Sheets

U.S. PATENT DOCUMENTS

| | | | |
|---|---|---|---|
| 6,787,343 B2 * | 9/2004 | Croteau et al. | 435/189 |
| 7,005,283 B2 * | 2/2006 | Croteau et al. | 435/189 |

FOREIGN PATENT DOCUMENTS

| | | | |
|---|---|---|---|
| WO | WO 01/34780 | * | 5/2001 |

OTHER PUBLICATIONS

Guo et al. Proc Natl Acad Sci USA. Jun. 22, 2004;101(25):9205-10.*

Meinkoth et al. Anal. Biochem. 138, 26 (1984).*

Cabello-Hurtado et al., "Cloning, Expression in Yeast, and Functional Characterization of CYP81B1, a Plant Cytochrome P450 That Catalyzes In-chain Hydroxylation of Fatty Acid," *J. Biol. Chem.*, 273(13):7260-7267, 1998.

Chau and Croteau, "Molecular cloning and characterization of a cytochrome P450 taxoid 2α-hydroxylase involved in Taxol biosynthesis," *Arch. Biochem. Biophys.*, 427:48-57, 2004.

Chau et al., "Taxol Biosynthesis: Molecular Cloning and Characterization of a Cytochrome P450 Taxoid 7β-Hydroxylase," *Chem. Biol.*, 11:663-672, 2004.

Chau, "Molecular Cloning and Characterization of Three Enzymes Involved in Taxol/Taxoid Biosynthesis: Taxoid 2α-Hydroxylase, Taxoid 7β-Hydroxylase, and Taxoid 5α-O-Acetyltransferase," Ph.D. Dissertation, Pullman, WA:Washington State University, May 2004.

Eisenreich et al., "Multiple Oxygenase Reactions in the Biosynthesis of Taxoids," *J. Am. Chem. Soc.*, 120:9694-9695, 1998.

Fischer et al., "Towards molecular farming in the future: using plant-cell-suspension cultures as bioreactors," *Biotechnol. Appl. Biochem.*, 30:109-112, 1999.

Hefner et al., "Cytochrome P450-catalyzed hydroxylation of taxa-4(5),11(12)-diene to taxa-4(20),11(12)-dien-5α-ol: the first oxygenation step in taxol biosynthesis," *Chem. Biol.*, 3:479-489, 1996.

Hefner et al., "Cloning and Functional Expression of a cDNA Encoding Geranylgeranyl Diphosphate Synthase from *Taxus canadensis* and Assessment of the Role of this Prenyltransferase in Cells Induced for Taxol Production," *Arch. Biochem. Biophys.*, 360(1):62-74, 1998.

Jennewein et al., "Taxol biosynthesis: Taxane 13α-hydroxylase is a cytochrome P450-dependent monooxygenase," *Proc. Natl. Acad. Sci. USA*, 98(24):13595-13600, 2001.

Jennewein et al., "Taxoid metabolism: Taxoid 14beta-hydroxylase is a cytochrome P450-dependent monooxygenase," *Arch. Biochem. Biophys.*, 413(2):262-270, 2003 (Abstract).

Jennewein et al., "Cytochrome p450 taxadiene 5alpha-hydroxylase, a mechanistically unusual monooxygenase catalyzing the first oxygenation step of taxol biosynthesis," *Chem Biol.*, 11(3):378-387, 2004.

Jennewein et al., "Random sequencing of an induced *Taxus* cell cDNA library for identification of clones involved in Taxol biosynthesis," *Proc. Natl. Acad. Sci. USA*, 101(24):9149-9154, 2004.

Nielson et al., "Cytochrome P450s in Plants," In: *Cytochrome P450: Structure, Mechanism, and Biochemistry*, Chap. 12, 3rd ed., ed. by Ortiz de Montellano, New York, NY:Kluwer Academic/Plenum Publishers, 2005.

Pauli and Kutchan., "Molecular cloning and functional heterologous expression of two alleles encoding (S)-N-methylcoclaurine 3'-hydroxylase (CYP80B1), a new methyl jasmonate-inducible cytochrome P-450-dependent mono-oxygenase P-450-dependent mono-oxygenase of benzylisoquinoline alkaloid biosynethesis," *Plant J.*, 13(6):793-801, 1998.

Schoendorf et al., "Molecular cloning of a cytochrome P450 taxane 10β-hydroxylase cDNA from *Taxus* and functional expression in yeast," *Proc. Natl. Acad. Sci. USA*, 98(4):1501-1506, 2001.

Schopfer and Ebel, "Identification of elicitor-induced cytochrome P450s of soybean (*Glycine max* L.) using differential display of mRNA," *Mol. Gen. Genet.*, 258:315-322, 1998.

Wildung et al., "A cDNA Clone for Taxadiene Synthase, the Diterpene Cyclase That Catalyzes the Committed Step of Taxol Biosynthesis," *J. Biol. Chem.*, 271(16):9201-9204, 1996.

* cited by examiner

Geranylgeranyl diphosphate (2)

Taxa-4(5),11(12)-diene (3)

Taxa-4(20),11(12)-dien-5α-ol (4)

Taxol (Paclitaxel) (1)

Figure 2

```
T13H :  ··········K············○○○VE S FV  VM  I P···  ○○○○○V P    ○○○V  L VMS  C S  ○○ IE   :  69
T10H :   SPIFLR IGT  G···   S  A  L  AP LA       YNHR  V L      P        G   L   EP KF D   :  81
T5H  :    Y··K TVA  NBVT  DC  BSF IA SA              L        L   KL   F   SPI L  A   SLE  DS   :  83

T13H :   MS     F K   I    H TVVLCG  A L R VLS   K V       S M      F  CLGG    Q   VP AA  RF         HFA    :  154
T10H :   L          YM      GH TVVLC  A   K VL     D   S  GI Q       IVA  G  D   L  TA A            TL R    :  166
T5H  :   M    LV      H  GH TVVLCG AC            I     LV Q   AQ     M   N VATR   ED IVM SA  AG F  GA   S  I     :  168

T13H :       G  ER    FI      R D ATVLF AKD       VA R   G   TEE L    ED  NL V   A S V  INI G S  H AI  AP T AD    :  239
T10H :       GH     R        RDE VKVL  A  G    RSIA T   F DVN GH    KD HL  ST LVG   VL PF GT R RF G   AS L DE    :  251
T5H  :       E  GS  I    R   I  RKDE  VVL VRE  VEN SAI      Y KQE  DR LIK  FT LVG  AL  TL L GF  RAL GG  A  NK    :  253

T13H :    TH  I   RNE PA  T  A EN   DLI  VL  T  I  R   LA PK  I LDF S  LL G SYL S     LTML I  V A  HP S  E VA    FG :  324
T10H :   LSS    IR    R DLRS  I   DDDL   VL T P D  HN  ITQG I     AMF  A STDT VA    A IER  Y S   YH  K    DE  L   :  336
T5H  :    L S  I K  KE D  Q S ATAT   DL  VL T R DD   TP NDR IL D  RS    A  YDT T  R A  I P    SS  D C Q R V  EQ  :  338

T13H :   I S  T     GEE   A  KDLN M  S  L AV QE TLR  YE    F  T  RKA  P  D   N    YT I PK  W LL T        T       KDADQ K  SR   :  409
T10H :   I G  KK  GEE  S  KDL  S KYT  G  VQE S  R Y PP  FG   F  K A TDI  DGYT I PK    RV  C9F      L R HY          RR  SR  :  421
T5H  :    S H   GEE  I   K    A  KYTW VA   T R  PP  FG T  FRKA  TDI   DGYT I P      LL T  T T   DLY N    K  M SR   :  423

T13H :   S E   KHV T  YTYL P       MP VC    E  A KMF  LL P   H  V A   OLKAI   DDH  K  L S K PL PL  V  GLP   K   YS   ········   :  485
T10H :    D       HVT  T YV P GG L  T C  G  F SI   I  L F VH  F  V NP  S YI  VDPN    VLS DPL PL  A  GFSI  KL F  RS········   :  497
T5H  :   DQ   HV  P  FL P        S V    H F   F R EI LL F VH  F VE  F SST P VD DF   I SGDPL PL  SK FS I KL F   ETIVN······   :  502
```

Figure 6A

```
T5H   MDALY--KSTVAKFNEVTQLDCSTESFSIA SAIAGILL-LLLLFRSKRH SLK     KL  57
F12   ---------MDT----FIQHESSPLLLSLT AVILGTIL-LLILSGKQYR SRK     NM  46
F21   -----MLIEMDT----FVQLESSPVLLSLT TLIL-----LFIFCSKQYR SLK     NM  46
F31   MDALSLVNSTVAKFNEVTQLQASPAILSTA TAIAGIIV--LLVITSKRR SLK     KL  58
F51   ------MDTIRASPGEVIQPEYSPLIISXA AAFLGIVI-FSIFSST-RR YVN     NL  52
F72   MDVFYPLKSTVAKFN-----ECFPAILFIV SAVAGIVLPLLLLFLRSKRR SVG     KL  55
F9    MDSFNFLRGIGADFGGFIQFQSSPAVLSLS ITTILGVL-LLWFFLHKNG SVT     NL  59
F14   MDSFIFLRSIGTK---FGQLESSPAILSLT APILAIIL-LLLFRYN-HR SVK     KL  55
F16   ---------MDA----LKQLEVSPSILFVT AVMAG----IILFFRSKRH SVK     NL  43
                                                         *    ****

T5H   I FI SPIFLRALR NSLEQ FDE VKK  L FK SLI H TVVL PAG RLI    117
F12   F LI TIALI----SDTPRK IDD VKK  L FK SLI H AVVI SSA RFL    102
F21   F LI TIALA----SQTPDK FGD MKK  L FK SLI H TIVL SSG RFL    102
F31    LFI TLBFVKALR DTLRQ VEE EGK  R FK SLL K TVIL PAG RLV    118
F51    AFI TIQFLGALQ EKPHT FDE VKK  K FK SLI D TVVL PAG RLV    112
F72    VFI SLLFLKALR NTVEQ LDE VKN  N FK SLI H TVVL PAG RLI    115
F9     FFI TIPFLRALR ETPQT FDE VKK  V FK RIV H TVVL PEG RFL    119
F14    LI TIQLLRTLR ETPQK FDD LKK  P YM SLI H TVVL PAG KLV    115
F16    LV TLQFVRSLG STPQQ IEE MSK  D FK SII H TVVL PAG RLV    103

T5H   E VQMSWPAQFMKLM ENSVATRRGED IVM S  AGFFGPGA  SYIGK NTEIQS I 177
F12   E VRMSLPNAVLKLL QDCVMGKTGVE GIV T  ARALGPQA  NYVAK SSBIEH I 162
F21   E VRMFPPNSSSKLL QDSVLGKIGEE RIV T  ARCLGPQA  NYVSK SSEIQR I 162
F31   B LHVSWSAQIARIL LNSVAWRLGD RVL V  AGFLGPSAG LYIGK SALIRN I 178
F51   D VQSAGPKSFLKLF EDSVAAKREES RIL S  GRFLGPHA  NYIGK NSEMQR F 172
F72   E VQMSWPKSSMKLM EKSITAKRGEG MII S  QGFFSPGA  KYIGQ SKTIEN I 175
F9    D VQASLPNSSEKLI KYSILSKRGEE RIL A  ARFLRPQA  GYVAK SSEIQH I 179
F14   D VEMEGPKSFMKLI EDSIVAKRGED RIL T  ARFLGAQA  NYLGR SSEIGH F 175
F16   N VQMSWPSSMMKLI EDCLGGKTGEQ RIV A  TRFLGPQA  NHFAK SSGIQR I 163

T5H   NE    KDEVNVLP VRE VFNISAI   NIYDKQEQDR HKL ETILVGSFAL IDL  237
F12   NQ    KDEVKVLP IRS VFSISTS   GINDEHQQKR HHL ETVAMGLVSI LDF  222
F21   NQ    KGEVKMLP IRS VFSIATS   GITDEQQQER HHL ETVVTGLLCI LDF  222
F31   NE    KDEVNVLS VRD VMDNSAI   NIYDKBRKQQ HEI KIILASHFGI LNI  238
F51   DD    KDEVKVLP VRG IFSIATS   NINDDRQREQ HGL DTILVGSMTI LNI  232
F72   NE    NDQVSVVA VGD VFSIDSAC   NINEKHERER FEL EIIAVGVLAV VDL  235
F9    KQ    NDEVKVLP IRT IFNIASS   GINDEHQQEQ HHL EAIVLGSLSV LDF  239
F14   NE    KDEVKVLP VRG IFSIAST   DVNDGHQQKQ HHL ETILVGSLSV LDF  235
F16   NE    KDEATVLP VKD VFSVASR   GITEEHLQEQ HNL EVILVGSFSV LNI  223

T5H   FGFHRALQGRAKLNK MLSLIKK KED QSGSATAT    VLLT R DK TPLTNDEIL  297
F12   TRFRKALYARSKLDE MSSVIER RSD RSGAASSD    VLVT K DER NSFADKEIL  282
F21   TTFRKALHARSKLDE MSSVIER RND RLGAASSD    VLLT K DER NPFADKEIL  282
F31   FLYRKALKGSLKRKK LSALLEK KDE RSRLASSN    VLLS R BER KPLSDEAVL  298
F51   TLFRKAVKARAKLDE LFALIEN RRE RSGLNSGN    SLLT K DEK NPLTDKEIL  292
F72   FAYHRALQARSKLNA LSGLIEK KMD SSGLATSN    VFLT K DR NPCSDEBIL  295
F9    TRFRKALDARSKLDE LSSLMES RRD RLGTASEN    VLLT K BER NPLTDKEIF  299
F14   TRYRKGLQARLKLDE LSSLIKR RRD RSGIASDD    VLLT R EK NSLTDQGIL  295
F16   FSYHKAIQARATLAD MTHLIEK RNE RAGTASEN    VLLT T ER NSLADKEIL  283

T5H    FSSLLHAS T TSPMALIF LLS N ECYQKVV  LE LSN EEGEEITWK  A  357
F12    FSFLLHAL T ISPLTLIF LLS S ECYENIA  LE LGN KDREEISWK  D  342
F21    FSFLLHAL X ISPLTLVF LVS N ECYENIA  LE LRN KDGEDISWA  D  342
F31    CFAMLDAS T TSQMTLII MLS N ECFEKVV  LE ASN KEGEEITMK  A  358
F51    PSVMLHAS T VSPTVLII LLA N ECYBKVV  LG LAS KEGEEVNWK  A  352
F72    FSGLLHGS T VSAMACVF LLS N ECYEKVV  LG LSN LEGDEITWK  S  355
F9     FSFMLHAS X TVSPTGLML LLF S DCYBKLV  LG VGN KEGEEISWN  A  359
F14    FSAMFHAS T VAPMALIF LLY N EYHEKVF  LE IGN KEGEEISWK  S  355
F16    FSMLLHGS S NSPLTMLI VLA H ESYEKVA  FG LST MEGEEIAWK  E  343
```

Figure 6B

```
T5H   KGTWQVADITLRMFPPVFGTFRKAITDIQYDGYTIPRGWKLLWTTYSTHPKDLYRNEPEK 417
F12   KGTWQAVDITLRMFPPVYGYIREALTDIDYDGYTIPRGWRILCSPHTTHSKEEYRDEPEE 402
P21   KGTWQAVDITLRMCPPVYGNFRKALTDIHYDGYTIPRGWRILCSPYTTHSKEEYRDDPEK 402
F31   KGTWQVLDISLRMLSPVFGTLRKTMNDINHDGYTIPRGWQVVWTTYSTHQKDIYRKQPDK 418
F51   PGTWQAIDRPLXMPKQLLECFEELSLIFSWKAIQFQRDG-QLCGXLIVNGREEFRNEPDK 411
F72   KGTWQVVRITLRLYPSIFGSFRQAITDIHYNGYIIPRGWKLLWTPYTTHPKEMYRSEPEK 415
F9    KGTCKVVDISMRMLPPVFGSYRKAXTYIHYDGYTIPRGWNIFWSPYTTHGKEEYRNEADK 419
F14   KGTWQAVDISLRMYPPVFGIFRKAITDIHYDGYTIPRGWRVLCSPYTTHLREEYRPEPEE 415
F16   KGSWQVVDITLRMYPPIFGTFRKAITDIHYNGYTIPRGWKLLWTTYSTQTKEEYRKDADQ 403
         *: :. **.: :    :    :  .:     : ..  *.   .  .: :: :* :.::

T5H   ...DQEGKHVAP...PL...G.QES.VWFS.M.I.LFV.H.VKT.SYTPV.DEK 477
F12   ...EDQGRHVAP...FI...GAL.I.AGWFARM.I.LFM.H.VKT.HFIPV.NEK 462
F21   ...EEQGRDVAP...FI...P.REFAKM.I.VFM.H.VKA.SFIPV.NEK 462
F31   ...EEEDGHLDA...FV...GER.T.PWEYA.V.I.LFL.H.VKA.GYTPT.HER 478
F51   ...EE-GKPLDE...FI...A.V.I.A.WFA.A..LFV.P.VKN.GCIII.NEK 470
F72   ...DQEGKLVAP...FL...GQES.PW.FS.M.I.LSV.H.VKT.TFTPV.AEI 475
F9    ...EE-GKYVAP...FL...GA.L.V.P.WFA.T.I.LFV.H.ITT.SYIPI.KDK 478
F14   ...EDEGRHVTP...YV...GAL.T.PW.FS.I.I.LFV.H.VKN.SYIPV.NEK 475
F16   ...EEGKHVTP...YL...GDM.V.P.PA.M..LFL.H.VKA.GLKAI.NEK 463
         * ****::  :  .**::***.*  * *  *::* * *:  :* *:.   **  :

T5H   ISGDPLPPL.SK.FSIKLPPETIVN--------- 502
F12   ISRDPLPPI.VK.FSIKPFPRS----------- 484
F21   ISTDPLPSI.VN.FSINLVPRS----------- 484
F31   ICGYPVPLV.VK.FPIKLIARS----------- 500
F51   ISGDPFPPL.TS.QLMKLIPRS----------- 492
F72   IARDSLCPL.SN.FSVKLPRSYSLHTGNQVKKI 509
F9    ISGDPFPPL.TN.FSMKLFTRS----------- 500
F14   VLSDPLPPL.AN.FSIKLFPRS----------- 497
F16   LSGKPLPPL.VN.LPIKLYSRS----------- 485
         :   ..  :*.*  ::   ..:
```

P450 OXYGENASES AND METHODS OF USE

REFERENCE TO RELATED APPLICATIONS

This application is a §371 U.S. National Stage of International Application No. PCT/US2004/023656, filed Jul. 21, 2004, which claims the benefit of U.S. Provisional Application No. 60/489,597, filed Jul. 22, 2003, each of which application is incorporated herein in its entirety.

STATEMENT OF GOVERNMENT SUPPORT

This invention was made with United States government support pursuant to grant no. CA 55254, from the National Institutes of Health. The United States government has certain rights in the invention.

FIELD OF THE DISCLOSURE

The present disclosure relates to P450 oxygenases, particularly to taxoid 5α-hydroxylases, and the nucleic acids that encode them, and to methods of using such oxygenase nucleic acids and enzymes, for example, to produce Taxol™ (commonly known as paclitaxel) and other paclitaxel intermediates.

BACKGROUND OF THE DISCLOSURE

The complex diterpenoid Taxol™ (Bristol-Myers Squibb; common name paclitaxel) (Wani et al., *J. Am. Chem. Soc.* 93:2325-2327, 1971) is a potent antimitotic agent with excellent activity against a wide range of cancers, including ovarian and breast cancer (Arbuck and Blaylock, *Taxol: Science and Applications*, CRC Press, Boca Raton, 397-415, 1995; Holmes et al., *ACS Symposium Series* 583:31-57, 1995). Paclitaxel was isolated originally from the bark of the Pacific yew (*Taxus brevifolia*). For a number of years, paclitaxel was obtained exclusively from yew bark, but low yields of this compound from the natural source coupled to the destructive nature of the harvest, prompted new methods of paclitaxel production to be developed.

Total chemical syntheses of paclitaxel have been achieved (for review, see, Kingston et al., *Prog. Chem. Org. Nat. Prod.* 84:56-225, 2002) but the yields of the drug by this method are too low to be practical. Paclitaxel currently is produced primarily by chemical semisynthesis from advanced taxane metabolites (Holton et al., *Taxol: Science and Applications*, CRC Press, Boca Raton, 97-121, 1995; Hezari and Croteau, *Planta Medica*, 63:291-295, 1997) that are isolated from the needles (a renewable resource) of various *Taxus* speciea. However, at least because of the increasing demand for this drug both for use earlier in the course of cancer intervention and for new therapeutic applications (Goldspiel, *Pharmacotherapy* 17:110S-125S, 1997), high-yield, cost-effective methods of paclitaxel production continue to be needed. Some have proposed isolating paclitaxel from alternative biological sources, such as the endophytic fungi, *Taxomyces andreanae* (Stierle et al., *J. Nat. Prod* 58:1315-1324, 1995), or from Taxus cell cultures (Ketchum et al., *Biotechnol. Bioeng.* 62:97-105, 1999). However, these methods are also too inefficient to produce sufficient quantities of the drug and have had limited commercial success.

Improving the production yield of paclitaxel from any biological system, whether intact organisms (such as, *Taxus* plants or paclitaxel-producing fungi) or cell cultures, would be facilitated by a detailed understanding of the paclitaxel biosynthetic pathway. The paclitaxel biosynthetic pathway is complex and believed to involve nearly 20 distinct steps (Floss and Mocek, *Taxol: Science and Applications*, CRC Press, Boca Raton, 191-208, 1995; and Croteau et al., *Curr. Top. Plant Physiol.* 15:94-104, 1996). However, relatively few of the enzymatic reactions and intermediates of this complicated pathway have been defined in detail.

The first committed enzyme of the paclitaxel pathway is believed to be taxadiene synthase (Koepp et al., *J. Biol. Chem.* 270:8686-8690, 1995), which cyclizes the common precursor geranylgeranyl diphosphate (Hefner et al., *Arch. Biochem. Biophys.* 360:62-74, 1998) to taxadiene (FIG. 1). The cyclized intermediate (i.e., taxa-4(5),11(12)-diene) subsequently undergoes modification involving at least eight oxygenation steps, a formal dehydrogenation, an epoxide rearrangement to an oxetane, and several acylations (Floss and Mocek, *Taxol: Science and Applications*, CRC Press, Boca Raton, 191-208, 1995; and Croteau et al., *Curr. Top. Plant Physiol.* 15:94-104, 1996). Taxadiene synthase has been isolated from *T. brevifolia* and characterized (Hezari et al., *Arch. Biochem. Biophys.* 322:437444, 1995), the mechanism of action defined (Lin et al., *Biochemistry* 35:2968-2977, 1996), and the corresponding cDNA clone isolated and expressed (Wildung and Croteau, *J. Biol. Chem.* 271:9201-9204, 1996).

The second specific step of paclitaxel biosynthesis is believed to be an oxygenation (hydroxylation) reaction that introduces a hydroxyl group to position 5 of taxa-4(5),11(12)-diene to produce taxa-4(20),11(12)-dien-5α-ol. Using a crude *Taxus* microsome preparation, Hefner et al. (*Methods Enzymol.* 272:243-250, 1996) demonstrated a microsomal activity that catalyzed the stereospecific hydroxylation of taxa-4(5),11(12)-diene to taxa-4(20),11(12)-dien-5α-ol (with double-bond rearrangement) (Hefner et al., *Chem. Biol.*, 3:479-489, 1996). This microsomal activity was attributed to one or more cytochrome P450 oxygenases (Hefner et al., *Chemistry and Biology* 3:479-489, 1996). Cytochrome P450 oxygenases are enzymes that have a unique sulfur atom ligated to the heme iron and that, when reduced, form carbon monoxide (CO) complexes. When complexed to carbon monoxide, cytochrome P450 proteins display a major absorption peak (Soret band) near 450 nm.

*Taxus* microsomal preparations were further shown to catalyze the hydroxylation of taxadiene or taxadien-5α-ol to the level of a pentaol (Hefner et al., *Methods Enzymol.* 272:243-250, 1996; Lovy Wheeler et al., *Arch. Biochem. Biophys.*, 390:265-278, 2001). These results suggested that the paclitaxel biosynthetic pathway included at least five distinct cytochrome P450 taxoid oxygenases in the early parts of the pathway (Hezari et al., *Planta Med.* 63:291-295, 1997). Later steps of the paclitaxel biosynthetic pathway are thought to include at least three additional oxygenation steps (C1 and C7 hydroxylations and an epoxidation at C4-C20). These steps also are believed to be catalyzed by cytochrome P450 enzymes, but these reactions reside too far down the pathway to observe in microsomes by current experimental methods (Croteau et al., *Curr. Topics Plant Physiol.* 15:94-104, 1995; Hezari et al., *Planta Med.* 63:291-295, 1997 Lovy Wheeler et al., *Arch. Biochem. Biophys.*, 390:265-278, 2001). Since *Taxus* (yew) plants and cells do not appear to accumulate taxoid metabolites bearing fewer than six oxygen atoms (e.g., hexaol or epoxypentaol) (Kingston et al., *Prog. Chem. Org. Nat. Prod.* 61:1-206, 1993), such intermediates must be rapidly transformed down the pathway, indicating that the oxygenations (hydroxylations) are relatively slow pathway steps.

*Taxus* microsome preparations contain hundreds of different proteins, including an estimated 30 to 50 similar cytochrome P450 oxygenases (Hefner et al., *Methods Enzymol.* 272:243-250, 1996). Biochemical purification of cytochrome P450 enzymes from Taxus microsomes (Hefner et al., *Methods Enzymol.* 272:243-250, 1996) is not practical, at least, because the numerous P450 cytochrome oxygenases present in this cell fraction have very similar physical properties (Mihaliak et al., *Methods Plant Biochem.* 9:261-279, 1993). With no useful biochemical means to distinguish among the many microsomal P450 oxygenases, it is not feasible to sufficiently purify any one enzyme to obtain even short peptide sequences. As a result, other methods are needed to isolate and characterize these important enzymes at the molecular level.

Differential display reverse transcription PCR (DD-RT PCR) has been used to isolate methyl jasmonate-induced nucleic acids encoding taxoid oxygenases of the paclitaxel biosynthetic pathway (see, for example, PCT Pub. No. WO01/34780). Several of the encoded oxygenase enzymes have been expressed and functionally characterized (PCT Pub. No. WO01/34780; Schoendorf et al., *Proc. Natl. Acad. Sci. USA,* 98:1501-1506, 2001; Jennewein et al., *Proc. Natl. Acad. Sci. USA,* 98:13595-13600, 2001; Jennewein et al., Arch Biochem. Biophys., 413:262-270, 2003). However, transcripts encoding taxoid oxygenases that are not, or only weakly, induced are likely to be missed by the DD-RT PCR technique.

Paclitaxel is an important drug that is not efficiently produced using current methods. Genetic engineering and recombinant technologies offer ways to increase paclitaxel and taxoid yields. To capitalize on these technologies, there is a continuing need to identify and isolate the genes encoding the enzymes of the paclitaxel biosynthetic pathway, including, for example, the numerous oxygenase enzymes, and for methods of using such genes and enzymes to produce paclitaxel and its intermediates.

SUMMARY OF THE DISCLOSURE

This disclosure provides a novel P450 oxygenase, which is capable of incorporating oxygen (for example, a hydroxyl group or epoxide ring) into a substrate, such as a taxoid. In some examples, the disclosed oxygenase incorporates oxygen at the C5 position of a taxoid, wherein the disclosed oxygenase is referred to as a taxoid 5-hydroxylase. In more specific examples, the oxygen is incorporated in the alpha configuration at C5 of a taxoid, wherein the disclosed oxygenase is referred to as a taxoid 5α-hydroxylase. In some examples, a taxoid substrate for a disclosed oxygenase includes a taxadiene, such as taxa-4(5),11(12)-diene and taxa-4(20),11(12)-diene.

Encompassed within this disclosure are the protein and nucleic acid sequences of the disclosed P450 oxygenase. Also provided are nucleotide and amino acid sequence variants, oligonucleotides and protein fragments. This disclosure demonstrates that the disclosed enzymes catalyze the oxygenation of taxoids, for example, at the C5 position. Evidence provided herein also demonstrates the relaxed substrate specificity of the disclosed oxygenases. It is also disclosed that a nucleic acid encoding a disclosed oxygenase, such as a 5α-hydroxylase cDNA, can be operatively linked to a promoter and cells can be transfected with the recombinant polynucleotide.

Also provided herein are methods for using a disclosed oxygenase, such as a taxoid 5α-hydroxylase. Such methods include, without limitation, methods of using a taxoid 5α-hydroxylase to hydroxylate a taxoid substrate or to produce (or increase the yield of) paclitaxel or paclitaxel intermediates. Examples of these methods include introducing a taxoid 5α-hydroxylase recombinant polynucleotide into a cell, such as a *Taxus* cell, or contacting a taxoid with a 5α-hydroxylase polypeptide or functional fragment thereof. Also disclosed are taxoid 5α-hydroxylase-specific binding agents.

The foregoing and other features and advantages will become more apparent from the following detailed description of several embodiments, which proceeds with reference to the accompanying figures.

BRIEF DESCRIPTION OF THE FIGURES

FIG. 2 shows an alignment of the deduced amino acid sequences of selected taxoid hydroxylases. The sequences of taxoid 10β-hydroxylase (T10H; SEQ ID NO: 16), taxoid 13α-hydroxylase (T13H; SEQ ID NO: 18) and the clone S1 taxadiene 5α-hydroxylase (TSH; SEQ ID NO: 2) are compared. Black boxes indicate identical residues for the three sequences; grey boxes indicate identical residues for two of the three.

FIGS. 6A and 6B collectively show an alignment of the deduced amino acid sequences of selected taxoid oxygenases. The sequence of clone S1 taxoid 5α-hydroxylase (T5H; SEQ ID NO: 2) is compared to the sequences of eight other taxoid oxygenases isolated from *Taxus cuspidata*. Each of the illustrated oxygenases is known to have a positive CO difference spectrum and to oxidize intermediates in the paclitaxel biosynthetic pathway or derivatives thereof (see, e.g., PCT Pub. No. WO01/23586, Table 2). Oxygenase sequences other than T5H are designated as in PCT Pub. No. WO01/23586 (herein, "F clones"). F31 is a taxoid 7β-hydroxylase (SEQ ID NO: 8); F72 is a taxoid 14β-hydroxylase (SEQ ID NO: 12), F14 is a taxoid 10β-hydroxylase (SEQ ID NO: 16), and F16 is a taxoid 13α-hydroxylase (SEQ ID NO: 18). F14 and F16 correspond to T10H and T13H, respectively, in FIG. 2. The other illustrated F clones are F12 (SEQ ID NO: 4), F21 (SEQ ID NO: 6), F51 (SEQ ID NO: 10), and F9 (SEQ ID NO: 14). Shaded amino acid residues are identical among all sequences; ":" indicates conservative substitutions among the amino acid residues at that position

BRIEF DESCRIPTION OF THE SEQUENCE LISTING

Figure 1:
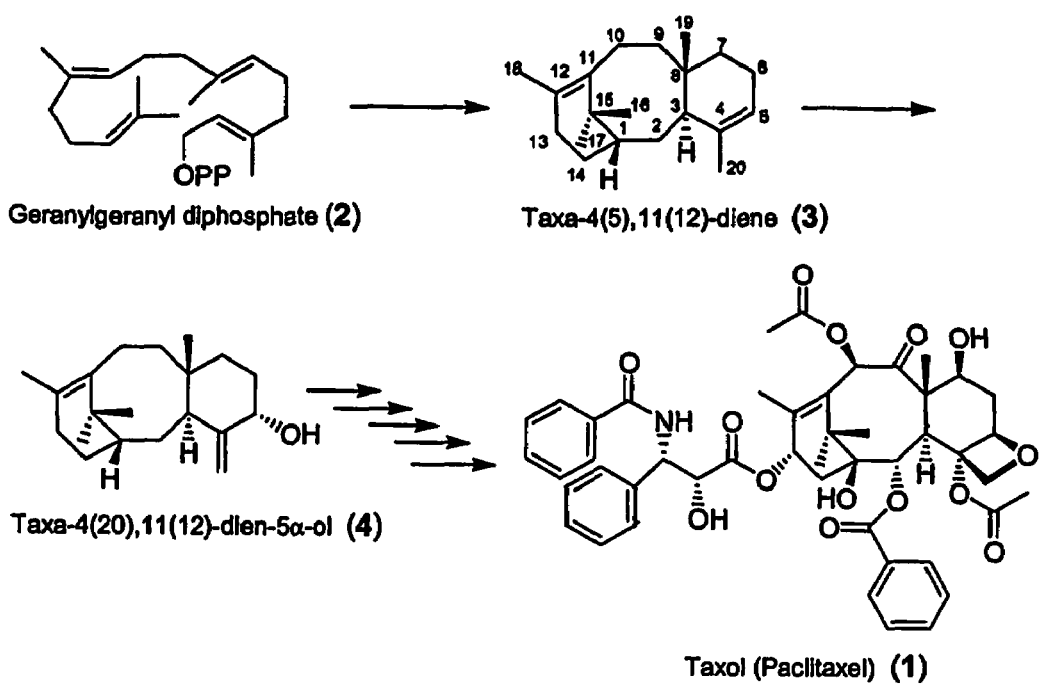
FIG. 1 shows an outline of the early steps of paclitaxel biosynthesis. Paclitaxel (1) formation involves the cyclization of geranylgeranyl diphosphate (2) to taxa-4(5),11(12)-diene (3) and cytochrome P450-mediated hydroxylation to taxa-4(20),11(12)-dien-5α-ol (4). The multiple arrows between taxa-4(20),11(12)-dien-5α-ol (4) and paclitaxel (1) are represented of numerous additional enzymatic steps in the paclitaxel biosynthetic pathway.

The nucleic and amino acid sequences listed in the accompanying sequence listing are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand. In the accompanying sequence listing:

SEQ ID NO: 1 shows a nucleic acid sequence encoding a taxoid 5α-hydroxylase (GenBank Accession No. AY289209) and its corresponding amino acid sequence.

SEQ ID NO: 2 shows an amino acid sequence of a taxoid 5α-hydroxylase (GenBank Accession No. AAQ56240.1), which is encoded by the nucleic acid sequence in SEQ ID NO: 1.

SEQ ID NO: 3 shows the nucleic acid sequence of Clone F12 described in PCT Pub. No. WO01/23586.

SEQ ID NO: 4 shows the taxoid oxygenase amino acid sequence encoded by Clone F12.

SEQ ID NO: 5 shows the nucleic acid sequence of Clone F21 described in PCT Pub. No. WO01/23586.

SEQ ID NO: 6 shows the taxoid oxygenase amino acid sequence encoded by Clone F21.

SEQ ID NO: 7 shows a nucleic acid sequence encoding a taxoid 7β-hydroxylase (see, also, clone F31 as described in PCT Pub. No. WO01/23586) (GenBank Accession No. AY307951).

SEQ ID NO: 8 shows a taxoid 7β-hydroxylase amino acid sequence (GenBank Accession No. AAQ7553), which is encoded by the nucleic acid sequence in SEQ ID NO: 7.

SEQ ID NO: 9 shows the nucleic acid sequence of Clone F51 described in PCT Pub. No. WO01/23586.

SEQ ID NO: 10 shows the taxoid oxygenase amino acid sequence encoded by Clone F51.

SEQ ID NO: 11 shows a nucleic acid sequence encoding a taxoid 14β-hydroxylase (see, also, clone F72 as described in PCT Pub. No. WO01/23586) (GenBank Accession No. AY188177; Jennewein et al., *Arch. Biochem. Biophys.*, 413 (2):262-270, 2003).

SEQ ID NO: 12 shows a taxoid 14β-hydroxylase amino acid sequence (GenBank Accession No. AAO66199), which is encoded by the nucleic acid sequence in SEQ ID NO: 11.

SEQ ID NO: 13 shows the nucleic acid sequence of Clone F9 described in PCT Pub. No. WO01/23586.

SEQ ID NO: 14 shows the taxoid oxygenase amino acid sequence encoded by Clone F9.

SEQ ID NO: 15 shows a nucleic acid sequence encoding a taxoid 10β-hydroxylase (see, also, clone F14 as described in PCT Pub. No. WO01/23586) (GenBank Accession No. AY563635; Jennewein et al, *Proc. Nat. Acad. Sci. USA*, 101 (24):9149-9154, 2004).

SEQ ID NO: 16 shows a taxoid 10 β-hydroxylase amino acid sequence (GenBank Accession No. AAT47183) encoded by the nucleic acid sequence in SEQ ID NO: 15.

SEQ ID NO: 17 shows a nucleic acid sequence encoding a taxoid 13α-hydroxylase (see, also, clone F16 as described in PCT Pub. No. WO01/23586) (GenBank Accession No. AY056019; Jennewein et al., *Proc. Nat. Acad. Sci. USA*, 98(24):13595-13600, 2001).

SEQ ID NO: 18 shows a taxoid 13α-hydroxylase amino acid sequence (GenBank Accession No. AAL23619) encoded by the nucleic acid sequence in SEQ ID NO: 17.

SEQ ID NO: 19 shows a nucleic acid sequence encoding a taxadiene synthase (GenBank Accession No. U48796; Wildung and Croteau, *J. Biol. Chem.*, 271(16):9201-9204, 1996) and its corresponding amino acid sequence.

SEQ ID NO: 20 shows the amino acid sequence of a taxadiene synthase (GenBank Accession No. AAC49310), which is encoded by the nucleic acid sequence in SEQ ID NO: 19.

SEQ ID NO: 21 shows a nucleic acid sequence encoding a taxadienol acetyl transferase (also called, TAT or TAX1) (GenBank Accession No. AF190130; Walker et al., *Arch. Biochem. Biophys.*, 374(2):371-380, 2000) and its corresponding amino acid sequence.

SEQ ID NO: 22 shows the amino acid sequence of a taxadienol acetyl transferase (GenBank Accession No. AAF34254), which is encoded by the nucleic acid sequence in SEQ ID NO: 21.

SEQ ID NO: 23 shows a nucleic acid sequence encoding a 2-debenzoyl-7,13-diacetylbaccatin III-2-O-benzoyl transferase (also called, TAX2) (GenBank Accession No. AF297618; Walker and Croteau, *Proc. Natl. Acad. Sci. USA*, 97(25):13591-13596, 2000)) and its corresponding amino acid sequence.

SEQ ID NO: 24 shows the amino acid sequence of a 2-debenzoyl-7,13-diacetylbaccatin III-2-O-benzoyl transferase (GenBank Accession No. AAG38049), which is encoded by the nucleic acid sequence in SEQ ID NO: 23.

SEQ ID NOs: 25-29 show primers directed to the commonly occurring P450 oxygenase PERF motif and its variant forms.

SEQ ID NOs: 30-31 show primers directed to the conserved P450 oxygenase heme-binding region.

SEQ ID NOs: 32-33 show primers suitable for amplifying a nucleic acid sequence encoding a taxoid 5α-hydroxylase.

SEQ ID NO: 34 shows a nucleic acid sequence encoding a 10-deacetylbaccatin III-10-O-acetyl transferase (also called, TAX6 or DBAT) (GenBank Accession No. AF193765; e.g., Walker and Croteau, *Proc. Natl. Acad. Sci. USA*, 97(2):583-587, 2000) and its corresponding amino acid sequence.

SEQ ID NO: 35 shows the amino acid sequence of a 10-deacetylbaccatin III-10-O-acetyl transferase, which is encoded by the nucleic acid sequence in SEQ ID NO: 33.

SEQ ID NO: 36 shows a nucleic acid sequence encoding a taxoid 13-phenylpropanoyltransferase (also called, TAX7) (GenBank Accession No. AY082804, Walker et al., *Proc. Natl. Acad. Sci. USA*, 99(20):12715-12720, 2002) and its corresponding amino acid sequence.

SEQ ID NO: 37 shows the amino acid sequence of a taxoid 13-phenylpropanoyltransferase, which is encoded by the nucleic acid sequence in SEQ ID NO: 35.

SEQ ID NO: 38 shows a nucleic acid sequence encoding a taxoid 3'-N-debenzoyltaxol N-benzoyltransferase (also called, TAX10 or DBNTBT) (GenBank Accession No. AF466397; Walker et al., *Proc. Natl. Acad. Sci. USA*, 99(14): 9166-9171, 2002) and its corresponding amino acid sequence.

SEQ ID NO: 39 shows the amino acid sequence of a taxoid 3'-N-debenzoyltaxol N-benzoyltransferase, which is encoded by the nucleic acid sequence in SEQ ID NO: 37.

SEQ ID NO: 40 shows a nucleic acid sequence encoding a taxoid 2α-hydroxylase ((GenBank Accession No.

AY518383; Chau and Croteau, *Arch. Biochem. Biophys.,* 427 (1):48-57, 2004) and its corresponding amino acid sequence.

SEQ ID NO: 41 shows the amino acid sequence of a taxoid 2α-hydroxylase, which is encoded by the nucleic acid sequence in SEQ ID NO: 39.

DETAILED DESCRIPTION

I. Abbreviations and Terms
CO carbon monoxide
ELISA enzyme-linked immunosorbent assay
GC-MS gas chromatography-mass spectroscopy
HPLC high performance liquid chromatography
HSQC heteronuclear single quantum coherence
KIE kinetic isotope effect
kDa kilodaltons
MW molecular weight
NMR nuclear magnetic resonance spectroscopy
ORF open reading frame
RACE rapid analysis of cDNA ends
ROESY rotational nuclear overhauser effect spectroscopy
TLC thin layer chromatography
TOCSY total correlated spectroscopy Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments disclosed herein, the following explanations of specific terms are provided:

Amplification: When used in reference to nucleic acids, techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744, 311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target: oligonucleotide complex. Binding between a target and an oligonucleotide can be detected by any procedure known to one of ordinary skill in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

cDNA (complementary DNA): A piece of DNA lacking internal, non-coding segments (introns) and transcriptional regulatory sequences. cDNA can also contain untranslated regions (UTRs) that can be responsible for translational control in the corresponding RNA molecule. cDNA can be synthesized in the laboratory by reverse transcription from messenger RNA extracted from cells.

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single strandedness is required by the text herein, DNA molecules, though written to depict only a single strand, encompass both strands of a double-stranded DNA molecule. Thus, a reference to the nucleic acid molecule that encodes a specific protein, or a fragment thereof encompasses both the sense strand and its reverse complement Thus, for instance, it is appropriate to generate probes or primers from the reverse complement sequence of the disclosed nucleic acid molecules.

Encode: A polynucleotide is said to "encode" a polypeptide if, in its native state or when manipulated by methods well known to those of ordinary skill in the art, it can be transcribed and/or translated to produce the mRNA for and/or the polypeptide or a fragment thereof. The anti-sense strand is the complement of such a nucleic acid, and the encoding sequence can be deduced therefrom.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein (see, Stryer, *Biochemistry*, Third Edition, W.H. Freeman and Company, New York, N.Y., p. 769, 1988). Third, part of a polypeptide chain can be deleted without impairing or eliminating all of its functions. Fourth, insertions or additions can be made in the polypeptide chain for example, adding epitope tags, without impairing or eliminating its functions (Ausubel et al., *Current Protocols in Molecular Biology*, Greene Publ. Assoc. and Wiley-Intersciences, 1997; Jennewein et al., *Arch. Biochem. Biophys.*, 413:262-270, 2003). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by ordinarily skilled artisans. A variety of methods for labeling polypeptides and labels, which are useful for such purposes are well known in the art, and include radioactive isotopes such as $^{32}P$, ligands that bind to or are bound by labeled specific binding partners (e.g. antibodies), fluorophores, chemiluminescent agents, enzymes, and antiligands. Functional fragments and variants can be of varying length; For example, some functional fragments have at least 75, 100, 200, 300 or 400 amino acid residues.

A functional fragment or variant of a disclosed P450 oxygenase, such as a taxoid 5α-hydroxylase, is defined herein as a polypeptide capable of oxidizing (for example, hydroxylating or epoxidizing) a taxoid. In specific examples, a functional fragment or variant oxidizes a taxoid at the C5 position. It includes any polypeptide of about 100 or more amino acid residues in length, which is capable of having taxoid oxygenase activity.

Heterologous: A type of sequence that is not normally (i.e. in the wild-type sequence) found adjacent to a second sequence. In one embodiment, the sequence is from a different genetic source, such as a virus or organism, than the second sequence.

Host cell: Any cell that is capable of being transformed with a recombinant nucleic acid sequence. For example, bacterial cells, fungal cells, plant cells (such as, *Taxus* cells), insect cells, avian cells, mammalian cells, and amphibian cells. A host cell can be isolated or it can exist as a part of a transgenic organism (such as, microorganism (or lower life form) or a macroorganism). In specific examples, a host cell can be a primary cell or a cell line. A primary cell is a cell that is taken directly from a living organism, such as a plant (e.g., a plant from the genus *Taxus*), which is not immortalized. The term "cell line" refers to a cell that is able to replicate in culture. Some cell lines (often called immortal cells) are capable of an essentially unlimited number of cell divisions. A primary cell may become a cell line upon continuous culture. In some instances, an immortal cell can arise spontaneously, for example, as a result of uncharacterized alterations in the cell genome. In other case, a cell, such as a primary cell, can be made immortal using techniques commonly known in the art, including transfection with SV40 T-antigen or telomerase reverse transcriptase (TERT) (for review, e.g., Hahn, *Mol. Cells*, 13(3):351-361, 2002).

Hybridization: Oligonucleotides and other nucleic acids hybridize by hydrogen bonding, which includes Watson-Crick, Hoogsteen or reversed Hoogsteen hydrogen bonding, between complementary bases. Generally, nucleic acid consists of nitrogenous bases that are either pyrmidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between to distinct nucleic acid sequences or two distinct regions of the same nucleic acid sequence.

Specifically hybridizable and specifically complementary are terms that indicate a sufficient degree of complementarity such that stable and specific binding occurs between a first nucleic acid (such as, an oligonucleotide) and a DNA or RNA target. The first nucleic acid (such as, an oligonucleotide) need not be 100% complementary to its target sequence to be specifically hybridizable. A first nucleic acid (such as, an oligonucleotide) is specifically hybridizable when there is a sufficient degree of complementarity to avoid non-specific binding of the first nucleic acid (such as, an oligonucleotide) to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

The following are exemplary sets of hybridization conditions and are not meant to be limiting.

| Very High Stringency (detects sequences that share 90% sequence identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share 80% sequence identity or greater) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share greater than 50% sequence identity) | |
| Hybridization: | 6x SSC at RT to 55° C. for 16-20 hours |
| Wash at least twice: | 2x-3x SSC at RT to 55° C. for 20-30 minutes each. |

Isolated: A biological component (such as a nucleic acid molecule, protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame (ORF): A series of nucleotide triplets (codons) coding for amino acids without any internal termination codons. These sequences are usually translatable into a peptide.

Organism: Any individual living thing, whether unicellular or multi-cellular and including all members of Archaea, Bacteria, and Eukaryota taxonomical classifications, such as plants, yeast, bacteria, fungi, and insects.

Ortholog: Two nucleic acid or amino acid sequences are orthologs of each other if they share a common ancestral sequence and diverged when a species carrying that ancestral sequence split into two species. Orthologous sequences are also homologous sequences.

Oxidation: The process of incorporating oxygen into a molecule, such a substrate of a P450 oxygenase. Specific types of oxidation include, for example, epoxidation and hydroxylation. "Epoxidation" involves a chemical reaction in which an oxygen atom is joined to an olefinically unsaturated molecule to form a cyclic, three-membered ether. An "olefin" is a hydrocarbon containing a carbon-carbon double bond. "Hydroxylation" is a chemical reaction in which a hydroxyl (—OH) group is incorporated into a molecule.

Oxygenase activity: Enzymes exhibiting oxygenase activity are capable of directly incorporating oxygen into a substrate molecule. The process of incorporating oxygen into a substrate molecule is called "oxidation." Oxygenases can be either dioxygenases, in which case the oxygenase incorporates two oxygen atoms into the substrate; or, monooxygenases, in which only one oxygen atom is incorporated into the primary substrate, for example, to form a hydroxyl or epoxide group. Monooxygenases also may be referred to as "hydroxylases." Taxoid oxygenases are a subset of oxygenases that specifically utilize taxoids as substrates. Taxoid oxygenases can utilize, for example, taxoid substrates having a methylene group at any position, including for example, taxoids having a 5-methylene group (such as, taxoid 5α-hydroxylases), taxoids having a 2-methylene group (such as, taxoid 2α-hydroxylases), taxoids having a 7-methylene group (such as, taxoid 7β-hydroxylases), taxoids having a 10-methylene group (such as, taxoid 10β-hydroxylasess), taxoids having a 13-methylene group (such as, taxoid 13α-hydroxylases), or taxoids having a 14-methylene group (such as, taxoid 14β-hydroxylases).

Oxygenases: Oxygenases are enzymes that display oxygenase activity as describe above. A particular oxygenase may recognize one or more substrates. An oxygenase that will recognize more than one substrate is said to have "relaxed substrate specificity." Different oxygenases may recognize the same substrate and have "shared substrate specificity." Oxygenase enzyme activity assays may utilize one or more different substrates depending on the specificity(ies) of the particular oxygenase enzyme. One of ordinary skill in the art will appreciate that a variety of general oxygenase activity assays, including, for instance, the spectrophotometry-based assay described herein, are available, and that direct assays can be used to test oxygenase catalysis directed towards different substrates.

Polypeptide: A polymer in which the monomers are amino acid residues joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recomnbinantly or synthetically produced. The term(s) "isolated polypeptide" (or isolated protein) as used herein refers to a polypeptide that is substantially free of other proteins, lipids, carbohydrates or other materials with which it is naturally associated. In one embodiment, the polypeptide is at least 50%, for example at least 70%, at least 80%, at least 90%, or at least 95%, free of other proteins, lipids, carbohydrates or other materials with which it is naturally associated.

Probes and primers: Nucleic acid probes and primers can be readily prepared based on the nucleic acid molecules provided in this disclosure. A probe comprises a detectable isolated nucleic acid. In some instances, a probe is directly attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In: *Molecular Cloning: A Laboratory Manual*, Cold Spring Harbor Laboratory Press, Now York, 1989) and Ausubel et al. (In: *Current Protocols in Molecular Biology*, Greene Publ. Assoc. and Wiley-Intersciences, 1992).

Primers are short nucleic acid molecules, such as DNA oligonucleotides 10 nucleotides or more in length Longer DNA oligonucleotides can be about 15, 17, 20, or 23 nucleotides or more in length Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, Cold Spring Harbor Laboratory Press, New York, 1989), Ausubel et al. (In *Current Protocols in Molecular Biology*, Greene Publ. Assoc. and Wiley-Intersciences, 1998), and Innis et al. (PCR Protocols, *A Guide to Methods and Applications,* Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length Thus, in order to obtain greater specificity, probes and primers can be selected that comprise at least 17, 20, 23, 25, 30, 35, 40, 45, 50 or more consecutive nucleotides.

Protein: A biological molecule expressed by a gene and comprised of amino acids.

Purified: The term purified does not require absolute purity; rather, it is intended as a relative term. Thus, for example, a purified protein preparation is one in which the protein referred to is more pure than the protein in its natural environment within a cell. For example, a preparation of an enzyme can be considered as purified if the enzyme content in the preparation represents at least 50%, at least 60%, at least 70%, at least 80%, at least 90%, or at least 95% of the total protein content of the preparation.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

Sequence Identity: The similarity between two nucleic acid sequences or between two amino acid sequences is expressed in terms of the level of sequence identity shared between the sequences. Sequence identity is typically expressed in terms of percentage identity, the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.,* 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blasts, blast; tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

An alternative indication that two nucleic acid molecules are closely related is that the two molecules hybridize to each other under stringent conditions (see "Hybridization" above).

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target. For example, a taxoid 5α-hydroxylase protein-specific binding agent binds substantially only the taxoid 5α-hydroxylase protein.

Antibodies are exemplar specific binding agents. Antibodies can be produced using standard procedures described in a number of texts, including Harlow and Lane (*Antibodies, A Laboratory Manual,* Cold Spring Harbor Laboratory Press, New York, 1988). Shorter fragments of antibodies can also serve as specific binding agents, including, for instance, Fabs, Fvs, and single-chain Fvs (SCFvs). Antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody (SCA), a genetically engineered molecule containing the variable region of the light chain, the variable region of the heavy chain, linked by a suitable polypeptide linker as a genetically fused single chain molecule. Methods of making these fragments are routine.

Substrate: A molecule that binds to an enzyme, such as a P450 oxygenase, and undergoes a chemical change, such as oxidation, during the ensuing enzymatic reaction. Exemplar substrates for the disclosed P450 oxygenases are described throughout this specification. An "exogenous substrate" is a substrate that is added to a particular type of cell.

Taxadien-5-ol transacylase activity: Capable of transferring an acyl group (such as an acetyl group) from an acyl carrier (such as acetyl-CoA) to a taxoid substrate comprising a hydroxyl group at C5 (such as taxadien-5α-ol); for additional details, see, e.g., U.S. Pat. No. 6,287,835.

Taxadien-2-ol transacylase activity: Capable of transferring an acyl group (such as a benzoyl group) from an acyl carrier (such as benzoyl CoA) to a taxoid substrate comprising a hydroxyl group at C2 (such as 2-debenzoyl-7,13-diacetylbaccatin III); for additional details, see, e.g., PCT Pub. No. WO 01/23586.

Taxadiene synthase activity: Capable of cyclizing geranylgeranyl diphosphate to produce taxadiene, as described in detail, e.g., in U.S. Pat. Nos. 6,610,527; 6,114,160; and 5,994,114.

Taxoid: A chemical based on the taxan ring structure (pentamethyl[9.3.1.0]$^{3,8}$tricyclopentadecane). The core taxane ring structure is described, for example, in Kingston et al., *Progress In the Chemistry of Organic Natural Products*, Springer-Verlag, 1993, and has the chemical structure:

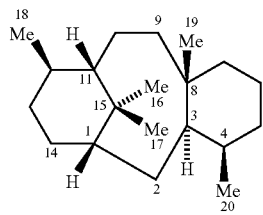

Exemplary taxoids are described throughout the specification and also include, without limitation, taxadiene, taxadienyl acetate (including, e.g., taxa-5α-yl acetate), taxa-4(5),11 (12)-diene, taxa-4(20),11(12)-diene, taxadien-5α-ol, taxa-4 (20),11(12)-dien-5,13-diol, 5α-acetoxy-10β,14,β-dihydroxy taxadiene, 2-debenzoyl taxane, 10-deacetyl baccatin III, baccatin III, 3'-N-debenzoyltaxol, taxa-4(20),11(12)-dien-5α, 9α,10β-triol, taxa-4(20),11(12)-dien-2α,5α-diol (and diacetate ester); taxa-4(20),11(12)-dien-5α,9α,10β,13β-tetraol and corresponding tetraacetate (taxusin tetraol and taxusin, respectively), taxa-4(20),11(12)-dien-5α,9α-diol (and monoacetate and diacetate); taxa-4(20),11(12)-dien-5α,10β-diol (and monoacetate and diacetate); taxa-4(20),11(12)-dien-5α,9α,10β-triol (and acetate esters); and a taxoid having a 5-methylene group (R—CH$_2$—R).

Transfected: A process by which a nucleic acid molecule is introduced into cell, for instance by molecular biology techniques, resulting in a transfected (or transformed) cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Vector: A nucleic acid molecule as introduced into a host cell, thereby producing a transfected (or transformed) host cell. A vector can include nucleic acid sequences that permit it to replicate in a host cell, such as an origin of replication. A vector can also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means "including A or B," or "including A and B." It is further to be understood that all base sizes or amino acid sizes, and all molecular weight or molecular mass values, given for nucleic acids or polypeptides are approximate, and are provided for description Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Description of Several Specific Embodiments

Disclosed herein are isolated proteins having taxoid oxygenase activity (such as, taxadiene hydroxylation activity) and the nucleic acid sequences encoding such proteins (including, for example, SEQ ID NO: 1). In some embodiments, the protein comprising an amino acid sequence having at least 80% or at least 95% sequence identity to SEQ ID NO: 2 or comprises the sequence in SEQ ID NO: 2.

Isolated nucleic acid molecules that (i) hybridize under high (or very high) stringency conditions with a nucleic acid probe comprising at least 600 base pairs of SEQ ID NO: 1 and (ii) encode a protein having taxoid oxygenase activity are also contemplated by this disclosure; as are the taxoid oxygenase proteins encoded by such nucleic acid molecules.

Further provide herein are isolated nucleic acid molecules having a sequence at least 80% identical to the nucleic acid sequence in SEQ ID NO: 1 and encoding a protein having taxoid oxygenase activity, such as taxoid 5α-hydroxylase activity. A protein encoded by such a nucleic acid molecule is also disclosed.

Also provided are recombinant nucleic acid molecules, which include a promoter sequence operably linked to a nucleic acid molecule encoding a disclosed taxoid oxygenase protein (such as, a taxoid 5α-hydroxylase). In certain examples, a cell (such as, a plant cell (including a *Taxus* cell or cell line), an insect cell, a bacterium, or a yeast cell) or a non-human transgenic organism (such as a plant, including a plant from the genus *Taxus*) are transformed with the recombinant nucleic acid. In particular examples, the cell is an isolated cell, such as a cell line.

This disclosure includes method of identifying a nucleic acid sequence that encodes a taxoid oxygenase, which involve (i) hybridizing a probe to a nucleic acid sequence under high (or very high) stringency conditions, wherein the probe comprises at least 600 contiguous nucleotides of SEQ ID NO: 1; and (ii) determining that a protein encoded by the nucleic acid sequence is capable of oxidizing a taxoid substrate. A protein capable of oxidizing a taxoid substrate is thereby identified as a taxoid oxygenase. In some examples, oxidizing the taxoid substrate involves hydroxylating the taxoid substrate.

Methods of hydroxylating a substrate are also disclosed. Such methods involve contacting a substrate with at least one oxygenase having an amino acid sequence at least 95% identical to SEQ ID NO: 2 (or having the sequence of SEQ ID NO: 2); and allowing the oxygenase to oxidize the substrate. In some methods, oxidation of the substrate involves hydroxylation of the substrate. In other methods, the substrate is a taxoid (such as, paclitaxel, a paclitaxel intermediate, a taxadiene, taxa-4(5),11(12)-diene or taxa-4(20),11(12)-diene). In some cases, hydroxylation occurs at position C5 of the taxoid. In specific embodiments, the oxygenase is expressed in an isolated cell or in a transgenic plant, bacterium, insect, fungus or yeast, and the hydroxylation of the substrate occurs in vivo. In other embodiments, the substrate is an exogenous substrate, which is fed to the isolated cell, transgenic plant, transgenic bacterium, transgenic insect, transgenic fungus or transgenic yeast.

Also provided herein are methods for increasing paclitaxel yield in a cell (such as a *Taxus* cell, including, for example, a *Taxus* cell line), which involve introducing any of the taxoid oxygenase-encoding recombinant nucleic acid molecules disclosed herein into a paclitaxel-producing cell, wherein the production of paclitaxel is increased in the cell following the introduction of the recombinant nucleic acid molecule. In a particular example, the recombinant nucleic acid molecule that is introduced into the cell includes the nucleic acid sequence in SEQ ID NO: 1. In some examples of this method, the amount of paclitaxel produced by the cell is at least four fold higher following introduction of the recombinant nucleic acid molecule into the cell. In more specific examples, methods for increasing paclitaxel yield in a cell (such as a *Taxus* cell, including, for example, a *Taxus* cell line) further involve introducing additional nucleic acid molecules into the cell. Exemplar additional nucleic acid molecules include those: (i) encoding a protein having taxadiene synthase activity (e.g., nucleic acid molecules having at least 90% sequence identity to SEQ ID NO: 19 (or its protein-coding region), and encoding a protein having taxadiene synthase activity); (ii) encoding a protein having taxadien-5-ol transacylase activity (e.g., nucleic acid molecules having at least 90% sequence identity to SEQ ID NO: 21 (or its protein-coding region), and encoding a protein having taxadien-5-ol transacylase activity); (iii) encoding a protein having taxadien-2-ol transacylase activity (e.g., nucleic acid molecules having at least 90% sequence identity to SEQ ID NO: 23 (or its protein-coding region), and encoding a protein having taxadien-2-ol transacylase activity); (iv) encoding a protein having taxoid oxygenase activity (such as, taxoid 7β-hydroxylase activity, taxoid 14β-hydroxylase activity, taxoid 10β-hydroxylase activity, taxoid 13α-hydroxylase activity, or taxoid 2α-hydroxylase activity) (e.g., nucleic acid molecules having at least 90% sequence identity to any one of the sequences (or their respective protein-coding regions) set forth in SEQ ID NOs: 3, 5, 7, 9, 11, 13, 15, 17, or 40 and encoding a protein having taxoid oxygenase activity (such as, taxoid 7β-hydroxylase activity (e.g., SEQ ID NO: 7), taxoid 14β-hydroxylase activity (e.g., SEQ ID NO: 11), taxoid 10β-hydroxylase activity (e.g., SEQ ID NO: 15), or taxoid 13α-hydroxylase activity (e.g., SEQ ID NO: 17), or taxoid 2α-hydroxylase activity (e.g., SEQ ID NO: 40)); or (v) combinations of (i), (ii), (iii), or (iv). In specific methods, the additional nucleic acid molecules comprise one or more of the nucleic acid sequences set forth in SEQ ID NOs: 3, 5, 7, 9, 11, 13, 15, 17, 19, 21, 23 or 40 (or any combination thereof).

This disclosure also provides antibodies or antibody fragments that bind any of the taxoid oxygenase proteins, such as a taxoid 5α-hydroxylase, described herein. In specific examples the antibody is a monoclonal antibody. In other examples, the antibody fragment is a Fab, F(ab)2, or Fv fragment, or a combination thereof.

III. Taxoid 5α-hydroxylase Nucleic Acids and Proteins

This disclosure provides P450 oxygenases, such as a taxoid 5α-hydroxylase, and variants thereof, and nucleic acid molecules encoding these proteins, including cDNA sequences.

A nucleic acid molecule encoding a taxoid 5α-hydroxylase and the corresponding deduced amino acid sequence of taxoid 5α-hydroxylase, are shown in SEQ ID NOs: 1 and 2, respectively. The nucleic acid molecule encodes a protein of 502 amino acids in length (SEQ ID NO: 2).

With the provision herein of the sequence of the taxoid 5α-hydroxylase protein (SEQ ID NO: 2) and cDNA (SEQ ID NO: 1), in vitro nucleic acid amplification (such as polymerase chain reaction (PCR)) may be utilized as a simple method for producing taxoid 5α-hydroxylase encoding sequences. The following provides representative techniques for preparing cDNA in this manner.

RNA (such as mRNA or total RNA) is extracted from cells by any one of a variety of methods well known to those of ordinary skill in the art. Sambrook et al. (In *Molecular Cloning: A Laboratory Manual*, Cold Spring Harbor Laboratory Press, New York, 1989) and Ausubel et al. (In *Current Protocols in Molecular Biology*, Greene Publ. Assoc. and Wiley-Intersciences, 1992) provide descriptions of methods for RNA isolation. Taxoid 5α-hydroxylase is expressed, at least, in cells from plants of the genus *Taxus*. Thus, in some examples, RNA may be extracted from *Taxus* cells. The extracted RNA is then used, for example, as a template for performing reverse transcription (RT)-PCR amplification of cDNA. Representative methods and conditions for RT-PCR are described in Kawasali et al., (In *PCR Protocols, A Guide to Methods and Applications*, Innis et al. (eds.), 21-27, Academic Press, Inc., San Diego, Calif., 1990).

The selection of amplification primers will be made according to the portion(s) of the cDNA that is to be amplified. In one embodiment, primers may be chosen to amplify a segment of a cDNA or, in another embodiment, the entire cDNA molecule. Variations in amplification conditions may be required to accommodate primers and amplicons of differing lengths and composition; such considerations are well known in the art and are discussed for instance in Innis et al. (*PCR Protocols, A Guide to Methods and Applications*, Academic Press, Inc., San Diego, Calif., 1990). By way of example, the coding portion of the taxoid 5α-hydroxylase cDNA molecule (approximately 1509 base pairs) may be amplified using the following combination of primers:

```
                                          (SEQ ID NO: 32)
    5'-ATGGACGCCCTGTATAAGAG-3' (forward)

(SEQ ID NO: 33)
    5'-TCAATTGACTATGGTCTCGG-3' (reverse)
```

These primers are illustrative only; one skilled in the art will appreciate that many different primers may be derived from the provided cDNA sequence in order to amplify particular regions of taxoid 5α-hydroxylase cDNA, as well as the complete sequence of the taxoid 5α-hydroxylase cDNA.

Re-sequencing of PCR products obtained by amplification procedures optionally can be performed to facilitate confirmation of the amplified sequence and provide information about natural variation of this sequence in different populations or species. Oligonucleotides derived from the provided taxoid 5α-hydroxylase sequences may be used in such sequencing methods.

Orthologs of the disclosed P450 oxygenases, such as a taxoid 5α-hydroxylase, are likely present in a number of other members of the *Taxus* genus (such as, *T. brevifolia*, *T. canadensis*, *T. baccata*, *T. globosa*, *T. floridana*, *T. wallichiana*, *T. media* and *T. chinensis*) and other taxoid-producing organisms (such as, *Taxomyces andreanae*). With the provision of the disclosed oxygenase nucleic acid sequence, the cloning by standard methods of cDNAs and genes that encode oxygenase orthologs in these other organisms is now enabled. Orthologs of the disclosed oxygenase genes have oxygenase biological activity, including for example oxidation (such as, hydroxylation or epoxidation) of the C5 position of a taxoid. Orthologs will generally share at least 65% sequence identity with the disclosed P450 oxygenase cDNA (for example, SEQ ID NO: 1). Sequence identity will generally be greater in *Taxus* species more closely related to *Taxus cuspidata*. In specific embodiments, orthologous oxygenase (for example, taxoid 5α-hydroxylase) molecules may share at least 70%, at least 75%, at least 80% at least 85%, at least 90%, at least 91%, at least 93%, at least 95%, or at least 98% sequence identity with the disclosed *Taxus cuspidata* nucleotide or amino acid sequences.

Both conventional hybridization and PCR amplification procedures may be utilized to clone sequences encoding oxygenase orthologs. Common to both of these techniques is the hybridization of probes or primers that are derived from the oxygenase nucleic acid sequences. Furthermore, the hybridization may occur in the context of Northern blots, Southern blots, or PCR.

Direct PCR amplification may be performed on cDNA or genomic libraries prepared from the plant species in question, or RT-PCR may be performed using mRNA extracted from the plant cells using standard methods. PCR primers will comprise at least 10 consecutive nucleotides of the oxygenase sequences. One of skill in the art will appreciate that sequence differences between the oxygenase nucleic acid sequence and the target nucleic acid to be amplified may result in lower amplification efficiencies. To compensate for this, longer PCR primers or lower annealing temperatures may be used during the amplification cycle. Whenever lower annealing temperatures are used, sequential rounds of amplification using nested primer pairs may be necessary to enhance specificity.

For conventional hybridization techniques the hybridization probe is preferably conjugated with a detectable label such as a radioactive label, and the probe is preferably at least 10 nucleotides in length. As is well known in the art, increasing the length of hybridization probes tends to give enhanced specificity. The labeled probe derived from the oxygenase nucleic acid sequence may be hybridized to a plant cDNA or genomic library and the hybridization signal detected using methods known in the art. The hybridizing colony or plaque (depending on the type of library used) is purified and the cloned sequence contained in that colony or plaque isolated and characterized.

Orthologs of the oxygenases alternatively may be obtained by immunoscreening of an expression library. With the provision herein of the disclosed oxygenase nucleic acid sequences, the enzymes may be expressed and purified in a heterologous expression system (e.g., *E. coli*) and used to raise antibodies (monoclonal or polyclonal) specific for oxygenases. Antibodies also may be raised against synthetic peptides derived from the oxygenase amino acid sequence presented herein. Methods of raising antibodies are well known in the art and are described generally in Harlow and Lane, *Antibodies, A Laboratory Manual*, Cold Springs Harbor, 1988. Such antibodies can be used to screen an expression cDNA library produced from a plant This screening will identify the oxygenase ortholog. The selected cDNAs can be confirmed by sequencing and enzyme activity assays.

Oligonucleotides derived from the taxoid 5α-hydroxylase cDNA sequence (e.g., SEQ ID NO: 1), or fragments of this cDNA, are encompassed within the scope of the present disclosure. Such oligonucleotides may be used, for example, as probes or primers. In one embodiment, oligonucleotides may comprise a sequence of at least 10 consecutive nucleotides of the taxoid 5α-hydroxylase nucleic acid sequence. If these oligonucleotides are used with an in vitro amplification procedure (such as PCR), lengthening the oligonucleotides may enhance amplification specificity. Thus, in other embodiments, oligonucleotide primers comprising at least 15, 20, 25, 30, 35, 40, 45, 50, or more consecutive nucleotides of these sequences may be used.

One of ordinary skill in the art will appreciate that the specificity of a particular probe or primer increases with its length. Thus, for example, a primer comprising 30 consecutive nucleotides of a *Taxus cuspidata* taxoid 5α-hydroxylase encoding nucleotide will anneal to a target sequence, such as a taxoid 5α-hydroxylase gene homolog present in a cDNA library from another *Taxus* species (or other paclitaxel-producing species), with a higher specificity than a corresponding primer of only 15 nucleotides. Thus, in order to obtain greater specificity, probes and primers can be selected that comprise at least 17, 20, 23, 25, 30, 35, 40, 45, 50 or more consecutive nucleotides of taxoid 5α-hydroxylase nucleotide sequences. In particular examples, probes or primers can be at least 100, 250, 500, or 600 consecutive nucleic acids of a disclosed 5α-hydroxylase sequence.

Oligonucleotides (such as, primers or probes) may be obtained from any region of a disclosed 5α-hydroxylase nucleic acid sequence. By way of example, the taxoid 5α-hydroxylase cDNA, ORF and gene sequences may be apportioned into about halves, thirds or quarters based on sequence length, and the isolated nucleic acid molecules (e.g., oligonucleotides) may be derived from the first or second halves of the molecules, from any of the three thirds, or from any of the four quarters. The cDNA also could be divided into smaller regions, e.g. about eighths, sixteenths, twentieths, fiftieths and so forth, with similar effect. The taxoid 5α-hydroxylase cDNA shown in SEQ ID NO: 1 can be used to illustrate this. The taxoid 5α-hydroxylase cDNA is 1509 nucleotides in length and so in one specific embodiment, it may be hypothetically divided into about halves (nucleotides 40-794 and 795-1548), in another specific embodiment, in about thirds (nucleotides 40-543, 544-1047, and 1048-1548) or, in yet another specific embodiment, in about quarters (nucleotides 40-417, 418-795, 795-1173 and 1174-1548). Alternatively, it may be divided into regions that encode for conserved domains such as, for example, the commonly occurring PERF motif and the region surrounding the invariant, heme-binding cysteine residue (von Wachenfeldt and Johnson, "Structures of eukaryotic cytochrome P450 enzymes," In: Cytochrome P450: Structure, Mechanism, and Biochemistry, 2nd Ed., P. R Ortiz de Montollano, ed., New York: Plenum, pp. 183-223, 1995).

IV. Cloning of the Taxoid 5α-Hydroxylase Gene

The taxoid 5α-hydroxylase cDNA sequence and fragments described above do not contain introns, upstream transcriptional promoter or regulatory regions or downstream transcriptional regulatory regions of the taxoid 5α-hydroxylase gene. The taxoid 5α-hydroxylase gene may be isolated by routine procedures. For instance, the taxoid 5α-hydroxylase gene may be isolated by homology screening using the cDNA sequence and the BLAST program. Direct sequencing, using the "long-distance sequence method," of one or more BAC or PAC clones that contain the taxoid 5α-hydroxylase sequence can be employed.

Using the information disclosed herein, the regulatory elements flanking the taxoid 5α-hydroxylase gene can be identified and characterized. These regulatory elements may be characterized by standard techniques. In one embodiment, deletion analysis is performed wherein successive nucleotides of a putative regulatory region are removed and the effect of the deletions is studied by transient expression analysis. In another embodiment, the effect of the deletions is studied by long-term expression analysis. The identification and characterization of regulatory elements flanking the genomic taxoid 5α-hydroxylase gene may be made by functional analysis (deletion analyses, etc.) in *Taxus* cells by either transient or long-term expression analyses.

It will be apparent to one skilled in the art that either the genomic clone or the cDNA or sequences derived from these clones may be utilized in applications, including but not limited to, studies of the expression of the taxoid 5α-hydroxylase gene, studies of the function of the taxoid 5α-hydroxylase protein, and the generation of antibodies to the taxoid 5α-hydroxylase protein. Descriptions of applications describing the use of taxoid 5α-hydroxylase cDNA, or fragments thereof, are therefore intended to comprehend the use of the genomic taxoid 5α-hydroxylase gene.

It will also be apparent to one of ordinary skill in the art that taxoid 5α-hydroxylase genes may now be cloned from other *Taxus* species by standard cloning methods. In one embodiment, such orthologous taxoid 5α-hydroxylase genes will share at least 65% sequence identity with the taxoid 5α-hydroxylase nucleic acid disclosed herein; and in other embodiments, more closely related orthologous sequences will share at least 70%, at least 75%, at least 80%, at least 90%, at least 95%, or at least 98% sequence identity with this sequence.

V. Taxoid 5α-Hydroxylase Sequence Variants

With the provision of taxoid 5α-hydroxylase protein and corresponding nucleic acid sequences herein, the creation of variants of these sequences is now enabled. Variant oxygenases include proteins that differ in amino acid sequence from the oxygenase sequences disclosed, but that retain oxygenase biological activity.

In one embodiment, variant taxoid 5α-hydroxylase proteins include proteins that differ in amino acid sequence from the taxoid 5α-hydroxylase sequences disclosed but that share at least 70% amino acid sequence identity with the provided taxoid 5α-hydroxylase protein. In other embodiments, other variants will share at least 75%, at least 80%, at least 85%, at least 90%, at least 95%, or at least 98% amino acid sequence identity. Manipulation of the disclosed taxoid 5α-hydroxylase nucleotide sequence using standard procedures, including in one specific, non-limiting, embodiment, site-directed mutagenesis or in another specific, non-limiting, embodiment, PCR, can be used to produce such variants. The simplest modifications involve the substitution of one or more amino acids for amino acids having similar biochemical properties. These so-called conservative substitutions are likely to have minimal impact on the activity of the resultant protein. The following table shows exemplar conservative amino acid substitutions:

| Original Residue | Conservative Substitutions |
|---|---|
| ala | Ser |
| arg | Lys |
| asn | Gln; his |
| asp | Glu |
| cys | Ser |
| gln | Asn |
| glu | Asp |
| gly | Pro |
| his | Asn; gln |
| ile | Leu; val |
| leu | ile; val |
| lys | Arg; gln; glu |
| met | Leu; ile |
| phe | Met; leu; tyr |
| ser | Thr |
| thr | Ser |
| trp | Tyr |
| tyr | Trp; phe |
| val | ile; leu |

In some embodiments, the functional identity of a 5α-hydroxylase variant can be maintained if amino acid substitutions are introduced in regions outside of the conserved domains of the protein, where amino acid substitutions are less likely to affect protein function. FIG. 6 shows the alignment of nine taxoid oxygenase amino acid sequences, including the 5α-hydroxylase sequence disclosed herein. Shaded amino acid residues are conserved among all of the illustrated sequences. In certain embodiments, oxygenase variants share the highly conserved (i.e., shaded and marked by asterisk) amino acid residues shown in FIG. 6. FIG. 6 also demonstrates conservative amino acid variations (i.e., marked by ":") among these taxoid oxygenase sequences. In other embodiments, oxygenase variants having conservative substitutions (as described in the foregoing table) at the amino acid positions indicated by ":" in FIG. 6 are contemplated herein. Amino acid residues that are not highly conserved (i.e., shaded or marked by asterisk in FIG. 6) or conservative variations (i.e., marked by ":" in FIG. 6) are least likely to be functionally relevant and, therefore, may tolerate less conservative amino acid substitutions with little to no effect on the function of the resultant variant. In other embodiments, 5α-hydroxylase protein variants may be designed (as discussed above) based on highly conserved and conservative amino acids shown in the alignment of three of the foregoing nine amino acid sequences, as shown in FIG. 2.

In another embodiment, more substantial changes in 5α-hydroxylase function or other protein features may be obtained by selecting amino acid substitutions that are less conservative than conservative substitutions. In one specific, non-limiting, embodiment, such changes include changing residues that differ more significantly in their effect on maintaining polypeptide backbone structure (e.g., sheet or helical conformation) near the substitution, charge or hydrophobicity of the molecule at the target site, or bulk of a specific side chain. The following specific, non-limiting, examples are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant taxoid 5α-hydroxylase encoding sequences may be produced by standard DNA mutagenesis techniques. In one specific, non-limiting, embodiment, M13 primer mutagenesis is performed. Details of these techniques are provided in Sambrook et al. (In *Molecular Cloning: A Laboratory Manual*, Cold Spring Harbor Laboratory Press, New York, 1989), Ch 15. By the use of such techniques, variants may be created that differ in minor ways from the taxoid 5α-hydroxylase sequences disclosed. In one embodiment, DNA molecules and nucleotide sequences that are derivatives of those specifically disclosed herein, and which differ from those disclosed by the deletion, addition, or substitution of nucleotides while still encoding a protein that has at least 65% sequence identity with the taxoid 5α-hydroxylase encoding sequence disclosed (SEQ ID NO: 1), are comprehended by this disclosure. In other embodiments, more closely related nucleic acid molecules that share at least 70%, at least 75%, at least 80%, at least 85%, at least 90%, at least 95%, or at least 98% nucleotide sequence identity with the disclosed taxoid 5α-hydroxylase sequences are comprehended by this disclosure. Alternatively, related nucleic acid molecules can have no more than 3, 5, 10, 20, 50, 75, or 100 nucleic acid changes compared to SEQ ID NO: 1. In one embodiment, such variants may differ from the disclosed sequences by alteration of the coding region to fit the codon usage bias of the particular organism into which the molecule is to be introduced.

In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed taxoid 5α-hydroxylase protein sequences. For example, because of the degeneracy of the genetic code, four nucleotide codon triplets—(GCT, GCG, GCC and GCA)—code for alanine. The coding sequence of any specific alanine residue within the taxoid 5α-hydroxylase protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques, as described above, or by synthesis of DNA sequences. Thus, this disclosure also encompasses nucleic acid sequences that encode a taxoid 5α-hydroxylase protein, but which vary from the disclosed nucleic acid sequences by virtue of the degeneracy of the genetic code.

In one embodiment, variants of the taxoid 5α-hydroxylase protein may also be defined in terms of their sequence identity with the prototype taxoid 5α-hydroxylase protein. As described above, taxoid 5α-hydroxylase proteins share at least 70%, at least 75%, at least 80%, at least 85%, at least 90%, at least 95%, or at least 98% amino acid sequence identity with the taxoid 5α-hydroxylase protein (SEQ ID NO: 2). Alternatively, variants of the taxoid 5α-hydroxylase protein can have no more than 3, 5, 10, 15, 20, 25, 30, 40, or 50 amino acid changes compared to SEQ ID NO: 2. Nucleic acid sequences that encode such proteins/fragments readily may be determined simply by applying the genetic code to the amino acid sequence of a taxoid 5α-hydroxylase protein or fragment, and such nucleic acid molecules may readily be produced by assembling oligonucleotides corresponding to portions of the sequence.

Nucleic acid molecules that are derived from the taxoid 5α-hydroxylase cDNA nucleic acid sequences include molecules that hybridize under low stringency, high stringency, or very high stringency conditions to the disclosed prototypical taxoid 5α-hydroxylase nucleic acid molecules, and fragments thereof.

Taxoid 5α-hydroxylase nucleic acid encoding molecules (including the cDNA shown in SEQ ID NO: 1, and nucleic acids comprising this sequence), and orthologs and homologs of these sequences, may be incorporated into transformation or expression vectors.

VI. Introduction of Oxygenases into Plants or Plant Cells

A nucleic acid molecule (such as a cDNA or gene) encoding taxoid 5α-hydroxylase may be incorporated into any organism (intact plant, animal, microbe, etc.) or cell or tissue culture system (such as, suspension cell culture, callus cell culture, or immobilized cell culture) for any useful purpose known to those of ordinary skill in the art, including, without limitation, (i) production of taxoid 5α-hydroxylase, (ii) synthesis of 5α-hydroxylated taxoids, such as taxadien-5α-ol; (iii) enhancement of the rate of production and/or the absolute amount of one or more taxoids derived from 5α-hydroxylated taxoids, such as taxadien-5α-ol; (iv) enhancement of the rate of production and/or the absolute amount of paclitaxel or paclitaxel intermediates or derivatives.

In one embodiment, a disclosed 5α-hydroxylase nucleic acid molecule is introduced into a plant or plant cell, for example, a gymnosperm species (such as, a *Taxus* species). Gymnosperms are a useful expression system, at least, because of (i) compatible codon usage for high translational efficiency; (ii) recognition of the encoded preprotein by the plastid import system; (iii) high fidelity in proteolytic processing by the plastids to the mature enzyme form; and (iv) efficient protein-protein interaction with upstream and downstream enzymes of the paclitaxel pathway for most efficient channeling of metabolites.

After a cDNA (or gene) encoding a protein involved in the determination of a particular plant characteristic has been isolated, standard techniques may be used to express the cDNA in transgenic plants in order to modify the particular plant characteristic. The basic approach is to clone the cDNA into an expression vector, such that the cDNA is operably linked to control sequences (e.g., a promoter), which direct expression of the cDNA in plant cells. The transformation vector is introduced into plant cells by any of various techniques (e.g., electroporation), and progeny plants containing the introduced cDNA are selected. Preferably all or part of the transformation vector stably integrates into the genome of the plant cell. That part of the transformation vector that integrates into the plant cell and that contains the introduced cDNA and associated sequences for controlling expression (the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifest as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples that serve to illustrate the knowledge in this field of technology include, without limitation, U.S. Pat. No. 4,459,355 ("Method for Transforming Plant Cells"); U.S. Pat. No. 5,571,706 ("Plant Virus Resistance Gene and Methods"); U.S. Pat. No. 5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in *Brassica* Species"); U.S. Pat. No. 5,268,526 ("Overexpression of Phytochrome in Transgenic Plants"); U.S. Pat. No. 5,262,316 ("Genetically Transformed Pepper Plants and Methods for their Production"); U.S. Pat. No. 5,569,831 ("Transgenic Tomato Plants with Altered Polygalacturonase Isoforms"); U.S. Pat. No. 5,932,782 ("Plant Transformation Method Using *Agrobacterium* Species Adhered to Microprojectiles"); and U.S. Pat. No. 6,759,573 ("Method to Enhance *Agrobacterium*-Mediated Transformation of Plants").

These examples include descriptions of transformation vector selection, transformation techniques, and the construction of constructs designed to over-express the introduced cDNA. In light of the foregoing and the provision herein of the oxygenase amino acid sequences and nucleic acid sequences, it is thus apparent that one of ordinary skill in the art will be able to introduce the cDNAs, or homologous or derivative forms of these molecules, into plants in order to produce plants having enhanced oxygenase activity. Furthermore, the expression of one or more oxygenases in plants may give rise to plants having increased production of paclitaxel and related compounds.

A. Vector Construction, Choice of Promoters

A number of recombinant vectors suitable for stable transfection of plant cells or for the establishment of transgenic plants have been described, including those described in Weissbach and Weissbach, *Methods for Plant Molecular Biology*, Academic Press, 1989; and Gelvin et al., *Plant and Molecular Biology Manual*, Kluwer Academic Publishers, 1990. Typically, plant transformation vectors include one or more cloned plant genes (or cDNAs) under the transcriptional control of 5'-and 3'-regulatory sequences and a dominant selectable marker. Such plant transformation vectors typically also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and/or a polyadenylation signal.

Examples of constitutive plant promoters that may be useful for expressing the cDNA include: the cauliflower mosaic virus (CaMV) 35S promoter, which confers constitutive, high-level expression in most plant tissues (see, e.g., Odel et al., *Nature*, 313:810, 1985; Dekeyser et al., *Plant Cell*, 2:591, 1990; Terada and Shimamoto, *Mol. Gen. Genet.*, 220:389, 1990; Benfey and Chua, *Science*, 250:959-966, 1990); the nopaline synthase promoter (An et al., *Plant Physiol.*, 88:547, 1988); and the octopine synthase promoter (Fromm et al., *Plant Cell*, 1:977, 1989). *Agrobacterium*-mediated transformation of *Taxus* species has been accomplished, and the resulting callus cultures have been shown to produce paclitaxel (Han et al., *Plant Science*, 95:187-196, 1994). Therefore, it is likely that incorporation of one or more of the described oxygenases under the influence of a strong promoter (like CaMV promoter) would increase production yields of paclitaxel and related taxoids in such transformed cells.

A variety of plant gene promoters that are regulated in response to environmental, hormonal, chemical, and/or developmental signals also can be used for expression of the cDNA in plant cells, including promoters regulated by: (a) heat (Callis et al., *Plant Physiol.*, 88:965, 1988; Ainley, et al., *Plant Mol. Biol.*, 22:13-23, 1993; and Gilmartin et al., *Plant Cell*, 4:839-949, 1992); (b) light (e.g., the pea rbcS-3A promoter, Kuhlemeier et al., *Plant Cell*, 1:471, 1989, and the maize rbcS promoter, Schaffner and Sheen, *Plant Cell*, 3:997, 1991); (c) hormones, such as abscisic acid (Marcotte et al., *Plant Cell*, 1:969, 1989); (d) wounding (e.g., wuni, Siebertz et al., *Plant Cell*, 1:961, 1989); and (e) chemicals such as methyl jasmonate or salicylic acid (see also Gatz et al., *Ann. Rev. Plant Physiol. Plant Mol. Biol.*, 48:9-108, 1997).

Alternatively, tissue-specific (root, leaf, flower, and seed, for example) promoters (Carpenter et al., *Plant Cell*, 4:557-571, 1992; Denis et al., *Plant Physiol.*, 101:1295-1304, 1993; Opperman et al., *Science*, 263:221-223, 1993; Stockhause et al., *Plant Cell*, 9:479489, 1997; Roshal et al., *EMBO J.*, 6:1155, 1987; Schemthaner et al., *EMBO J.*, 7:1249, 1988; and Bustos et al., *Plant Cell*, 1:839, 1989) can be fused to the coding sequence to obtain a particular expression in respective organs.

Alternatively, the native oxygenase gene promoters may be utilized. With the provision herein of the oxygenase nucleic acid sequences, one of skill in the art will appreciate that standard molecular biology techniques can be used to determine the corresponding promoter sequences. One of skill in the art also will appreciate that less than the entire promoter sequence may be used in order to obtain effective promoter activity. The determination of whether a particular region of this sequence confers effective promoter activity may be ascertained readily by operably linking the selected sequence region to an oxygenase cDNA (in conjunction with suitable 3' regulatory region, such as the NOS 3' regulatory region as discussed below) and determining whether the oxygenase is expressed.

Plant transformation vectors also may include RNA processing signals, for example, introns, that may be positioned upstream or downstream of the ORF sequence in the transgene. In addition, the expression vectors also may include additional regulatory sequences from the 3'-untranslated region of plant genes, e.g., a 3'-terminator region, to increase mRNA stability of the mRNA, such as the PI-II terminator region of potato or the octopine or nopaline synthase (NOS) 3'-terminator regions. The native oxygenase gene 3'-regulatory sequence also may be employed.

As noted above, plant transformation vectors also may include dominant selectable marker genes to allow for the ready selection of transformants. Such genes include those encoding antibiotic resistance genes (e.g., resistance to hygromycin, kanamycin, bleomycin, G418, streptomycin, or spectinomycin) and herbicide resistance genes (e.g., phosphinothricin acetyloxygenase).

B. Arrangement of Taxol Oxygenase Sequence in a Vector

The particular arrangement of the oxygenase sequence in the transformation vector is selected according to the type of expression of the sequence that is desired. In most instances, enhanced oxygenase activity is desired, and the oxygenase ORF is operably linked to a constitutive high-level promoter such as the CaMV 35S promoter. As noted above, enhanced oxygenase activity also may be achieved by introducing into a plant a transformation vector containing a variant form of the oxygenase cDNA or gene, for example a form that varies from the exact nucleotide sequence of the oxygenase ORF, but that encodes a protein retaining an oxygenase biological activity.

C. Transformation and Regeneration Techniques

Transformation and regeneration of a wide variety of plant species, including gymnosperms, angiosperms, monocots and dicots are now routine (see, e.g., Glick and Thompson, eds., *Methods in Plant Molecular Biology*, CRC Press, Boca Raton, Fla., 1993), and the appropriate transformation technique can be determined by the practitioner. The choice of method varies with the type of plant to be transformed; those skilled in the art will recognize the suitability of particular methods for given plant types. Suitable methods may include, but are not limited to: electroporation of plant protoplasts (e.g., Rhodes et al., *Science*, 240(4849):204-207, 1988); liposome-mediated transformation; polyethylene glycol (PEG)-mediated transformation (e.g., Lyznik et al., *Plant Mol. Biol.*, 13:151-161, 1989); transformation using viruses (e.g., Brisson et al., *Nature*, 310:511-514, 1984); microinjection of plant cells (e.g., de la Pena et al., *Nature*, 325:274-276, 1987); micro-projectile bombardment of plant cells (Klein et al., *Plant Physiol.*, 91:440-444, 1989; Boynton et al., *Science*, 240(4858):1534-1538, 1988); vacuum infiltration; and *Agrobacterium tumefaciens* (AT)-mediated transformation. Exemplar procedures for transforming and regenerating plants are described, for instance, in the patent documents listed at the beginning of this section. Additionally, plant transformation strategies and techniques are reviewed by Birch (*Ann. Rev. Plant Phys. Plant Mol. Biol.*, 48:297, 1997), and Forester et al (*Exp. Agric.*, 33:15-33, 1997).

In particular embodiments, transformation of *Taxus* species can be achieved, for example, by employing the methods of Han et al. (*Plant Science*, 95:187-196, 1994).

D. Selection of Transformed Plants

Following transformation and regeneration of plants with the transformation vector, transformed plants or cells can be selected using a selectable marker incorporated into the transformation vector. In some examples, such a marker confers antibiotic resistance on the seedlings of transformed plants, and selection of transformants can be accomplished by exposing the seedlings to appropriate concentrations of the antibiotic. For instance, a commonly used selectable marker gene is neomycin phosphotransferase II (NPT II), which confers resistance to the antibiotic, kanamycin. Another selectable marker gene which can be employed is the gene which confers resistance to the herbicide glufosinate (Basta). A screenable gene commonly used is the 0-glucuronidase gene (GUS). The presence of this gene is characterized using a histochemical reaction in which a sample of putatively transformed cells is treated with a GUS assay solution. After an appropriate incubation, the cells containing the transformation vector (which includes the GUS gene) turn blue.

After transformed plants are selected and grown to maturity, they can be assayed using the methods described herein to assess production levels of paclitaxel and other taxoids.

VII. Production of Recombinant Taxoid Oxygenase in Heteralogous Expression Systems Various commonly known systems are available for heterologous expression of the disclosed 5α-hydroxylase nucleic acid molecules to yield the encoded proteins, including, eukaryotic and prokaryotic expression systems. In some examples, eukaryotic expression systems are used to facilitate postranslational modification of the expressed protein and/or to direct the expressed protein to a desired cellular compartment.

Methods of expressing proteins in heterologous expression systems are well known in the art. Typically, a nucleic acid molecule encoding all or part of the protein of interest, such as a 5α-hydroxylase, is obtained using methods such as those described herein. The protein-encoding nucleic acid sequence is cloned into an expression vector that is suitable for the particular host cell of interest using standard recombinant DNA procedures. Expression vectors include (among other elements) regulatory sequences (e.g., promoters) that can be operably linked to the desired protein-encoding nucleic acid molecule to cause the expression of such nucleic acid molecule in the host cell. Together, the regulatory sequences and the protein-encoding nucleic acid sequence are an "expression cassette." Expression vectors may also include an origin of replication, marker genes that provide phenotypic selection in transformed cells, one or more other promoters, and a polylinker region containing several restriction sites for insertion of heterologous nucleic acid sequences.

Expression vectors useful for expression of heterologous protein(s) in a multitude of host cells are well known in the art, and some specific examples are provided herein. The host cell is transfected with (or infected with a virus containing) the expression vector using any method suitable for the particular host cell. Such transfection methods are also well known in the art and non-limiting exemplar methods are described herein. The transfected (also called, transformed) host cell is capable of expressing the protein encoded by the corresponding nucleic acid sequence in the expression cassette. Transient or stable transfection of the host cell with one or more expression vectors is contemplated by the present disclosure.

The cloned expression vector encoding one or more of the disclosed oxygenases may be transformed into any of various cell types for expression of the cloned nucleotide. Many different types of cells may be used to express modified nucleic acid molecules. Examples include cells of yeasts, fungi, insects, mammals, and plants, including primary cells and immortal cell lines. For instance, common mammalian cells that could be used include HeLa cells, SW-527 cells (ATCC deposit #7940), WISH cells (ATCC deposit #CCL-25), Daudi cells (ATCC deposit #CCL-213), Mandin-Darby bovine kidney cells (ATCC deposit #CCL-22) and Chinese hamster ovary (CHO) cells (ATCC deposit #CRL-2092). Common yeast cells include *Pichia pastoris* (ATCC deposit #201178) and *Saccharomyces cerevisiae* (ATCC deposit #46024). Insect cells include cells from *Drosophila melanogaster* (ATCC deposit #CRL-10191), the cotton bollworm (ATCC deposit #CRL-9281), and *Trichoplitsia ni* egg cell homoflagellates. Fish cells that may be used include those from rainbow trout (ATCC deposit #CLL-55), salmon (ATCC deposit #CRL-1681), and zebrafish (ATCC deposit #CRL-2147). Amphibian cells that may be used include those of the bullfrog, *Rana catesbelana* (ATCC deposit #CLL-41). Reptile cells that may be used include those from Russell's viper (ATCC deposit #CCL-140). Plant cells that could be used include *Chlamydomonas* cells (ATCC deposit #30485), *Arabidopsis* cells (ATCC deposit #54069), tomato plant cells (ATCC deposit #54003) and *Taxus* cells (including, e.g., cells from *T. cuspidata*, *T. brewfolia*, *T. canadensis*, *T. baccata*, *T. globosa*, *T. floridana*, *T. wallichiana*, *T. media* and *T. chinensis*). Many of these cell types are commonly used and are available from the ATCC as well as from commercial suppliers such as Pharmacia (Uppsala, Sweden), and Invitrogen.

Expressed protein may be accumulated within a cell or may be secreted from the cell. Such expressed protein may then be collected and purified. This protein may be characterized for activity and stability and may be used to practice any of the various methods disclosed herein. Further details of some specific embodiments are discussed below.

A. Yeast

Various yeast strains and yeast-derived vectors are used commonly for the expression of heterologous proteins. For instance, *Pichia pastoris* expression systems, obtained from Invitrogen (Carlsbad, Calif.), may be used to express the disclosed P450 oxygenases, such as a taxoid 5α-hydroxylase.

Such systems include suitable *Pichia pastoris* strains, vectors, reagents, transformants, sequencing primers, and media. Available strains include KM71H (a prototrophic strain), SMD1168H (a prototrophic strain), and SMD1168 (a pep4 mutant strain) (Invitrogen Product Catalogue, 1998, Invitrogen, Carlsbad Calif.).

*Saccharomyces cerevisiae*, is another yeast that is commonly used in heterologous expression systems. The plasmid YRp7 (Stinchcomb et al., *Nature*, 282:39, 1979; Kingsman et al., *Gene*, 7:141, 1979; Tschemper et al., *Gene*, 10:157, 1980) is commonly used as an expression vector in *Saccharomyces*. This plasmid contains the trp1 gene that provides a selection marker for a mutant strain of yeast lacking the ability to grow in tryptophan, such as strains ATCC No. 44,076 and PEP4-1 (Jones, *Genetics*, 85:12, 1977). The presence of the trp1 lesion as a characteristic of the yeast host cell genome then provides an effective environment for detecting transformation by growth in the absence of tryptophan.

Yeast host cells can be transformed using the polyethylene glycol method, as described by Hinnen (*Proc. Natl. Acad. Sci. USA*, 75:1929, 1978). Additional yeast transformation protocols are set forth in Gietz et al. (*Nucl. Acids Res.*, 20(17):1425, 1992) and Reeves et al. (*FEMS*, 99(2-3):193-197, 1992).

Suitable promoting sequences in yeast vectors include the promoters for 3-phosphoglycerate kinase (Hitzeman et al., *J. Biol. Chem.*, 255:2073, 1980) or other glycolytic enzymes (Hess et al., *J. Adv. Enzyme Reg.*, 7:149, 1968; Holland et al., *Biochemistry*, 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression vectors, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Non-yeast eukaryotic vectors may be used with equal facility for expression of proteins encoded by modified nucleotides according to the invention. Mammalian vector/host cell systems containing genetic and cellular control elements capable of carrying out transcription, translation, and post-translational modification are well known in the art. Examples of such systems are the well known baculovirus system, the ecdysone-inducible expression system that uses regulatory elements from *Drosophila melanogaster* to allow control of gene expression, and the sindbis viral expression system that allows high-level expression in a variety of mammalian cell lines, all of which are available from Invitrogen (Carlsbad, Calif.).

B. Baculovirus-Infected Insect Cells

Another representative eukaryotic expression system involves the recombinant baculovirus, *Autographa californica* nuclear polyhedrosis virus (AcNPV; Summers and Smith, *A Manual of Methods for Baculovirus Vectors and Insect Cell Culture Procedures*, 1986; Luckow et al., *Biotechnol.*, 6:47-55, 1987). Infection of insect cells (such as cells of the species *Spodoptera frugiperda*) with the recombinant baculoviruses results in the expression taxoid 5α-hydroxylase protein in the insect cells. Baculoviruses do not infect humans and can therefore be safely handled in large quantities.

A baculovirus expression vector is prepared as previously described using standard molecular biology techniques. The vector may comprise the polyhedron gene promoter region of a baculovirus, the baculovirus flanking sequences necessary for proper crossover during recombination (the flanking sequences comprise about 200-300 base pairs adjacent to the promoter sequence) and a bacterial origin of replication which permits the construct to replicate in bacteria. In particular examples, the vector is constructed so that (i) the taxoid 5α-hydroxylase protein-encoding nucleic acid sequence is operably linked to the polyhedron gene promoter (collectively, the "expression cassette") and (ii) the expression cassette is flanked by the above-described baculovirus flanking sequences.

Insect host cells (such as, *Spodoptera frugiperda* cells) are infected with a recombinant baculovirus and cultured under conditions allowing expression of the baculovirus-encoded taxoid 5α-hydroxylase. The expressed oxygenase may, if desired, be extracted from the insect cells using methods known in the art.

C. Mammalian Cells

Mammalian host cells may also be used for heterologous expression of a disclosed oxygenase, such as a taxoid 5α-hydroxylase. Examples of suitable mammalian cell lines include, without limitation, monkey kidney CVI line transformed by SV40 (COS-7, ATCC CRL 1651); human embryonic kidney line 293S (Graham et al., *J. Gen. Virol.*, 36:59, 1977); baby hamster kidney cells (BHK, ATCC CCL 10); Chinese hamster ovary cells (Urlab and Chasin, *Proc. Natl. Acad. Sci USA*, 77:4216, 1980); mouse sertoli cells (TM4, Mather, *Biol. Reprod.*, 23:243, 1980); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 5 1); rat hepatoma cells (HTC, MI.54, Baumann et al., *J. Cell Biol.*, 85:1, 1980); and TRI cells (Mather et al., *Annals N.Y. Acad. Sci.*, 383:44, 1982). Expression vectors for these cells ordinarily include (if necessary) DNA sequences for an origin of replication, a promoter located in front of the gene to be expressed, a ribosome binding site, an RNA splice site, a polyadenylation site, and/or a transcription terminator site.

Promoters used in mammalian expression vectors can be of viral origin. Such viral promoters may be derived from polyoma virus, adenovirus 2, and simian virus 40 (SV40). The SV40 virus contains two promoters that are termed the early and late promoters. These promoters are useful because they are both easily obtained from the virus as one nucleic acid fragment that also contains the viral origin of replication (Fiers et al., *Nature*, 273:113, 1978). Smaller or larger SV40 DNA fragments may also be used, provided they contain the approximately 250-bp sequence extending from the HindIII site toward the BglI site located in the viral origin of replication. Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., polyoma virus, adenovirus, VSV, BPV) and inserted into the expression vector. Alternatively, the origin of replication may be provided by the host cell chromosomal replication mechanism.

D. Prokaryotes

Prokaryotes may also be used as host cells. Prokaryotic expression systems are useful for (among other things) rapid production of large amounts of plasmid DNA, for production of single-stranded DNA templates used for site-directed mutagenesis, for screening many mutants simultaneously, and for DNA sequencing of the mutants generated. Suitable prokaryotic host cells include, without limitation, *E. coli* K12 strain 94 (ATCC No. 31,446), *E. coli* strain W3 110 (ATCC No. 27,325), *E. coli* X1776 (ATCC No. 31,537), and *E. coli* B; however many other strains of *E. coli*, such as HB101, JM101, NM522, NM538, NM539, and many other species and genera of prokaryotes including *bacilli* such as *Bacillus subtilis*, other enterobacteriaceae, such as *Salmonella typhimurium* or *Serratia marcesans*, and various *Pseudomonas* species may all be used as hosts.

Prokaryotic host cells or other host cells with rigid cell walls may be transformed using any method known in the art, including, for example, calcium phosphate precipitation, or electroporation. Representative prokaryote transformation techniques are described in Dower (*Genetic Engineering, Principles and Methods*, 12:275-296, Plenum Publishing Corp., 1990) and Hanahan et al. (*Meth. Enzymol.*, 204:63, 1991).

Plasmids typically used for transformation of *E. coli* include, without limitation, pBR322, pUC18, pUC19, pUCI18, pUCI19, Bluescript M13 and derivatives thereof. Numerous such plasmids are commercially available and are well known in the art. Representative promoters used in prokaryotic vectors include the β-lactamase (penicillinase) and lactose promoter systems (Chang et al., *Nature*, 375:615, 1978; Itakura et al., *Science*, 198:1056, 1977; Goeddel et al., *Nature*, 281:544, 1979), a tryptophan (trp) promoter system (Goeddel et al., *Nucl. Acids Res.*, 8:4057, 1980), and the alkaline phosphatase system E. Heterologous Protein Trafficking Trafficking sequences from plants, animals and microbes can be employed to direct the expression of a disclosed oxygenase, such as a 5α-hydroxylase, to the cytoplasm, endoplasmic reticulum, mitochondria or other cellular compartment, or to target the protein for export to the medium.

Many eukaryotic proteins contain an endogenous signal sequences. The nucleic acid sequence encoding a signal sequence may be obtained as a restriction fragment from any gene encoding a protein with a signal sequence. By ligating DNA encoding a signal sequence to the 5' end of the DNA encoding a protein of interest, the resultant chimeric protein can be directed to the destination conveyed by the signal sequence.

The signal sequences of several eukaryotic genes are known, including, for example, human growth hormone, proinsulin, and proalbumin (see, e.g., Stryer, Biochemistry, Third Edition, W.H. Freeman and Company, New York, N.Y., p. 769, 1988), and can be used as signal sequences in appropriate eukaryotic host cells. Yeast signal sequences, such as acid phosphatase (Aria et al., *Nucl. Acids Res.*, 11:1657, 1983), α-factor, alkaline phosphatase and invertase, may be used to direct secretion from yeast host cells. Prokaryotic signal sequences from genes encoding, for example, Lam or OmpF (Wong et al., *Gene*, 68:193, 1988), MalE, PhoA, or β-lactamase, as well as other genes, may be used to target proteins from prokaryotic cells into the culture medium.

VIII. Production of an Antibody to a Taxoid 5α-hydroxylase Protein

Monoclonal or polyclonal antibodies may be produced to either the normal taxoid 5α-hydroxylase protein or variants of this protein. In one embodiment, antibodies raised against the taxoid 5α-hydroxylase protein would specifically detect the taxoid 5α-hydroxylase protein. That is, such antibodies would recognize and bind the taxoid 5α-hydroxylase protein, or fragments thereof, and would not substantially recognize or bind to other proteins found in *Taxus* cells. In some embodiments, antibodies against the *Taxus cuspidata* taxoid 5α-hydroxylase protein may recognize taxoid 5α-hydroxylase from other paclitaxel-producing species (e.g. *Taxomyces andreanae*), and vice versa. Antibodies to the disclosed oxygenase enzymes, and fragments thereof, may be also useful for purification of the enzymes.

The determination that an antibody specifically binds to an antigen is made by any one of a number of standard immunoassay methods; for instance, Western blotting (see, Sambrook et al. (eds.), *Molecular Cloning: A Laboratory Manual*, 2nd ed., vols. 1-3, Cold Spring Harbor Laboratory Press, Cold Spring Harbor, N.Y., 1989). To determine that a given antibody preparation (such as a preparation produced in a mouse against SEQ ID NO: 2) specifically detects the oxygenase by Western blotting, total cellular protein is extracted from cells and electrophoresed on an SDS-polyacrylamide gel. The proteins are electrophoretically transferred to a membrane (for example, nitrocellulose), and the antibody preparation is incubated with the membrane. After washing the membrane to remove non-specifically bound antibodies, the presence of specifically bound antibodies is detected by the use of a detector molecule (such as, an anti-mouse antibody conjugated to an enzyme such as alkaline phosphatase). Antibodies that specifically detect an oxygenase will be shown, by this technique, to bind substantially only the oxygenase band (having a position on the gel determined by the molecular weight of the oxygenase).

Substantially pure oxygenase suitable for use as an immunogen can be isolated from transfected cells, transformed cells, or from wild-type cells. Concentration of protein in the final preparation is adjusted, for example, by concentration on an Amicon filter device, to the level of a few micrograms per milliliter. Alternatively, peptide fragments of an oxygenase may be utilized as immunogens. Such fragments may be synthesized chemically using standard methods, or may be obtained by cleavage of the whole oxygenase enzyme followed by purification of the desired peptide fragments. Peptides as short as three or four amino acids in length are immunogenic when presented to an immune system in the context of a Major Histocompatibility Complex (MHC) molecule, such as MHC class I or MHC class H. Accordingly, peptides comprising at least 3 and preferably at least 4, 5, 6 or more consecutive amino acids of the disclosed oxygenase amino acid sequences may be employed as immunogens for producing antibodies.

Because naturally occurring epitopes on proteins frequently comprise amino acid residues that are not adjacently arranged in the peptide when the peptide sequence is viewed as a linear molecule, it may be advantageous to utilize longer peptide fragments from the oxygenase amino acid sequences for producing antibodies. Thus, for example, peptides that comprise at least 10, 15, 20, 25, or 30 consecutive amino acid residues of the amino acid sequence may be employed. Monoclonal or polyclonal antibodies to the intact oxygenase, or peptide fragments thereof may be prepared as described below.

A. Monoclonal Antibody Production by Hybridoma Fusion

Monoclonal antibodies can be prepared from murine hybridomas according to the classical method of Kohler and Milstein (*Nature*, 256:495-497, 1975) or derivative methods thereof. In one specific, non-limiting embodiment, a mouse is repetitively inoculated with a few micrograms of the selected protein over a period of a few weeks. The mouse is then sacrificed, and the antibody-producing cells of the spleen isolated. The spleen cells are fused with mouse myeloma cells using polyethylene glycol, and the excess, non-fused, cells destroyed by growth of the system on selective media comprising aminopterin (HAT media). Successfully fused cells are diluted and aliquots of the dilution placed in wells of a microtiter plate, where growth of the culture is continued. Antibody-producing clones are identified by detection of antibody in the supernatant fluid of the wells by immunoassay procedures, such as ELISA, as originally described by Engvall (*Enzymol.*, 70(A):419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, Cold Spring Harbor Laboratory Press, New York, 1988).

B. Polyclonal Antibody Production by Immunization

Polyclonal antiserum containing antibodies to heterogeneous epitopes of a single protein can be prepared by immunizing suitable animals with the expressed protein (for instance, expressed using a method described herein), which, in one specific, non-limiting embodiment, can be modified to enhance immunogenicity. Effective polyclonal antibody production is affected by many factors related both to the antigen and the host species. In one embodiment, small molecules may tend to be less immunogenic than others and may require the use of carriers and adjuvant, examples of which are known. In another embodiment, host animals may vary in response to site of inoculations and dose, with either inadequate or excessive doses of antigen resulting in low titer antisera. In one specific, non-limiting embodiment, a series of small doses (ng level) of antigen administered at multiple intradermal sites may be most reliable. An effective immunization protocol for rabbits can be found in Vaitukaitis et al. (*J. Clin. Endocrinol. Metab.*, 33:988-991, 1971).

In one embodiment, booster injections will be given at regular intervals, and antiserum harvested when antibody titer thereof begins to fall, as determined semi-quantitatively (for example, by double immunodiffusion in agar against known concentrations of the antigen). See, for example, Ouchterlony et al. (in *Handbook of Experimental Immunology*, Wier, D. (ed.) chapter 19. Blackwell, 1973). In one specific, non-limiting embodiment the plateau concentration of antibody is usually in the range of about 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

C. Antibodies Raised against Synthetic Peptides

A third approach to raising antibodies against the taxoid 5α-hydroxylase protein is to use synthetic peptides synthesized on a commercially available peptide synthesizer based upon the predicted amino acid sequence of the taxoid 5α-hydroxylase protein. Polyclonal antibodies can be generated by injecting such peptides into, for instance, rabbits.

D. Antibodies Raised by Injection of Taxoid 5α-Hydroxylase Encoding Sequence In one embodiment, antibodies may be raised against the taxoid 5α-hydroxylase protein by subcutaneous injection of a recombinant DNA vector that expresses the taxoid 5α-hydroxylase protein into laboratory animals, such as mice. In one specific, non-limiting embodiment, delivery of the recombinant vector into the animals may be achieved using a hand-held form of the Biolistic system (Sanford et al., *Particulate Sci. Technol.*, 5:27-37, 1987), as described by Tang et al. (*Nature*, 356:152-154, 1992). In other embodiments, expression vectors suitable for this purpose may include those that express the taxoid 5α-hydroxylase encoding sequence under the transcriptional control of either the human β-actin promoter or the cytomegalovirus (CMV) promoter.

IX. Methods of Using 5α-Hydroxylase

The creation of recombinant vectors and transgenic organisms expressing vectors disclosed herein are useful for controlling the production of the disclosed oxygenases, such as the 5α-hydroxylase. These vectors can be used to decrease oxygenase production or to increase oxygenase production. Increased production of oxygenase can be achieved by including at least one additional oxygenase encoding sequence in the vector. These vectors can be introduced into a host cell, thereby altering oxygenase production. In the case of increased production, the resulting oxygenase may be used in in vitro systems, as well as in vivo for increased production of paclitaxel, other taxoids, intermediates of the paclitaxel biosynthetic pathway, and other products.

A. Production of Paclitaxel or Other Taxoid In Vivo

One attractive alternative to yew harvest and/or paclitaxel semisynthesis is the production of paclitaxel and taxoids in vivo, such as in transgenic organisms and/or cell culture (including, for example, *Taxus* cell culture). Cell culture, for example, lends itself to vat fermentation format (potentially as a continuous process), a high level of process control, and ease of product isolation and purification. This practice further provides the possibility of biochemical/molecular manipulation to direct biosynthesis to specific taxoid precursors, modified forms, and derivatives.

In current practice at the small scale, *Taxus* cell cultures produce about 10-100 mg/L of paclitaxel (up to 1 gram total taxoids/L) in production runs of about 7-10 days; however, production levels are quite variable and not sustainable with time or at scale. Commercially viable production levels of paclitaxel are estimated to be between about 200-400 mg/L and of precursors for semi-synthesis in the range of about 400-800 mg/L range. Enhancement of production levels and/or redirection of taxoid metabolism can be useful to achieve economic viability. Preferably, production levels are consistent and reliable. A system that is biochemically manipulable can permit synthesis of a range of taxoid derivatives (e.g., alternative precursors and second generation drugs). Such a system is now enabled by the disclosure of the 5α-hydroxylase protein and nucleic acid sequences. This enzyme is believed to catalyze a slow-step in the paclitaxel biosynthetic pathway, thus, alone and in combination with other enzymes of the paclitaxel pathway, the disclosed 5α-hydroxylase protein and nucleic acid sequences permit molecular genetic manipulation (genetic engineering) of cultured cells, such as *Taxus* cells, to increase yields of paclitaxel and to direct the pathway to desirable taxoid metabolites.

Production of paclitaxel and related taxoids (such as, taxoid-5-ols, including isomers of taxadien-5-ol) in vivo can be accomplished by transfecting a host cell, such as one derived from the *Taxus* genus, with a vector capable of expressing, at least, a disclosed oxygenase (such as, a taxoid 5α-hydroxylase). Methods of making and using suitable expression vectors and transforming a variety of cell types with such vectors have been described above. In certain examples, heterologous or homologous oxygenase sequences are placed under the control of a constitutive promoter, or an inducible promoter; thus, any naturally occurring feedback that might otherwise down-regulate oxygenase expression under natural conditions will be eliminated.

In some methods, the host cell does not produce any paclitaxel prior to transfection, in which case, particular methods can involve feeding taxoids (such as, paclitaxel intermediates) to the cell. In other methods, a host cell will express a detectable amount of paclitaxel prior to transfection so that transfection with the expression vector increases the production of paclitaxel in the transfected cell. In particular examples of these methods, paclitaxel production in a transfected cell may be increased by at least two fold, such as at least four fold, at least 10 fold, at least 20 fold, at least 50 fold or at least 100 fold.

A host cell, which has been (or will be) transfected with a disclosed 5α-hydroxylase, may also be transfected (using either the same or a different expression vector) with nucleic acid sequences encoding other enzymes having activities useful for the biosynthesis of paclitaxel including, for example, taxadiene synthase (such as SEQ ID NO: 19 or the protein-encoding portion thereof), taxadienol acetyl transferase (such as, SEQ ID NO: 21 or the protein-encoding portion thereof; also known as TAX1 or TAT), 2-debenzoyl-7,13-diacetylbaccatin III-2-O-benzoyl transferase (such as, SEQ ID NO: 23 or the protein-encoding portion thereof; also known as TAX2), 10-deacetylbaccatin III-10-O-acetyl transferase (such as, SEQ ID NO: 34 or the protein-encoding portion thereof; also known as TAX6 or DBAT), taxoid 13-phenylpropanoyltransferase (such as, SEQ ID NO: 36 or the protein-encoding portion thereof; also known as TAX7); 3'-N-debenzoyltaxol N-benzoyltransferase (such as, SEQ ID NO: 38 or the protein-encoding portion thereof; also known as TAX10 or DBNTBT); or any of a several taxoid oxygenases, including, without limitation, taxoid 7β-hydroxylase, taxoid 14β-hydroxylase, taxoid 10β-hydroxylase, taxoid 13α-hydroxylase, or taxoid 2α-hydroxylase (such as, one or more of the taxoid oxygenases set forth in SEQ ID NOs: 3, 5, 7, 9, 11, 13, 15, 17 or 40). Variants of each of the foregoing enzymes, which maintain the function of the prototype enzyme, would be equally suitable for use in the above-described multi-gene expression system. Such variants can be, for instance, at least 70%, at least 80%, at least 90%, or at least 95% percent identical to either the nucleic acid sequence encoding, or the amino acid sequence of, the prototype enzyme.

Methods and constructs for the introduction of multiple protein-encoding nucleic acids sequences (such as, cDNAs) into cells, such as plant cells (including, e.g., *Taxus* cell lines), using single or multiple transformation event(s) have been described (see, e.g., U.S. Pat. No. 6,337,431; U.S. Pat Pub. No. 20020129400, U.S. Pat Pub. No. 20020059660; de Felipe, *Curr. Gene Ther.*, 2(3):355-378, 2002). For example, techniques commonly used for introduction of multiple genes into cells include: (i) co-transformation with mixed multiple plasmid vectors containing different protein-encoding sequences using any transfection method known in the art (e.g. Chen et al., *Nat. Biotechnol.*, 16:1060-1064, 1998; Ye et al., *Science*, 287:303-305, 2000); (ii) sequential re-transformation of the same recipient cell (or cell population) with vectors where each vector contains one or a few protein-encoding sequences (e.g., Lapierre et al., *Plant Physiol.*, 119: 153-163, 1999); or sexual crossing between transgenic organisms carrying different transgenes to recombine the genes to a single organism (e.g., Ma et al., *Science*, 268:716-719, 1995); and (iii) linking of multiple genes of different sources into the same vector using conventional molecular cloning technology for transformation (e.g., Van Engelen et al., *Plant Mol. Biol.*, 26:1701-1710, 1994; Daniell and Dhingra, *Curr. Opin. Biotechnol.*, 13:136-141 2001). In particular examples, a multi-gene construct includes a promoter, nucleic acid sequences encoding two or more proteins, inteins, and transcription termination sequences and, optionally, sequences encoding targeting sequences, or tissue specific sequences, such as tissue-specific targeting peptides.

Cells may be transfected (i.e., transformed) with one or more constructs useful for the expression of multiple protein-encoding sequences in a single cell in any manner known in the art or as described herein including, without limitation, Agrobracterium transformation of plant cells (see, for instance, Han et al., *Plant Sci.*, 95(2):187-196, 1994).

B. Production of Paclitaxel or Other Taxoids In Vitre

Currently, paclitaxel is produced by a semisynthetic method described in Hezari and Croteau, *Planta Medica*, 63:291-295, 1997. This method involves extracting 10-deacetyl-baccatin III, or baccatin III, intermediates in the paclitaxel biosynthetic pathway, and then finishing the production of paclitaxel using chemical techniques. With the provision of a taxoid 5α-hydroxylase herein, it is now possible to utilize this enzyme (and its variants) to hydroxylate taxoids (such as, paclitaxel intermediates) to produce taxoid-5-ols (including for example, taxadien-5-ol isomers). Such taxoid-5-ols can be used, for example, to facilitate the production of paclitaxel and related taxoids.

In vitro methods involve transfection of a host cell with a vector expressing a disclosed 5α-hydroxylase, as described previously. Following transfection, the recombinant enzyme may hydroxylate available taxoid substrates (including, e.g., taxadiene isomers such as, taxa-4(5),11(12)-diene, and taxa-4(20),11(12)-diene). Such substrates can be naturally present in the host cell (such as, a *Taxus* cell) or can be administered to the host cell, for example, by adding the exogenous substrate to the media bathing the cells. Under these circumstances, 5α-hydroxylation of the substrate can occur in vivo (as discussed in the preceding section) and the resultant product, such as a taxadien-5-ol, can be extracted and/or purified for further in vitro processing, including the synthesis of paclitaxel, paclitaxel intermediates, or other taxoids.

In other methods, the 5α-hydroxylase protein can be isolated from transfected cells. The isolated protein can, then, be used as a reagent in reactions involving the 5α-hydroxylation of taxoid substrates, including taxadiene isomers (such as, taxa-4(5),11(12)-diene, and taxa-4(20),11(12)-diene).

Embodiments of the invention are illustrated by the following non-limiting Examples.

EXAMPLES

Example 1

Homology-Based Cloning of Cytochrome P450 Oxygenases from *Taxus*

Previous studies have used DD-RT PCR to obtain cytochrome P450 taxoid oxygenase clones from methyl jasmonate-induced *Taxus* cells. The DD-RT PCR method is limited because it may fail to identify transcripts that are not highly induced by the inducing agent used in the method. This example describes a strategy for cloning taxoid oxygenases, such as the disclosed taxoid 5α-hydroxylase, that is not subject to the biases of DD-RT PCR (Udvardi et al., *Plant Physiol.*, 105:755-756, 1994; Holton and Lester, *Methods*

*Enzymol.*, 272:275-283, 1996; Pauli and Kutchan, *Plant J.* 13:793-801, 1998). This strategy is based upon two highly conserved regions of P450 oxygenase proteins, the commonly occurring PERF motif and the region surrounding the invariant, heme-binding cysteine residue (von Wachenfeldt and Johnson, "Structures of eukaryotic cytochrome P450 enzymes," In: Cytochrome P450: Structure, Mechanism, and Biochemistry, 2nd Ed., P. R. Ortiz de Montollano, ed., New York: Plenum, pp. 183-223, 1995).

Unless expressly stated otherwise, enzymes and reagents used in this and other Examples were obtained from Gibco/BRL (Grand Island, N.Y.), Invitrogen (Carlsbad, Calif.), New England Biolabs (Beverly, Mass.) and Stratagene (La Jolla, Calif.), as indicated, and were used according to the respective manufacturer's instructions. Other chemicals were purchased from Merck (Darmstadt, Germany) and Sigma (St. Louis, Mo.).

Degenerate and inosine-containing oligonucleotide forward primers directed to the PERF motif and its variant forms were designed based on amino acid sequence alignments of cytochrome P450 oxygenases of plant origin, which were available in the public databases. The following forward primers directed to the PERF motif were synthesized:

```
5'-TTY MGI CCI AGM GIT TYG AR-3'      (SEQ ID NO: 25)

5'-TTY MGI CCI TCI MGI TTY GAR-3'     (SEQ ID NO: 26)

5'-CKI III CCI GCI CCR AAI GG-3'      (SEQ ID NO: 27)

5'-GAR GAR TTY MGN CCN GAR MG-3'      (SEQ ID NO: 28)

5'-GAR AAR TTY III CCI GAI ARG TTY    (SEQ ID NO: 29)
```

Using a similar strategy, degenerate and inosine-containing oligonucleotide reverse primers directed to the conserved heme-binding region were designed and synthesized. These reverse primers are:

```
                                      (SEQ ID NO: 30)
5'-GGR CAI III CKI III CCI CCI CCR AAI GG-3'

(SEQ ID NO: 31)
5'-CCI GGR CAI ATI MKY YTI CCI GCI CCR AAI GG-3'.
```

Amplification (Pauli and Kutchan, *Plant J.*, 13:793-801, 1998), using first strand cDNA template derived from mRNA isolated from *T. cuspidata* cells 16 hours post-induction with methyl jasmonate (Ketchum et al., *Biotechnol. Bioengin.*, 62:97-105, 1999; Schoendorf et al., *Proc. Natl. Acad. Sci. USA*, 98:1501-1506, 2001), yielded amplicons of the predicted size (i.e., about 200 base pairs). The amplicons were gel purified, ligated into pGEM-T (Promega, Madison, Wis.), and transformed into *E. coli* JM109 cells for plasmid preparation and insert sequencing.

Based on the amplicon sequences, probes of 40 to 50 nucleotides in length were synthesized, 5'-labeled with [$^{32}$P] dCTP (ICN, Irvine, Calif.) using T4 polynucleotide kinase (New England Biolabs, Beverly, Mass.), and used to screen the previously described induced *T. cuspidata* λ-ZAPII™ cDNA library (Schoendorf et al., *Proc. Natl. Acad. Sci. USA*, 98:1501-1506, 2001) by employing Rapid-Hyb™ (Amersham Pharmacia, Piscataway, N.J.) solution. Following 3 rounds of screening, 32 positive plaques were in vivo excised as pBluescript II SK(-)™ phagemids in accordance with the manufacturer's (Stratagene) protocol, and partially sequenced using T3 and T7 promoter primers. Based on sequence information, clones that were previously obtained by the DD-RT PCR screen (Schoendorf et al., *Proc. Natl. Acad. Sci. USA*, 98:1501-1506, 2001) were set aside and not further examined. These new clones were obtained in full-length form by Marathon™ 5'-RACE (Clontech, Palo Alto, Calif.), as necessary, and were fully sequenced.

One clone, designated S1, represented the most abundant cytochrome P450 cDNA isolated by this homology-based cloning approach. The S1 clone was 1688 base pairs in length (GenBank accession no. AY289209) and contained an apparent ORF of 1509 base pairs encoding a predicted protein of 502 amino acids with deduced molecular weight of 56,859 Daltons. The deduced amino acid sequence of clone S1 exhibited characteristics commonly known in the art to be typical of cytochrome P450 enzymes (von Wachenfeldt and Johnson, "Structures of eukaryotic cytochrome P450 enzymes," In: *Cytochrome P450: Structure, Mechanism, and Biochemistry*, 2nd Ed., P. R Ortiz de Montellano, ed., New York: Plenum, pp. 183-223, 1995), including the oxygen-binding domain (amino acid residues 270-285), an N-terminal membrane anchor (amino acid residues 1-30), the highly conserved heme-binding motif (amino acid residues 433-441) with PFG element (amino acids at positions 437-439), and the absolutely conserved cysteine at position 445.

Comparisons of the clone S1 deduced amino acid sequence with the amino acid sequences of previously characterized cytochrome P450 taxoid hydroxylases, including the taxoid 10β-hydroxylase (GenBank Accession No. AF318211), 13α-hydroxylase (GenBank Accession No. AY056019) and 14β-hydroxylase (GenBank Accession No. AY188177), revealed overall identities in the 61-63% range and similarities in the 79-81% range (FIG. 2).

The sequence analyses described in this Example provide strong evidence that clone S1 encodes a taxoid oxygenase.

Example 2

Cytochrome P450 cDNA Expression in Yeast

This Example demonstrates one method for readily expressing taxoid oxygenases, such as taxoid 5α-hydroxylase, in yeast.

For functional expression in *Saccharomyces cerevisiae*, the deduced ORFs of clone S1 was amplified by PCR using a gene-specific forward primer (containing the ATG start codon) and a corresponding reverse primer in which the stop codon was deleted to permit read-through when transferred to the expression vector, pYES2.1/V5-HIS-TOPO™ (Invitrogen) (see, e.g., SEQ ID NOs: 32 and 33).

The clone S1 ORF amplicon was cloned into pYES2.1/V5-HIS-TOPO™ using standard techniques. Vector sequences in frame with the cloned S1 ORF encode the simian V5 epitope and a histidine ($His_6$) tag. Thus, the resultant expression vector (referred to herein as pYES2.1/S1-V5-HIS) encodes a fusion protein containing the complete clone S1 protein with a C-terminal simian V5 epitope and histidine ($His_6$) tag. This tagging procedure allows detection of the expressed enzyme via immunoblot analysis of the microsomal protein preparation using commercially available antibodies, and has been shown not to compromise the activity of other recombinant taxoid hydroxylases (Jennewein et al., *Arch. Biochem. Biophys.*, 413:262-270, 2003). The pYES2.1/S1-V5-HIS insert was sequenced using the Gall (forward) and V5 C-term (reverse) primers (available from Invitrogen) to confirm that expected S1 ORF sequence was present and in the correct orientation for expression.

The verified S1 clone expression vector was transformed into *Saccharomyces cerevisiae* strain WAT11 using the lithium acetate method (Ito et al., *J. Bacteriol.*, 153:163-168, 1983). The WAT11 strain harbors a galactose-inducible NADPH-cytochrome P450 reductase from *Arabidopsis thaliana*, which is required for efficient reductive coupling to the cytochrome (Pompon et al., *Methods Enzymol.*, 272:51-64, 1996). This yeast expression system also permits testing of catalytic activity by in vivo feeding of taxoid substrates to the transformed yeast (Schoendorf et al., *Proc. Natl. Acad. Sci. USA*, 98:1501-1506, 2001), thereby eliminating the need for microsome isolation in preliminary functional screening assays (as discussed in more detail in Example 3).

Transformed yeast cells were grown to stationary phase in 2 ml of SGIA medium at 30° C. with 250 rpm mixing. The cells were then harvested by centrifugation (2000 g, 10 minutes) and the cell pellet was suspended in 3 ml YPLA galactose-containing induction medium Approximately 9 hours after induction, the cells were harvested again by centrifugation.

For immunoblotting, the cells were resuspended in lysis buffer (100 mM Tris HCl, pH 8.5, containing 1 mM DTT and 10% v/v glycerol), lysed by sonication (VirSonic, microtip probe, medium setting, 3×30 sec, VirTis Co., Gardiner, N.Y.) or by use of a Bead Beater (Biospec Products, Bartlesville, Okla.), and the microsomes prepared (Pompon et al., *Methods Enzymol.*, 272, 51-64, 1996). Protein (50 μg) was then separated by SDS-PAGE (10% denaturing gel), transferred by wet transfer blotting to nitrocellulose and immobilized by V-crosslinking. The blot was serially incubated with mouse Penta-His-specific antibody (Qiagen, Valencia, Calif.) as primary antibody, and alkaline phosphatase-conjugated AffiniPure™ goat anti-mouse IgG (Jackson ImmunoResearch, West Grove, Pa.) as secondary antibody for detection. The Qiagen protocols were used throughout, with His-size markers as reference, and protein preparations from transformed cells harboring empty vector as negative controls.

A single protein of approximately 57 kDa was specifically identified by Western blot. The observed molecular weight of this recombinant protein agrees with the calculated molecular weight of the deduced S1 protein sequence (see Example 1).

Example 3

In Situ Screening for Cytochrome P450 Function

This Example demonstrates that clone S1 can be efficiently expressed in yeast and that taxa-4(5),11(12)-diene and taxa-4(20),11(12)-diene are exemplar high affinity substrates for the clone S1 oxygenase.

Following conformation of clone S1 expression by immunoblot analysis (see Example 2), the activity of the recombinant cytochrome P450 enzyme was demonstrated by in vivo feeding as previously described by Schoendorf et al. (*Proc. Natl. Acad. Sci USA*, 98:1501-1506, 2001). This in vivo feeding protocol eliminated the uncertainties associated with microsome isolation and in vitro assay, including the instability of P450 oxygenases in yeast membranes (Schoendorf et al., *Proc. Nail. Acad. Sci. USA*, 98:1501-1506, 2001).

Transformed and induced yeast cells were harvested by centrifugation as described in Example 2. As a negative control for the feeding experiments, the yeast host was transformed with the pYES2.1/V5-HIS-TOPO™ vector containing a β-glucuronidase insert instead of the cytochrome P450 S1 clone. The cells were resuspended in 3 ml of fresh YPLA medium to which 30 μM of the labeled test substrate was added. Test substrates included:

| Substrate (Activity) | Activity (Ci/mol) | Reference |
|---|---|---|
| (±)-[20-³H]taxa-4(5),11(12)-diene | 5.3 | Rubenstein et al., J. Label. Compds. Radiopharm., 43:481-491, 2000 |
| (±)-[20-³H]taxa-4(20),11(12)-diene | 2.6 | Rubenstein et al., J. Label. Compds. Radiopharm., 43:481-491, 2000 |
| (±)-taxa-4(20),11(12)-dien-5α-ol | 2.0 | Rubenstein et al., J. Label. Compds. Radiopharm., 43:481-491, 2000 |
| (±)-taxa-4(20),11(12)-dien-5α-yl acetate | 2.0 | Walker et al., Arch. Biochem. Biophys., 364:273-279, 1999; Lovy Wheeler et al., Arch. Biochem. Biophys., 390:265-278, 2001 |
| (±)-taxa-4(20),11(12)-dien-5α-acetoxy-10β-ol | 2.0 | Jennewein et al., Proc. Natl. Acad. Sci. USA, 98:13595-13600, 2001; Jennewein et al., Arch. Biochem. Biophys., 413:262-270, 2003 |
| (±)-taxa-4(20),11(12)-dien-5α,13α-diol | 2.0 | Jennewein et al., Proc. Natl. Acad. Sci. USA, 98:13595-13600, 2001; Jennewein et al., Arch. Biochem. Biophys., 413:262-270, 2003 |
| (+)-[³H-acetyl]taxusin[1] | 10.0 | De Case et al., Chem. Commun., 1282-1294, 1969; Chau et al., Chem. Biol., 11:663-672, 2004; Chau and Croteau, Arch. Biochem. Biophys., 427:48-57, 2004 |

[1]Tetraacetate of taxa-4(20),11(12)-dien-5α,9α,10β,13α-tetraol

The cell and test substrate suspension was incubated overnight at 30° C. with mixing (250 rpm). The incubation mixture was then treated for 15 minutes in a sonication bath and extracted twice with 3 ml of hexane:ethyl acetate (4:1 v/v). The organic extract was then dried under $N_2$, the residue dissolved in 100 μl of acetonitrile, and an aliquot was separated by reversed-phase radio-HPLC (250 mm×4.6 mm column of Alltech (Deerfield, Ill.) Econosil $C_{18}$ (5 μm); flow rate of 1 ml/min; with radio-detection of the effluent (Flow-One-Beta Series A-1000, Radiomatic Corp., Meriden, Conn.)). The following gradient was employed: 0-5 minutes at 100% Solvent A (97.99% $H_2O$ with 2% $CH_3CN$ and 0.01% $H_3PO_4$ (v/v)), 5-15 minutes at 0-50% Solvent B (99.99% $CH_3CN$ with 0.01% $H_3PO_4$ (v/v)), 15-55 minutes at 50-100% Solvent B, 55-65 minutes at 100% Solvent B, 65-70 minutes at 0-100% Solvent A, 70-75 minutes at 100% Solvent A. The HPLC eluant was collected in 1 minute fractions and the appropriate fractions containing the radiolabeled product were combined, dried under a stream of $N_2$, and dissolved in the minimum volume of benzene for GC-MS analysis.

GC-MS analyses were performed on a Hewlett-Packard 6890 GC-MSD system using a ZB-5 capillary column (Phenomenex (Torrance, Calif.); 30 m length; 0.25 mm inner diameter; coated with a 0.25 μm film of phenyl (5%) polysiloxane). Cool on-column injection was used, with He flow rate of 0.7 ml/min and a temperature program from 40° C. to 320° C. at 20° C./min. Spectra were recorded at 70 eV.

Radio-HPLC analysis showed that the two taxadiene isomers were most efficiently (almost quantitatively in the case of the 4(5),11(12)-isomer) converted to more polar products. In the case of taxa-4(5),11(12)-diene as substrate, the principal biosynthetic product (>92%) eluted with a retention time identical to that of taxa-4(20),11(12)-dien-5α-ol (Hefner et al., *Chem. Biol.*, 3:479-489, 1996; Rubenstein et al., *J. Label. Compds. Radiopharm.*, 43:481-491, 2000) and the minor product (<50%) eluted with a retention time consistent with that of a taxadien-diol. GC-MS analysis (electron impact ionization) confirmed the major product to possess a retention time and mass spectrum identical to that of authentic taxa-4(20),11(12)-dien-5α-ol (Hefner et al., *Chem. Biol.*, 3:479489, 1996) with characteristic ions at m/z 288 (P+), 273 (P+—

CH$_3$), 270 (P+—H$_2$O) and 255 (P+—H$_2$O—CH$_3$). The minor, more polar product yielded a mass spectrum consistent with that of a taxadien-diol (ions corresponding to the loss of a methyl and two molecules of water from an unobserved parent ion of m/z 304).

In the case of taxa-4(20),11(12)-diene as substrate, the major product (~90%) was again shown, upon radio-HPLC analysis, to possess a retention time identical to that of taxa-4(20),11(12)-dien-5α-ol, and this identification was confirmed as before by GC-MS analysis. The taxadien-diol side product was also observed (~8%), as were a range of other minor metabolites (at ~2% of the product mix) that were also derived from this substrate in the negative control (yeast that expressed β-glucuronidase). These negative controls did not produce taxa-4(20),11(12)-dien-5α-ol or the taxadien-diol from either taxadiene isomer.

A. 13α-Hydroxylase Utilizes 5α-Hydroxylase Product

The order of oxygenation reactions on the taxane (taxadiene) nucleus en route to paclitaxel is not precisely known. However, based on comparison of the structures of the several hundred naturally occurring taxanes (Kingston et al., *The Taxane Diterpenoids*, in Herz et al. (eds.), *Progress in the Chemistry of Organic Natural Products*, Springer-Verlag, New York, Vol. 61, p. 206, 1993; and Baloglu et al., *J. Nat. Prod* 62:1448-1472, 1999), it can be deduced from relative abundances of taxoids with oxygen substitution at each position (Floss et al., *Biosynthesis of Taxol*, in Suffness (ed.), *Taxol: Science and Applications*, CRC Press, Boca Raton, Fla., pp. 191-208, 1995) that oxygens at C5 (carbon numbers shown in Section I, "Taxoid") and C10 are introduced early, followed by oxygenation at C2, C9 and C13. Oxygenations at C7 and C1 of the taxane nucleus are considered to be very late introductions, possibly occurring after oxetane ring formation; however, epoxidation (at C4/C20) and oxetane formation seemingly must precede oxidation of the C9 hydroxyl to a carbonyl (Floss et al., *Biosynthesis of Taxol*, in Suffness (ed.), *Taxol: Science and Applications*, CRC Press, Boca Raton, Fla., pp. 191-208, 1995).

The taxa-4(20),11(12)-dien-5α-ol radiolabeled product of the clone S1 enzyme was isolated by HPLC, and the purified material was fed to yeast that functionally express the previously characterized taxoid 13α-hydroxylase (Jennewein et al., *Proc. Natl. Acad. Sci. USA*, 98:13595-13600, 2001). As discussed above, 13α-hydroxylation of a paclitaxel intermediate is believed to follow 5α-hydroxylation in the paclitaxel biosynthetic pathway (Floss and Mocek, *Taxol: Science and Applications*, CRC Press, Boca Raton, 191-208, 1995; and Croteau et al., *Curr. Top. Plant Physiol.* 15:94-104, 1996). Thus, as expected, taxa-4(20),11(12)-dien-5α-ol was quantitatively converted to taxa-4(20),11(12)-dien-5α,13α-diol by the 13α-hydroxylase.

This Example demonstrates that cytochrome P450 clone S1 encodes a taxoid 5α-hydroxylase, which catalyzes, at least, the first oxygenation step of the paclitaxel biosynthetic pathway.

Example 4

Substrate Binding and Kinetic Analysis of Recombinant 5α-Hydroxylase

This Example demonstrates that the clone S1 hydroxylase binds, at least, taxa-4(20),11(12)-diene and taxa-4(5),11(12)-diene with high affinity, and efficiently catalyzes both taxadiene isomers to the corresponding taxadien-5α-ol.

To prepare sufficient oxygenase enzyme for comparative analysis of substrate binding and kinetic phenomena, in a host less prone to interfering activity and artifact formation, the taxadiene 5α-hydroxylase S1 cDNA clone was transferred to the previously described baculovirus-*Spodoptera fugiperda* (Sf9) expression system (which also coexpresses a *Taxus* cytochrome P450 reductase) (Jennewein et al., *Proc. Natl. Acad. Sci. USA*, 98:13595-13600, 2001).

For construction of the recombinant baculovirus harboring cytochrome P450 clone S1, the S1 ORF was amplified using Pfu DNA polymerase and gene-specific primers containing a BamHI site immediately upstream of the start codon and another containing a NotI site downstream of the stop codon. The gel purified S1 amplicon was subcloned first into the pCR-Blunt™ vector (Invitrogen) and the insert was then excised using the BamHI/NotI restriction sites and ligated into the similarly digested pFastBacI™ vector (Life Technologies, Grand Island, N.Y.). This S1 pFastBacI™ construct was then used to prepare recombinant Bacmid DNA by transforming *Escherichia coli* strain DH10Bac (Life Technologies) carrying the baculovirus genome. As a negative control for this expression system, recombinant baculovirus containing a β-glucuronidase gene, instead of the cytochrome P450 S1 ORF, was used. Baculovirus construction and transfection of Sf9 cells were carried out according to the Life Technologies protocols, and culturing was performed as previously described (Jennewein et al., *Proc. Natl. Acad. Sci. USA*, 98:13595-13600, 2001).

For microsome preparation, Sf9 cells were harvested three days after transfection, washed twice with 50 mM KH$_2$PO$_4$, pH 7.5, containing 9% (w/v) Nacl, twice with 50 mM Hepes, pH 7.5, containing 0.5 mM EDTA, 0.1 mM DTT and 10% (v/v) glycerol, and then lysed by gentle sonication as before in 50 ml of the Hepes buffer system. Cell debris was removed by centrifugation (10,000 g, 20 minutes, 4° C.), and the resulting supernatant was then centrifuged at 28,000 g (20 minutes, 4° C.) and then at 105,000 g (120 minutes, 4° C.) to provide the microsomal membranes which were resuspended in the same Hepes buffer system without EDTA, or other buffer system as noted herein. Protein content was determined by the Bradford method (Bradford, *Anal. Biochem.*, 72:248-254, 1976) using bovine serum albumin as standard.

The CO-difference spectra of microsomes isolated from Sf9 insect cells expressing either the recombinant 5α-hydroxylase or β-glucuronidase gene were obtained as described by Omar and Sato (*J. Biol. Chem.* 239, 2370-2378, 1964) using a Perkin-Elmer Lambda 18 spectrophotometer (Haudenschild et al, *Arch. Biochem. Biophys.*, 379:127-136, 2000). Based on CO-difference spectra, more than 300 pmol cytochrome P450/mg microsomal protein was routinely produced by this Sf9 insect cell system.

Binding spectra for both taxadiene isomers (in the absence of NADPH) were then recorded using the Sf9 cell microsomes enriched in the recombinant 5α-hydroxylase. Substrate binding spectra were obtained as described by Schenkin and Jausson, *Methods Mol. Biol.* (Cytochrome P450 Protocols), 107:25-33, 1998) using a Perkin-Elmer Lambda 18 spectrophotometer (Haudenschild et al., *Arch. Biochem. Biophys.*, 379:127-136, 2000). Substrate binding spectra were recorded with up to 200 pmol of recombinant microsomal cytochrome P450 enzyme (as determined by CO-difference spectral analysis) per cuvette in 100 mM sodium phosphate buffer at pH 7.5. In preparation for binding studies, the taxadiene isomers were each dissolved in DMSO and 1 µl additions to the sample were made to a final concentration of 1.5% (v/v). For data analysis, Spectrum for Windows (Perkin-Elmer Corp., Wellesey, Mass.) and Sigmaplot 7.0 (SPSS Inc., Chicago, Ill.) were employed and experiments were run in triplicate.

Figure 3:
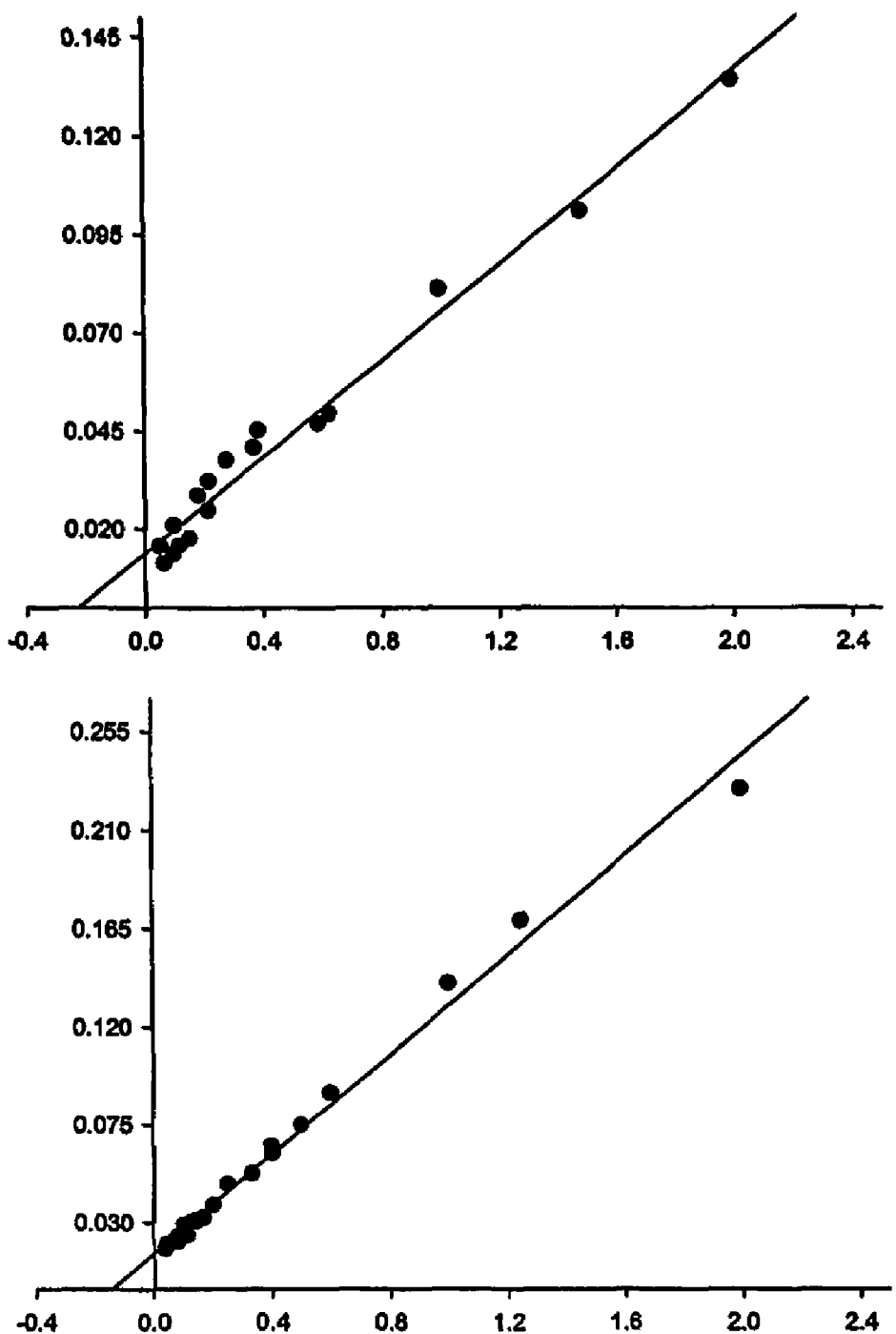
FIG. 3 shows substrate binding spectra of taxadiene isomers. Microsomes from *S. frugiperda* cells enriched with 200 pmol recombinant taxoid 5α-hydroxylase (clone S1) were employed. Taxa-4(20),11(12)-diene was assayed over a concentration range from 0.1 to 10 µM, and a binding constant (Ks) of 4±1 µM was determined (upper graph). Taxa-4(5),11(12)-diene was assayed over a concentration range of 0.1 to 20 µM and a binding constant (Ks) of 6.5±1.5 µM was determined (lower graph).

Evaluation of the substrate binding constant (Ks) over a 100-fold range of substrate concentrations showed Ks to vary somewhat from 3 to 5 µM for taxa-4(20),11(12)-diene and from 5 to 8 µM for taxa-4(5),11(12)-diene (a typical data set at 200 pmol protein concentration is illustrated in FIG. 3). These results indicate that the taxadiene 5α-hydroxylase active site binds, at least, both positional isomers of the olefin substrate with high affinity.

Kinetic constants for both isomers were next evaluated (at a saturating 200 µM concentration of NADPH plus regenerating system; Shimada and Yamazai, *Meth. Mol. Biol.,* 107: 85-93, 1998). The isolated microsomes were resuspended in 50 mM Hepes, pH 7.5, containing 1 mM DTT and 5% (v/v) glycerol, and the 1 ml reactions (~600 µg protein, 50 µM substrate dissolved in DMSO, and the requisite cofactors (e.g., NADPH plus regenerating system) were run as described previously, with the identical protocols for product analysis (Jennewein et al., *Proc. Natl. Acad. Sci. USA,* 98:13595-13600, 2001). DMSO was without influence on the reaction. For kinetic evaluation, following the establishment of linear reaction conditions in protein concentration and time, the response to substrate concentration was plotted by the Michaelis-Menten method (Sigmaplot 7.0) using the calibrated radio-HPLC protocol for product determination Data from three independent experiments were pooled and the line of best fit taken ($R^2$>0.99).

Plotting the lines of best fit ($R^2$>0.99) provided a Km value of 16±3.2 µM, with Vrel of 120, for taxa-4(20),11(12)-diene, and a Km value of 24±2.5 µM, with Vrel of 100, for taxa-4 (5),11(12)-diene (see FIG. 4); the latter Km value compares to a Km value of ~6 µM determined previously for the 4(5), 11(12)-isomer with the native microsome preparations from yew stem tissue (Hefner et al., *Chem. Biol.* 3:479-489, 1996). Comparison of catalytic efficiencies (Vrel/Km) indicates that both taxa-4(20),11(12)-diene and the 4(5),11(12)-isomer are efficiently catalyzed by the recombinant 5α-hydroxylase enzyme.

The taxadien-diol product, which was observed in the intact yeast system fed the taxadiene substrates (see Example 3), was not observed in the baculovirus-*Spodoptera* system. Thus, it is believed that the diol product results from the action of yeast host enzyme(s) upon the taxadienol produced by the recombinant 5α-hydroxylase; this observation was independently verified by feeding control yeast cells the taxadienol product.

This Example and Example 3 demonstrate that the 5α-hydroxylation is a slow step of paclitaxel biosynthesis relative to the downstream oxygenations and acylations. Embodiments of the disclosed oxygenases catalyze 5α-hydroxylation of several taxoids, including, for example, the natural paclitaxel intermediate, taxa-4(5),11(12)-diene. Thus, recombinant expression of the disclosed oxygenase, for example, in *Taxus* plants and cells will increase pathway flux toward paclitaxel to improve production yields of this drug from its natural, and currently the only commercially viable, source.

Example 5

Substrate Utilization by *Taxus* Microsomes

Examples 3 and 4 demonstrate that, at least, two taxadiene isomers are functional substrates of the recombinant clone S1 5α-hydroxylase. *Taxus* cell microsomes contain a structurally uncharacterized 5α-hydroxylase activity (Hefner et al., *Chem. Biol.,* 3:479-489, 1996), which had not been tested previously with the 4(20),11(12)-diene isomer (Hefner et al., *Chem. Biol.,* 3:479-489, 1996). This Example demonstrates that a crude *Taxus* microsome preparation converts both taxa-4(5),11(12)-diene and taxa-4(20),11(12)-diene to the corresponding taxidienols.

Preparation of *Taxus* suspension cell microsomes and assays for microsomal 5α-hydroxylase activity were carried out as previously described (Hefner et al., *Chem. Biol.,* 3:479489, 1996; Lovy Wheeler et al., *Arch. Biochem. Biophys.,* 390:265-278, 2001) with the following modifications: Unelicited *Taxus* media hicksii cells were harvested 14 days after transfer, separated from the media, frozen in liquid $N_2$ and ground to a fine powder with a mortar and pestle, with extraction and microsome preparation as described by Lovy Wheeler et al. (*Arch. Biochem. Biophys.,* 390:265-278, 2001). The previously described radio-HPLC-based assay (Lovy Wheeler et al., *Arch. Biochem. Biophys.,* 390:265-278, 2001) was employed to separate the substrate from taxadien-5α-ol and polyols derived therefrom which were summed as "total product" for the purpose of rate determination.

Following the confirmation of linear reaction conditions in protein concentration and time, kinetic constants were determined for both [20-3H]taxa-4(5),11(12)-diene and [20-3H] taxa-4(20),11(12)-diene with the optimized assay (Hefner et al., *Chem. Biol.,* 3:479-489, 1996). The radio-HPLC-based assay previously described by Lovy Wheeler et al. (*Arch. Biochem. Biophys.,* 390:265-278, 2001) was employed to permit summing of taxadien-polyols derived subsequently from the initially formed taxadienol product generated by this microsomal system that contains all of the downstream cytochrome P450 taxoid oxygenases of the pathway (Lovy Wheeler et al., *Arch. Biochem. Biophys.,* 390:265-278, 2001). Any kinetic isotope effect (KIE) resulting from the C20 deprotonation of [20-$^3$H]taxa-4(5),11(12)-diene was not considered because previous studies with [20-$^2$H$_3$]taxa-4(5),11 (12)-diene (>99 atom % $^2$H) indicated that hydrogen removal from C20 is not rate limiting in the overall hydroxylation reaction (Hefner et al., *Chem. Biol.,* 3:479-489, 1996).

Figure 4:
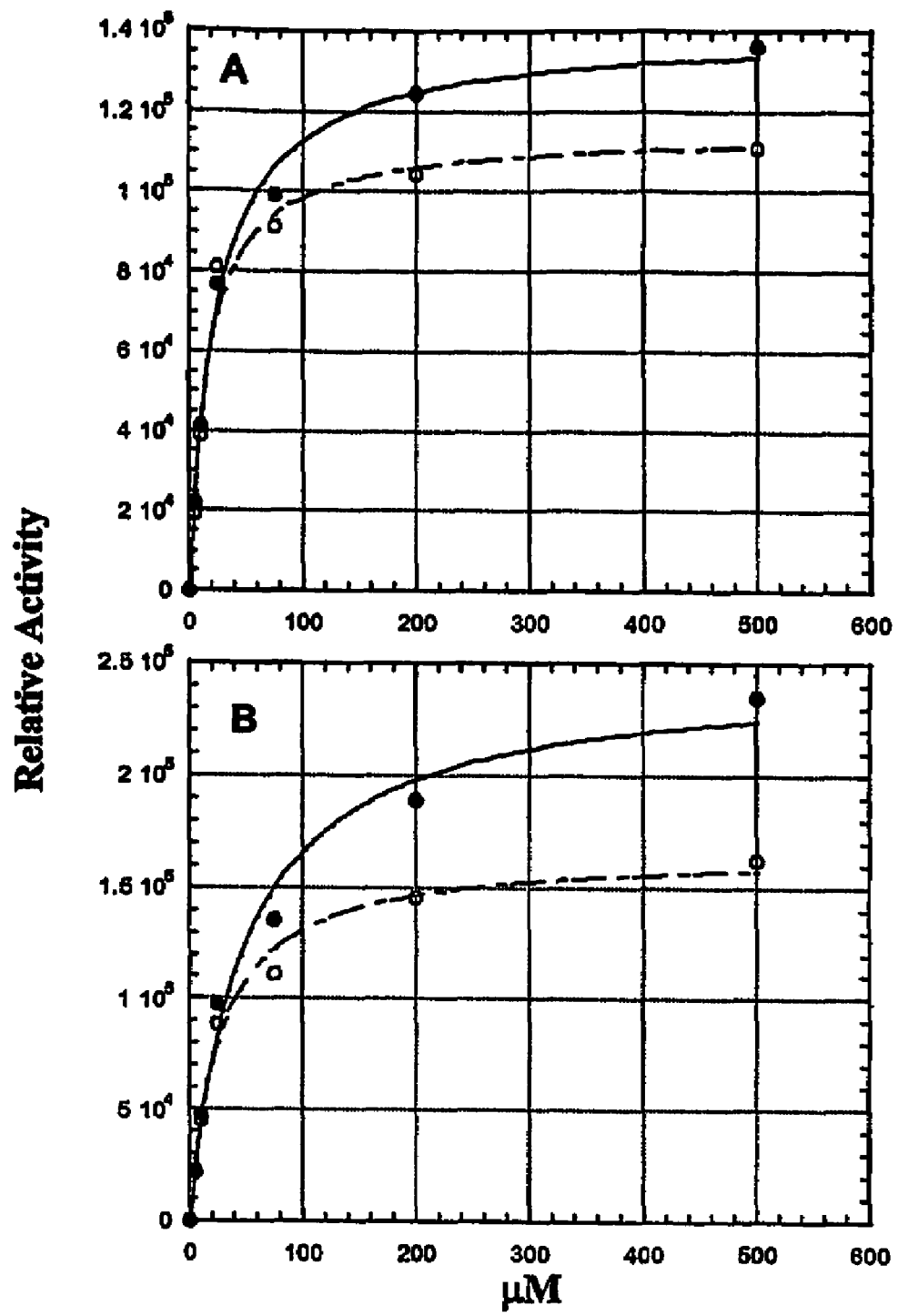
FIG. 4 shows a kinetic evaluation of taxadiene isomers. Taxa-4(20),11(12)-diene (○) and taxa-4(5),11(12)-diene (●) were evaluated with microsomes from *S. formgiperda* cells enriched with 50 pmol recombinant taxoid 5α-hydroxylase (A), and with microsomes from *T. media* suspension cells containing about 50 pmol of total native cytochrome P450 (B). Substrate Concentration range was varied from 1 to 500 µM in all cases. Taxa-4(20),11(12)-diene yielded an average Km value of 21.5 µM with Vrel of 135, and taxa-4(5),11,12-diene yielded an average Km value of 36 µM with Vrel of 100.

By this approach, Michaelis-Menten plotting ($R^2$>0.98 for the lines of best fit) revealed a Km value of 48 µM, and Vrel of 100, for taxa-4(5),11(12)-diene, and a Km value of 27 µM, with Vrel of 150, for taxa-4(20),11(12)-diene (see FIG. 4). Thus, one or more constituents of the crude *Taxus* microsomal protein preparation catalyze the reaction of taxa-4(5),11(12)-diene and taxa-4(20),11(12)-diene to the corresponding taxadienols.

Native and recombinant *Taxus* taxadiene synthase, which is believed to be the first enzyme in the paclitaxel biosynthetic pathway, each produce principally taxa-4(5),11(12)-diene (94%), with very low level co-production of taxa-4(20),11 (12)-diene (4.8%) and verticillene (1.2%), and only trace amounts of taxa-3(4),11(12)-diene (Williams et al., *Arch. Biochem. Biophys.,* 379:137-146, 2000). For this reason, taxa-4(5),11(12)-diene is believed to be the natural substrate of the mediator(s) of the putative next step in the pathway, namely, 5α-hydroxylation. This Example demonstrates that the 5α-hydroxylase activity present in *Taxus* microsomes efficiently utilized two taxadiene substrates with the catalytic efficiency (Vrel/Km) of the presumed unnatural substrate, taxa-4(20),11(12)-diene, being slightly higher than the presumed natural substrate, taxa-4(5),11(12)-diene.

Example 6

In Vivo Substrate of 5α-Hydroxylase

This Example demonstrates that the relaxed substrate specificity of clone S1 oxygenase extends to both naturally occurring substrates and non-naturally occurring substrates.

As discussed in preceding Examples, recombinant 5α-hydroxylase enzyme (clone S1) and 5α-hydroxylase microsomal activity have relaxed substrate specificity and, for example, efficiently utilize taxa-4(20),11(12)-diene as a substrate. *Taxus* taxadiene synthase (native and recombinant enzyme, and allelic variants (Accession No. AY364469 and Accession No. AY364470)) produces very low levels of taxa-4(20),11(12)-diene (4.8%) (Williams et al., *Arch. Biochem. Biophys.*, 379:137-146, 2000). Nonetheless, taxa-4(20),11(12)-diene could be a productive intermediate in vivo if *Taxus* cells expressed a taxadiene isomerase that catalyzed the conversion of taxa-4(20),11(12)-diene to taxa-4(20),11(12)-diene.

Recombinant taxadiene synthase isoforms and taxadiene synthase allelic variants were expressed in *E. coli*. The preparation and assay of the recombinant taxadiene synthase isoforms were conducted by established methods using capillary GC-MS conditions designed to separate taxadiene positional isomers (Williams et al., *Arch. Biochem. Biophys.*, 379:137-146, 2000).

The assay for microsomal taxa-4(5),11(12)-diene isomerase activity (and the reverse isomerization) was carried out under standard cytochrome P450 oxygenase conditions but in the absence of NADPH or $O_2$, or in the presence of inhibitory concentrations of CO, miconazole or clotrimazole (under conditions described previously for which the rate of 5α-hydroxylation is negligible (Hefner et al., *Chem. Biol.*, 3:479489, 1996)). A number of additional, potential cofactors were also tested, including FAD, $FADH_2$, FMN, $FMNH_2$, NAD+, NADH and NADP+ (all at 2.5 mM), as well as $MgCl_2$ (at 5.0 mM). The possibility of pH-dependent isomerization was tested by incubating each isomer (100 μM) in phosphate buffer (pH 4 to 10) for 12 hours at 31° C., with separation of isomers as described previously (Williams et al., *Arch. Biochem. Biophys.*, 379:137-146, 2000).

No isomerization of taxa-4(5),11(12)-diene to the 4(20),11(12)-diene isomer (or vice versa) was observed in *Taxus* cell microsomes (or *Spodoptera* microsomes enriched in the recombinant clone S1 5α-hydroxylase) under standard assay conditions but in the absence of NADPH or in the absence of $O_2$ ($N_2$ atmosphere plus and $O_2$ scavenging system), or in the presence of CO, 100 μM miconazole, or 100 μM clotrimazole (all conditions under which hydroxylation activity is negligible), nor was isomerization observed in boiled controls containing all cofactors and reactants. Similarly, no interconversion of either positional isomer was observed in the presence of magnesium ion, NAD+, NADH or NADP+, or flavin cofactors, at pH values ranging from 4 to 10.

This Example indicates that taxa-4(5),11(12)-diene is not appreciably isomerized to taxa-4(20),11(12)-diene under physiological conditions. The migration of the double bond from the 4(5)- to the 4(20)-position in the process of taxadienol formation may, but need not, be an inherent feature of the cytochrome P450 oxygenase reaction with taxa-4(5),11(12)-diene as substrate.

This Example demonstrates that taxa-4(20),11(12)-diene is an adventitious, yet efficient, substrate for the oxygenase encoded by clone S1.

Example 7

Proposed 5α-Hydroxylase Mechanism of Action

Figure 5:
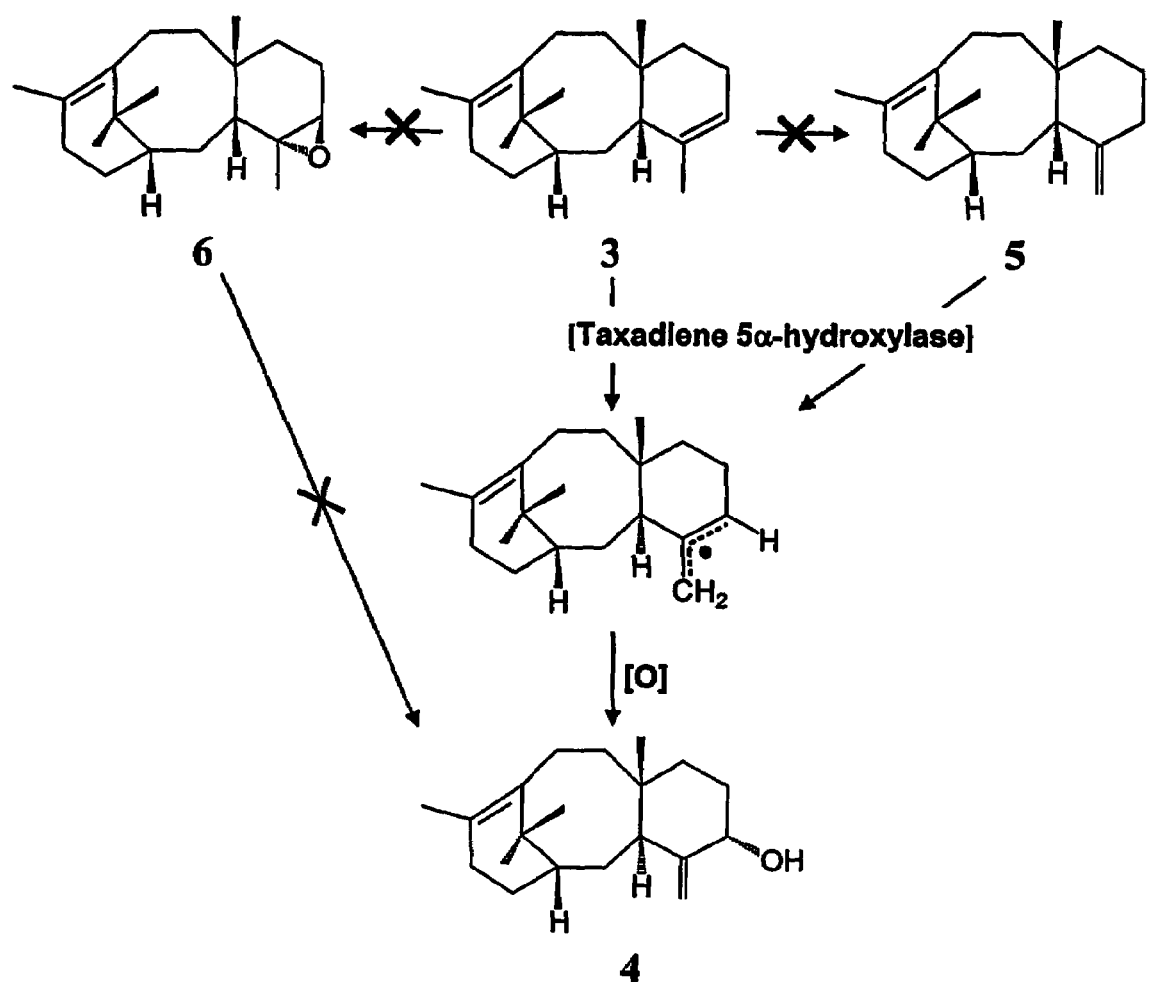
FIG. 5 shows a proposed, but not binding, mechanism for cytochrome P450 taxoid 5α-hydroxylase. This cytochrome P450-mediated conversion of taxa-4(5),11(12)-diene (3) and taxa-4(20),11(12)-diene (5) to taxa-4(20),11(12)-dien-5α-ol (4) is believed to involve hydrogen abstraction from C20 (in 3) or C5 (in 5) to provide a common allylic radical intermediate, followed by oxygen insertion at the 5α-face to yield taxadien-5α-ol (4). Isomerization of 3 to 5 was not observed, nor does the route via epoxide 6 with rearrangement seem likely.

Previous efforts to evaluate the 5α-hydroxylation reaction by the *Taxus* microsomal activity, by search for an epoxide intermediate and through the use of [20-$^2H_3$]taxa-4(5),11(2)-diene to examine a KIE on the deprotonation step, did not elucidate a possible mechanism of action. Two possible mechanisms include, for example, (i) a preliminary conversion of the 4(5)-double bond of taxa-4(5),11(12)-diene to the corresponding 4(5)-epoxide, followed by ring opening and elimination of a proton from the C20 methyl group to yield the allylic alcohol product, or (ii) cytochrome P450-mediated abstraction of hydrogen from the C20 methyl of the substrate to yield the allylic radical to which oxygen is added at C5 (FIG. 5) (Hefner et al., *Chem. Biol.*, 3:479-489, 1996).

Though not bound by any particular mechanism of action, the utilization of the isomeric taxa-4(20),11(12)-diene by the recombinant hydroxylase, with efficiency comparable to that of the putative natural substrate (i.e., taxa-4(5),11(12)-diene), suggests a mechanism involving abstraction of a hydrogen radical from C20 (or C5 in the case of the other isomer), leading to the delocalized allylic radical, followed by oxygen insertion selectively from the 5α-face of this radical intermediate to accomplish the rearrangement. Perhaps the somewhat tighter binding of the 4(20)-isomer is a reflection of the ability of this isomer to more closely mimic the allylic radical intermediate.

Embodiments of this disclosure provide taxoid oxygenase proteins and nucleic acid molecules, and methods of isolating, making, and using these molecules. Specific embodiments relate to taxoid 5-hydroxylase proteins and nucleic acid molecules, including, for example, 5α-hydroxylase proteins and nucleic acid molecules. Further embodiments provide methods for producing paclitaxel, or its intermediates and, in particular, to methods of hydroxylating taxoids at position 5. It will be apparent that the precise details of the compositions and methods described may be varied or modified without departing from the spirit of this disclosure. We claim all such modifications and variations that fall within the scope and spirit of the claims below.

The invention claimed is:

1. An isolated nucleic acid molecule encoding a protein comprising an amino acid sequence having at least 95% sequence identity to SEQ ID NO: 2, wherein the protein has taxoid oxygenase activity.

2. The isolated nucleic acid molecule according to claim 1 comprising the sequence of SEQ ID NO:1.

3. A recombinant nucleic acid molecule, comprising a promoter sequence operably linked to the nucleic acid molecule according to claim 1.

4. A cell transformed with the recombinant nucleic acid molecule according to claim 3.

5. The cell of claim 4, wherein the cell is a plant cell, an insect cell, a bacterium, or a yeast cell.

6. An isolated nucleic acid molecule, comprising a sequence having at least 95% sequence identity with SEQ ID NO: 1, wherein the nucleic acid molecule encodes a protein having taxoid oxygenase activity.

7. A recombinant nucleic acid molecule, comprising a promoter sequence operably linked to the nucleic acid molecule of claim 6.

8. A cell transformed with the recombinant nucleic acid molecule according to claim 7.

9. The cell of claim 8, wherein the cell is a plant cell, an insect cell, a bacterium, or a yeast cell.

10. A method of hydroxylating a substrate, comprising:
contacting a cell comprising the isolated nucleic acid molecule according to claim 1 with a substrate; and allowing the oxygenase encoded by the isolated nucleic acid molecule to hydroxylate the substrate, wherein said substrate is a taxoid.

11. The method of claim 10, wherein the oxygenase hydroxylates position C5 of the taxoid.

12. The method of claim 10, wherein the cell is selected from a plant cell, bacterium cell, insect cell, fungus cell or yeast cell, and the hydroxylation of the substrate occurs in vivo.

13. The method of claim 10, wherein the substrate is an exogenous substrate.

* * * * *

UNITED STATES PATENT AND TRADEMARK OFFICE
CERTIFICATE OF CORRECTION

PATENT NO. : 7,402,417 B2
APPLICATION NO. : 10/565233
DATED : July 22, 2008
INVENTOR(S) : Rodney B. Croteau, Stefan Jennewein and Robert Long It is certified that error appears in the above-identified patent and that said Letters Patent is hereby corrected as shown below:

In the Specification:

At column 5, line 7, "position" should read --position.--.
At column 12, line 36, "recomnbinantly" should read --recombinantly--.
At column 12, line 60, "length Longer" should read --length. Longer--.
At column 12, line 62, "length Primers" should read --length. Primers--.
At column 13, line 16, "length Thus," should read --length. Thus,--.
At column 19, line 20, "*Taxus*species" should read --*Taxus* species--.
At column 32, line 52, "class H." should read --class II.--.
At column 39, line 16, "medium Approximately" should read --medium. Approximately--.
At column 40, line 62, "(<50%)" should read --(<5%)--.
At column 40, line 66, "3:479489," should read --3:479-489,--.
At column 44, line 21, "[20-3H]taxa-4(5),11(12)-diene" should read --[20-$^3$H]taxa-4(5),11(12)-diene--.
At column 44, lines 21-22, "[20-3H]taxa-4(20),11(12)-diene" should read --[20-$^3$H]taxa-4(20),11(12)-diene--.
At column 45, line 28, "3:479489," should read --3:479-489,--.

Signed and Sealed this
Nineteenth Day of May, 2015

Michelle K. Lee
*Director of the United States Patent and Trademark Office*

SEQUENCE LISTING

```
<160> NUMBER OF SEQ ID NOS: 41

<210> SEQ ID NO 1
<211> LENGTH: 1688
<212> TYPE: DNA
<213> ORGANISM: Taxus cuspidata
<220> FEATURE:
<221> NAME/KEY: CDS
<222> LOCATION: (40)..(1548)
<223> OTHER INFORMATION: coding sequence

<400> SEQUENCE: 1
```

-continued

```
cggcaccagg tttctgctc ctgcttttct tcttccaaa atg gac gcc ctg tat        54
                                          Met Asp Ala Leu Tyr
                                            1               5 aag agc aca gtt gca aaa ttt aat gag gtc aca cag ctg gac tgt tcc       102
Lys Ser Thr Val Ala Lys Phe Asn Glu Val Thr Gln Leu Asp Cys Ser
             10                  15                  20 act gaa tct ttt tcc att gcc ctc tca gct att gct ggt att ctt ctg       150
Thr Glu Ser Phe Ser Ile Ala Leu Ser Ala Ile Ala Gly Ile Leu Leu
         25                  30                  35 ctt ctc ctg ctc ttc cgt tct aaa cgc cac tcc tcc ctt aaa ctt cct       198
Leu Leu Leu Leu Phe Arg Ser Lys Arg His Ser Ser Leu Lys Leu Pro
     40                  45                  50 cct ggg aaa tta ggc atc cct ttc att ggc gag tcg ttt atc ttc ctg       246
Pro Gly Lys Leu Gly Ile Pro Phe Ile Gly Glu Ser Phe Ile Phe Leu
 55                  60                  65 agg gct ctt cga tcg aac tcg ctg gag caa ttt ttt gac gag aga gtg       294
Arg Ala Leu Arg Ser Asn Ser Leu Glu Gln Phe Phe Asp Glu Arg Val
 70                  75                  80                  85 aag aaa ttc ggc ctc gtg ttc aag acc tcc ttg att ggg cat ccc aca       342
Lys Lys Phe Gly Leu Val Phe Lys Thr Ser Leu Ile Gly His Pro Thr
                 90                  95                 100 gta gta ctc tgc ggc cct gcg gga aac cgg ctt att ctg tcc aac gag       390
Val Val Leu Cys Gly Pro Ala Gly Asn Arg Leu Ile Leu Ser Asn Glu
             105                 110                 115 gag aag ctg gtg cag atg tcg tgg ccc gct caa ttt atg aag ctc atg       438
Glu Lys Leu Val Gln Met Ser Trp Pro Ala Gln Phe Met Lys Leu Met
         120                 125                 130 ggg gag aat tcc gtt gcc acc agg agg ggt gaa gac cat ata gtt atg       486
Gly Glu Asn Ser Val Ala Thr Arg Arg Gly Glu Asp His Ile Val Met
     135                 140                 145 cgc tct gct ctt gca ggt ttt ttc ggc cct ggt gcg ctg cag agt tac       534
Arg Ser Ala Leu Ala Gly Phe Phe Gly Pro Gly Ala Leu Gln Ser Tyr
150                 155                 160                 165 att ggt aaa atg aat aca gag atc cag agt cat atc aac gaa aaa tgg       582
Ile Gly Lys Met Asn Thr Glu Ile Gln Ser His Ile Asn Glu Lys Trp
                 170                 175                 180 aag gga aaa gat gag gtg aat gta ctt cct ttg gta aga gag ctc gtc       630
Lys Gly Lys Asp Glu Val Asn Val Leu Pro Leu Val Arg Glu Leu Val
             185                 190                 195 ttc aac att tcg gcc atc ttg ttt ttc aac ata tat gat aag cag gaa       678
Phe Asn Ile Ser Ala Ile Leu Phe Phe Asn Ile Tyr Asp Lys Gln Glu
         200                 205                 210 cag gat cgt ctg cat aag ctt ttg gaa act att ctg gtc gga agt ttt       726
Gln Asp Arg Leu His Lys Leu Leu Glu Thr Ile Leu Val Gly Ser Phe
     215                 220                 225 gct ctt ccg att gac ttg ccc gga ttt ggt ttc cat aga gca ctc cag       774
Ala Leu Pro Ile Asp Leu Pro Gly Phe Gly Phe His Arg Ala Leu Gln
230                 235                 240                 245 gga cgg gcc aag ctc aac aaa att atg ctg tct tta att aaa aag aga       822
Gly Arg Ala Lys Leu Asn Lys Ile Met Leu Ser Leu Ile Lys Lys Arg
                 250                 255                 260 aaa gaa gat ctg cag tct gga tcg gca aca gcc acg cag gat ctg ctc       870
Lys Glu Asp Leu Gln Ser Gly Ser Ala Thr Ala Thr Gln Asp Leu Leu
             265                 270                 275 tct gtt ttg ctc act ttc aga gat gac aaa ggg act cca ctc acc aat       918
Ser Val Leu Leu Thr Phe Arg Asp Asp Lys Gly Thr Pro Leu Thr Asn
         280                 285                 290 gat gag ata ctc gac aac ttt tct tct ctg ctc cat gcc tcc tat gac       966
Asp Glu Ile Leu Asp Asn Phe Ser Ser Leu Leu His Ala Ser Tyr Asp
```

```
                     295                     300                     305
acc acc act tcg cca atg gct ttg att ttc aag ctc ttg tct tcc aat          1014
Thr Thr Thr Ser Pro Met Ala Leu Ile Phe Lys Leu Leu Ser Ser Asn
310                 315                     320                 325 cca gaa tgc tat caa aaa gta gtt caa gag caa ttg gag ata ctt tcc          1062
Pro Glu Cys Tyr Gln Lys Val Val Gln Glu Gln Leu Glu Ile Leu Ser
                    330                     335                 340 aac aaa gag gag ggc gaa gaa atc aca tgg aag gat ctc aaa gcc atg          1110
Asn Lys Glu Glu Gly Glu Glu Ile Thr Trp Lys Asp Leu Lys Ala Met
                345                     350                 355 aaa tac aca tgg caa gta gct cag gaa acg ctg cgg atg ttt cct cca          1158
Lys Tyr Thr Trp Gln Val Ala Gln Glu Thr Leu Arg Met Phe Pro Pro
            360                     365                 370 gtt ttc gga aca ttt cgc aag gcc atc act gac att cag tat gat ggt          1206
Val Phe Gly Thr Phe Arg Lys Ala Ile Thr Asp Ile Gln Tyr Asp Gly
        375                     380                 385 tac aca att cca aaa ggg tgg aag ctg ttg tgg aca act tac agt aca          1254
Tyr Thr Ile Pro Lys Gly Trp Lys Leu Leu Trp Thr Thr Tyr Ser Thr
390                 395                     400                 405 cat ccc aag gac ttg tat ttc aat gaa cca gag aaa ttc atg cct tca          1302
His Pro Lys Asp Leu Tyr Phe Asn Glu Pro Glu Lys Phe Met Pro Ser
                    410                     415                 420 aga ttc gat cag gaa gga aag cat gta gct cct tac aca ttt ttg ccc          1350
Arg Phe Asp Gln Glu Gly Lys His Val Ala Pro Tyr Thr Phe Leu Pro
                425                     430                 435 ttc ggt gga ggc caa cgg tca tgt gtg gga tgg gaa ttt tca aag atg          1398
Phe Gly Gly Gly Gln Arg Ser Cys Val Gly Trp Glu Phe Ser Lys Met
            440                     445                 450 gag ata tta cta ttc gtt cat cat ttt gtc aaa act ttt agc agc tac          1446
Glu Ile Leu Leu Phe Val His His Phe Val Lys Thr Phe Ser Ser Tyr
        455                     460                 465 acc cca gtt gat ccc gac gaa aaa ata tca ggg gat cca ctc cct cct          1494
Thr Pro Val Asp Pro Asp Glu Lys Ile Ser Gly Asp Pro Leu Pro Pro
470                 475                     480                 485 ctt cct tcc aag gga ttt tcc att aaa ctg ttt ccc gag acc ata gtc          1542
Leu Pro Ser Lys Gly Phe Ser Ile Lys Leu Phe Pro Glu Thr Ile Val
                    490                     495                 500 aat tga aggagaaaac cacagtgcag aactgctatt cttgaatcct cgctcaagaa           1598
Asn taatacaaac atgcatcacc aacaatgttt atgcactcaa tgcaaattaa cagtgtgtca        1658
gcattgacag tcaaaaaaaa aaaaaaaaaa                                         1688

<210> SEQ ID NO 2
<211> LENGTH: 502
<212> TYPE: PRT
<213> ORGANISM: Taxus cuspidata

<400> SEQUENCE: 2

Met Asp Ala Leu Tyr Lys Ser Thr Val Ala Lys Phe Asn Glu Val Thr
1               5                   10                  15

Gln Leu Asp Cys Ser Thr Glu Ser Phe Ser Ile Ala Leu Ser Ala Ile
                20                  25                  30

Ala Gly Ile Leu Leu Leu Leu Leu Phe Arg Ser Lys Arg His Ser
            35                  40                  45

Ser Leu Lys Leu Pro Pro Gly Lys Leu Gly Ile Pro Phe Ile Gly Glu
        50                  55                  60

Ser Phe Ile Phe Leu Arg Ala Leu Arg Ser Asn Ser Leu Glu Gln Phe
65                  70                  75                  80
```

-continued

```
Phe Asp Glu Arg Val Lys Lys Phe Gly Leu Val Phe Lys Thr Ser Leu
                 85                  90                  95
Ile Gly His Pro Thr Val Val Leu Cys Gly Pro Ala Gly Asn Arg Leu
                100                 105                 110
Ile Leu Ser Asn Glu Glu Lys Leu Val Gln Met Ser Trp Pro Ala Gln
                115                 120                 125
Phe Met Lys Leu Met Gly Glu Asn Ser Val Ala Thr Arg Arg Gly Glu
                130                 135                 140
Asp His Ile Val Met Arg Ser Ala Leu Ala Gly Phe Phe Gly Pro Gly
145                 150                 155                 160
Ala Leu Gln Ser Tyr Ile Gly Lys Met Asn Thr Glu Ile Gln Ser His
                165                 170                 175
Ile Asn Glu Lys Trp Lys Gly Lys Asp Glu Val Asn Val Leu Pro Leu
                180                 185                 190
Val Arg Glu Leu Val Phe Asn Ile Ser Ala Ile Leu Phe Phe Asn Ile
                195                 200                 205
Tyr Asp Lys Gln Glu Gln Asp Arg Leu His Lys Leu Leu Glu Thr Ile
                210                 215                 220
Leu Val Gly Ser Phe Ala Leu Pro Ile Asp Leu Pro Gly Phe Gly Phe
225                 230                 235                 240
His Arg Ala Leu Gln Gly Arg Ala Lys Leu Asn Lys Ile Met Leu Ser
                245                 250                 255
Leu Ile Lys Lys Arg Lys Glu Asp Leu Gln Ser Gly Ser Ala Thr Ala
                260                 265                 270
Thr Gln Asp Leu Leu Ser Val Leu Leu Thr Phe Arg Asp Asp Lys Gly
                275                 280                 285
Thr Pro Leu Thr Asn Asp Glu Ile Leu Asp Asn Phe Ser Ser Leu Leu
                290                 295                 300
His Ala Ser Tyr Asp Thr Thr Thr Ser Pro Met Ala Leu Ile Phe Lys
305                 310                 315                 320
Leu Leu Ser Ser Asn Pro Glu Cys Tyr Gln Lys Val Val Gln Glu Gln
                325                 330                 335
Leu Glu Ile Leu Ser Asn Lys Glu Glu Gly Glu Glu Ile Thr Trp Lys
                340                 345                 350
Asp Leu Lys Ala Met Lys Tyr Thr Trp Gln Val Ala Gln Glu Thr Leu
                355                 360                 365
Arg Met Phe Pro Pro Val Phe Gly Thr Phe Arg Lys Ala Ile Thr Asp
                370                 375                 380
Ile Gln Tyr Asp Gly Tyr Thr Ile Pro Lys Gly Trp Lys Leu Leu Trp
385                 390                 395                 400
Thr Thr Tyr Ser Thr His Pro Lys Asp Leu Tyr Phe Asn Glu Pro Glu
                405                 410                 415
Lys Phe Met Pro Ser Arg Phe Asp Gln Glu Gly Lys His Val Ala Pro
                420                 425                 430
Tyr Thr Phe Leu Pro Phe Gly Gly Gly Gln Arg Ser Cys Val Gly Trp
                435                 440                 445
Glu Phe Ser Lys Met Glu Ile Leu Leu Phe Val His His Phe Val Lys
                450                 455                 460
Thr Phe Ser Ser Tyr Thr Pro Val Asp Pro Asp Glu Lys Ile Ser Gly
465                 470                 475                 480
Asp Pro Leu Pro Pro Leu Pro Ser Lys Gly Phe Ser Ile Lys Leu Phe
                485                 490                 495
```

Pro Glu Thr Ile Val Asn
            500

<210> SEQ ID NO 3
<211> LENGTH: 1455
<212> TYPE: DNA
<213> ORGANISM: Taxus cuspidata

<400> SEQUENCE: 3

```
atggatacct tcattcagca cgagtcttcc ccacttcttc tttctcttac tctcgctgtt      60
attcttggca caattcttct tttgatatta agtggtaaac agtacagatc ttctcgtaaa     120
cttccccctg gaaacatggg cttccctctc attggggaga ctatagcact tatatcagat     180
acacctcgga agtttatcga cgacagagtg aagaaattcg gcctggtttt caagacttcg     240
ctaattggtc atcccgcagt tgtaatatgc ggctcctccg caaaccgttt cctcctctcc     300
aacgaggaaa agctggtgcg gatgtctttg cccaacgcag tactgaaact cttggggcag     360
gattgcgtta tggggaaaac cggagtggag catgggattg tacgtaccgc actagcccgc     420
gccttgggcc cccaggcgtt gcagaattat gtggccaaaa tgagttcaga gatcgaacac     480
catatcaacc aaaaatggaa ggggaaagat gaggtgaagg tgcttcctct gataagaagc     540
ctcgtcttct ccatttcaac cagcttgttt tcggtataa cgatgagca ccaacgaaag      600
cgacttcatc atcttttgga aactgtagct atgggacttg tgagtattcc cctagacttt     660
ccaggaactc gttttcgtaa agcactttac gcgcggtcga agctcgatga aattatgtct     720
tctgtaatag aaaggagaag aagcgatctt cgttcaggag cagcttcaag cgaccaagat     780
ctactgtcgg tgttggtcac cttcaaagat gaaagaggga attcattcgc agacaaggag     840
atactggata acttctcttt tctacttcac gccttatacg acaccacaat ttcaccactc     900
accttgatat ttaagctgct ctcctctagt cctgaatgct atgagaatat agctcaagag     960
cagctggaaa tacttggcaa taaaaaggat agagaggaaa tcagctggaa ggatctgaag    1020
gatatgaaat atacatggca agcagttcag gaaactttga ggatgttccc tccagtttat    1080
ggatatattc gcgaggcttt gacagatatt gactatgatg ctatacaat accaaaagga     1140
tggagaatat tatgttcacc tcatactacg catagtaaag aggagtattt cgatgagccg    1200
gaagaattca ccttcaag attcgaggat caaggaaggc atgtggctcc ttacacattc     1260
ataccatttg gaggaggcct gcgcatctgt gcaggctggg aatttgcaaa gatggagata    1320
ttactgttta tgcatcattt tgttaaaaact ttcagtcact tcattccagt tgaccccaac    1380
gaaaagattt cgagagatcc actgcctccc atccctgtca aggattttc cataaagcct     1440
tttcctagat cataa                                                     1455
```

<210> SEQ ID NO 4
<211> LENGTH: 484
<212> TYPE: PRT
<213> ORGANISM: Taxus cuspidata

<400> SEQUENCE: 4

```
Met Asp Thr Phe Ile Gln His Glu Ser Ser Pro Leu Leu Leu Ser Leu
1               5                   10                  15

Thr Leu Ala Val Ile Leu Gly Thr Ile Leu Leu Ile Leu Ser Gly
            20                  25                  30

Lys Gln Tyr Arg Ser Ser Arg Lys Leu Pro Pro Gly Asn Met Gly Phe
        35                  40                  45

Pro Leu Ile Gly Glu Thr Ile Ala Leu Ile Ser Asp Thr Pro Arg Lys
```

-continued

```
            50                  55                  60
Phe Ile Asp Asp Arg Val Lys Lys Phe Gly Leu Val Phe Lys Thr Ser
 65                  70                  75                  80

Leu Ile Gly His Pro Ala Val Ile Cys Gly Ser Ser Ala Asn Arg
                 85                  90                  95

Phe Leu Leu Ser Asn Glu Glu Lys Leu Val Arg Met Ser Leu Pro Asn
                100                 105                 110

Ala Val Leu Lys Leu Leu Gly Gln Asp Cys Val Met Gly Lys Thr Gly
                115                 120                 125

Val Glu His Gly Ile Val Arg Thr Ala Leu Ala Arg Ala Leu Gly Pro
130                 135                 140

Gln Ala Leu Gln Asn Tyr Val Ala Lys Met Ser Ser Glu Ile Glu His
145                 150                 155                 160

His Ile Asn Gln Lys Trp Lys Gly Lys Asp Glu Val Lys Val Leu Pro
                165                 170                 175

Leu Ile Arg Ser Leu Val Phe Ser Ile Ser Thr Ser Leu Phe Phe Gly
                180                 185                 190

Ile Asn Asp Glu His Gln Gln Lys Arg Leu His His Leu Leu Glu Thr
                195                 200                 205

Val Ala Met Gly Leu Val Ser Ile Pro Leu Asp Phe Pro Gly Thr Arg
210                 215                 220

Phe Arg Lys Ala Leu Tyr Ala Arg Ser Lys Leu Asp Glu Ile Met Ser
225                 230                 235                 240

Ser Val Ile Glu Arg Arg Ser Asp Leu Arg Ser Gly Ala Ala Ser
                245                 250                 255

Ser Asp Gln Asp Leu Leu Ser Val Leu Val Thr Phe Lys Asp Glu Arg
                260                 265                 270

Gly Asn Ser Phe Ala Asp Lys Glu Ile Leu Asp Asn Phe Ser Phe Leu
                275                 280                 285

Leu His Ala Leu Tyr Asp Thr Thr Ile Ser Pro Leu Thr Leu Ile Phe
                290                 295                 300

Lys Leu Leu Ser Ser Pro Glu Cys Tyr Glu Asn Ile Ala Gln Glu
305                 310                 315                 320

Gln Leu Glu Ile Leu Gly Asn Lys Lys Asp Arg Glu Glu Ile Ser Trp
                325                 330                 335

Lys Asp Leu Lys Asp Met Lys Tyr Thr Trp Gln Ala Val Gln Glu Thr
                340                 345                 350

Leu Arg Met Phe Pro Pro Val Tyr Gly Tyr Ile Arg Glu Ala Leu Thr
                355                 360                 365

Asp Ile Asp Tyr Asp Gly Tyr Thr Ile Pro Lys Gly Trp Arg Ile Leu
370                 375                 380

Cys Ser Pro His Thr Thr His Ser Lys Glu Gly Tyr Phe Asp Glu Pro
385                 390                 395                 400

Glu Glu Phe Arg Pro Ser Arg Phe Glu Asp Gln Gly Arg His Val Ala
                405                 410                 415

Pro Tyr Thr Phe Ile Pro Phe Gly Gly Gly Leu Arg Ile Cys Ala Gly
                420                 425                 430

Trp Glu Phe Ala Lys Met Glu Ile Leu Leu Phe Met His His Phe Val
                435                 440                 445

Lys Thr Phe Ser His Phe Ile Pro Val Asp Pro Asn Glu Lys Ile Ser
                450                 455                 460

Arg Asp Pro Leu Pro Pro Ile Pro Val Lys Gly Phe Ser Ile Lys Pro
465                 470                 475                 480
```

Phe Pro Arg Ser

<210> SEQ ID NO 5
<211> LENGTH: 1455
<212> TYPE: DNA
<213> ORGANISM: Taxus cuspidata

<400> SEQUENCE: 5

```
atgcttatcg aaatggatac cttcgttcag ctcgagtctt ccctgttct tctttccctt      60
accctcacac ttattcttct ttttatattc tgtagtaaac aatacagatc ctctcttaaa    120
cttcccctg gaaacatggg cttccctctc attggggaga cgatagcact ggcatcacag     180
acacctgata aattttttcgg cgatagaatg aagaaattcg gcaaggtttt caagacttcg    240
ttaattgggc atcccacaat tgtgctctgc ggttcctccg gaaaccgttt tctcctctcc    300
aacgaggaaa aactggtgcg gatgtttccg cccaactcat ccagcaaact cctggggcag    360
gattctgttc tggggaaaat aggagaggag catcggattg tacgtaccgc actagcccgc    420
tgtttgggcc ccaagcgct gcagaattac gtgtccaaaa tgagttcaga gatccaacgt     480
catatcaacc aaaatggaa gggaaaaggt gaagtgaaga tgcttcctct gataagaagc    540
cttgtcttct ccatcgcaac cagcttattt tttggtatta ccgatgagca acaacaagaa    600
cgacttcatc atcttctgga aacagttgtt acgggacttt tgtgtattcc gctcgacttt    660
ccaggaacta catttcgtaa agcacttcac gcgcggtcga agctcgatga gattatgtct    720
tctgtaatag aaaggagaag aaacgatctg cgtttaggcg cagcttcaag cgaccaagat    780
ctattgtcgg tgttgctcac cttcaaagat gaaagaggga atccattcgc tgacaaggag    840
atcctggata acttctcttt tctacttcat gccttatacg acaccacaat tcaccactc    900
acgttggtat ttaagctggt gtcctccaat cctgaatgct acgaaaatat agctcaagag    960
caattggaaa ttcttcgcaa taaaaaggat ggagaagata tcagctgggc ggatctgaag   1020
gatatgaaat atacgtggca agcagttcag gaaaccttga ggatgtgtcc tccagtttac   1080
ggaaattttc gcaaggcttt gacagatatt cattatgatg ctatacaat cccaaaagga    1140
tggaggattt tatgttcacc ttatactaca catagtaaag aggagtattt tgacgacccg   1200
gagaaattca gaccttcaag attcgaagag caaggaaggg atgtggctcc ttacacattc   1260
ataccattcg gaggaggcct gcgcatctgt ccaggccggg aatttgcgaa gatggagata   1320
ttagtgttta tgcatcattt tgttaaagct ttcagcagct tcattccagt tgaccctaac   1380
gaaaaaattt caacagatcc gcttccttcc atccctgtca atggattttc cataaacctt   1440
gttcccagat cctaa                                                      1455
```

<210> SEQ ID NO 6
<211> LENGTH: 484
<212> TYPE: PRT
<213> ORGANISM: Taxus cuspidata

<400> SEQUENCE: 6

```
Met Leu Ile Glu Met Asp Thr Phe Val Gln Leu Glu Ser Ser Pro Val
1               5                   10                  15

Leu Leu Ser Leu Thr Leu Thr Leu Ile Leu Leu Phe Ile Phe Cys Ser
            20                  25                  30

Lys Gln Tyr Arg Ser Ser Leu Lys Leu Pro Pro Gly Asn Met Gly Phe
        35                  40                  45

Pro Leu Ile Gly Glu Thr Ile Ala Leu Ala Ser Gln Thr Pro Asp Lys
```

```
                50                      55                     60
Phe Phe Gly Asp Arg Met Lys Lys Phe Gly Lys Val Phe Lys Thr Ser
 65                      70                     75                     80

Leu Ile Gly His Pro Thr Ile Val Leu Cys Gly Ser Ser Gly Asn Arg
                         85                     90                     95

Phe Leu Leu Ser Asn Glu Glu Lys Leu Val Arg Met Phe Pro Pro Asn
                        100                    105                    110

Ser Ser Ser Lys Leu Leu Gly Gln Asp Ser Val Leu Gly Lys Ile Gly
                        115                    120                    125

Glu Glu His Arg Ile Val Arg Thr Ala Leu Ala Arg Cys Leu Gly Pro
                        130                    135                    140

Gln Ala Leu Gln Asn Tyr Val Ser Lys Met Ser Ser Glu Ile Gln Arg
145                     150                    155                    160

His Ile Asn Gln Lys Trp Lys Gly Lys Gly Glu Val Lys Met Leu Pro
                        165                    170                    175

Leu Ile Arg Ser Leu Val Phe Ser Ile Ala Thr Ser Leu Phe Phe Gly
                        180                    185                    190

Ile Thr Asp Glu Gln Gln Gln Glu Arg Leu His His Leu Leu Glu Thr
                        195                    200                    205

Val Val Thr Gly Leu Leu Cys Ile Pro Leu Asp Phe Pro Gly Thr Thr
                        210                    215                    220

Phe Arg Lys Ala Leu His Ala Arg Ser Lys Leu Asp Glu Ile Met Ser
225                     230                    235                    240

Ser Val Ile Glu Arg Arg Asn Asp Leu Arg Leu Gly Ala Ala Ser
                        245                    250                    255

Ser Asp Gln Asp Leu Leu Ser Val Leu Leu Thr Phe Lys Asp Glu Arg
                        260                    265                    270

Gly Asn Pro Phe Ala Asp Lys Glu Ile Leu Asp Asn Phe Ser Phe Leu
                        275                    280                    285

Leu His Ala Leu Tyr Asp Thr Thr Ile Ser Pro Leu Thr Leu Val Phe
                        290                    295                    300

Lys Leu Val Ser Ser Asn Pro Glu Cys Tyr Glu Asn Ile Ala Gln Glu
305                     310                    315                    320

Gln Leu Glu Ile Leu Arg Asn Lys Lys Asp Gly Glu Asp Ile Ser Trp
                        325                    330                    335

Ala Asp Leu Lys Asp Met Lys Tyr Thr Trp Gln Ala Val Gln Glu Thr
                        340                    345                    350

Leu Arg Met Cys Pro Pro Val Tyr Gly Asn Phe Arg Lys Ala Leu Thr
                        355                    360                    365

Asp Ile His Tyr Asp Gly Tyr Thr Ile Pro Lys Gly Trp Arg Ile Leu
                        370                    375                    380

Cys Ser Pro Tyr Thr Thr His Ser Lys Glu Glu Tyr Phe Asp Asp Pro
385                     390                    395                    400

Glu Lys Phe Arg Pro Ser Arg Phe Glu Glu Gln Gly Arg Asp Val Ala
                        405                    410                    415

Pro Tyr Thr Phe Ile Pro Phe Gly Gly Gly Leu Arg Ile Cys Pro Gly
                        420                    425                    430

Arg Glu Phe Ala Lys Met Glu Ile Leu Val Phe Met His His Phe Val
                        435                    440                    445

Lys Ala Phe Ser Ser Phe Ile Pro Val Asp Pro Asn Glu Lys Ile Ser
                        450                    455                    460

Thr Asp Pro Leu Pro Ser Ile Pro Val Asn Gly Phe Ser Ile Asn Leu
465                     470                    475                    480
```

Val Pro Arg Ser

<210> SEQ ID NO 7
<211> LENGTH: 1503
<212> TYPE: DNA
<213> ORGANISM: Taxus cuspidata

<400> SEQUENCE: 7

```
atggatgccc tttctcttgt aaacagcaca gttgcaaaat taatgaggt aacgcagcta      60
caggcttccc ctgctattct gtccactgcc ctcactgcta ttgcaggcat tattgtgctc    120
ctcgtcatca cttctaaacg ccgttcctct cttaaacttc ctcctggaaa actaggcctc    180
cctttcattg gcgagacttt agagttcgtg aaggctcttc gatcagacac acttcgacaa    240
tttgtggagg aaagggaggg gaaatttgga cgtgtgttca agacttcatt gcttgggaag    300
cccactgtaa tactctgcgg ccctgcggga accgcttag ttctttccaa cgaggaaaaa    360
ctgttgcacg tgtcgtggtc cgcccaaatt gccagaatcc tgggtctcaa ttctgttgca    420
gtgaaaaggg gagatgatca ccgcgttctg cgtgtcgcac tagcaggttt tttgggctct    480
gcagggctac agctttacat aggtaaaatg agtgcactta tcagaaatca tatcaatgaa    540
aaatggaagg gaaagatga agtgaatgta ctgagtttgg taagatct tgtcatggac    600
aattcagcta tcttgttttt caatatatac gataaagagc gaaagcaaca actgcatgaa    660
atattgaaaa tcattcttgc ctcacatttc ggcatacctt taaacattcc cggatttctg    720
tatcgcaaag cactcaaggg gagcttgaag cggaaaaaaa ttctctccgc tttactggaa    780
aagagaaaag acgaactgcg ctcaagatta gcgtctagca atcaagatct tctctctgtt    840
ttgctcagct tcagagatga aagagggaaa ccactgagcg acgaggcagt cttagacaac    900
tgttttgcaa tgctggatgc ctcctatgac accaccactt cacaaatgac tctgatttta    960
aagatgttgt cttccaatcc agaatgcttt gaaaaagtag ttcaagagca attggagata   1020
gcgtcaaata aaaaggaggg agaagaaatc acaatgaagg atatcaaagc catgaaatac   1080
acatggcaag tgctccagga aagtctacgg atgctttctc cagtatttgg aacacttcgt   1140
aagaccatga atgacattaa tcacgatggt tacacaattc caaaggatg caggttgta   1200
tggacaactt attctacaca tcagaaagac atatatttca agcagccaga taattcatg   1260
ccttcgagat cgaagagga agatgggcat ttggatgctt atacattcgt accatttgga   1320
ggaggacggc ggacatgtcc aggatgggaa tacgcaaaag tggaaatatt actgttcctc   1380
catcattttg tgaaagcatt cagtggttac accccaactg accctcatga aaggatttgt   1440
gggtatccag tccctcttgt ccctgtcaag ggatttccaa taaaacttat cgccagatcc   1500
tga                                                                 1503
```

<210> SEQ ID NO 8
<211> LENGTH: 500
<212> TYPE: PRT
<213> ORGANISM: Taxus cuspidata

<400> SEQUENCE: 8

Met Asp Ala Leu Ser Leu Val Asn Ser Thr Val Ala Lys Phe Asn Glu
1               5                   10                  15

Val Thr Gln Leu Gln Ala Ser Pro Ala Ile Leu Ser Thr Ala Leu Thr
            20                  25                  30

Ala Ile Ala Gly Ile Ile Val Leu Leu Val Ile Thr Ser Lys Arg Arg
        35                  40                  45

```
Ser Ser Leu Lys Leu Pro Pro Gly Lys Leu Gly Leu Pro Phe Ile Gly
     50                  55                  60

Glu Thr Leu Glu Phe Val Lys Ala Leu Arg Ser Asp Thr Leu Arg Gln
 65                  70                  75                  80

Phe Val Glu Glu Arg Glu Gly Lys Phe Gly Arg Val Phe Lys Thr Ser
             85                  90                  95

Leu Leu Gly Lys Pro Thr Val Ile Leu Cys Gly Pro Ala Gly Asn Arg
            100                 105                 110

Leu Val Leu Ser Asn Glu Glu Lys Leu Leu His Val Ser Trp Ser Ala
            115                 120                 125

Gln Ile Ala Arg Ile Leu Gly Leu Asn Ser Val Ala Val Lys Arg Gly
            130                 135                 140

Asp Asp His Arg Val Leu Arg Val Ala Leu Ala Gly Phe Leu Gly Ser
145                 150                 155                 160

Ala Gly Leu Gln Leu Tyr Ile Gly Lys Met Ser Ala Leu Ile Arg Asn
            165                 170                 175

His Ile Asn Glu Lys Trp Lys Gly Lys Asp Glu Val Asn Val Leu Ser
            180                 185                 190

Leu Val Arg Asp Leu Val Met Asp Asn Ser Ala Ile Leu Phe Phe Asn
            195                 200                 205

Ile Tyr Asp Lys Glu Arg Lys Gln Gln Leu His Glu Ile Leu Lys Ile
210                 215                 220

Ile Leu Ala Ser His Phe Gly Ile Pro Leu Asn Ile Pro Gly Phe Leu
225                 230                 235                 240

Tyr Arg Lys Ala Leu Lys Gly Ser Leu Lys Arg Lys Ile Leu Ser
            245                 250                 255

Ala Leu Leu Glu Lys Arg Lys Asp Glu Leu Arg Ser Arg Leu Ala Ser
            260                 265                 270

Ser Asn Gln Asp Leu Leu Ser Val Leu Leu Ser Phe Arg Asp Glu Arg
            275                 280                 285

Gly Lys Pro Leu Ser Asp Glu Ala Val Leu Asp Asn Cys Phe Ala Met
290                 295                 300

Leu Asp Ala Ser Tyr Asp Thr Thr Thr Ser Gln Met Thr Leu Ile Leu
305                 310                 315                 320

Lys Met Leu Ser Ser Asn Pro Glu Cys Phe Glu Lys Val Val Gln Glu
            325                 330                 335

Gln Leu Glu Ile Ala Ser Asn Lys Lys Glu Gly Glu Glu Ile Thr Met
            340                 345                 350

Lys Asp Ile Lys Ala Met Lys Tyr Thr Trp Gln Val Leu Gln Glu Ser
            355                 360                 365

Leu Arg Met Leu Ser Pro Val Phe Gly Thr Leu Arg Lys Thr Met Asn
            370                 375                 380

Asp Ile Asn His Asp Gly Tyr Thr Ile Pro Lys Gly Trp Gln Val Val
385                 390                 395                 400

Trp Thr Thr Tyr Ser Thr His Gln Lys Asp Ile Tyr Phe Lys Gln Pro
            405                 410                 415

Asp Lys Phe Met Pro Ser Arg Phe Glu Glu Glu Asp Gly His Leu Asp
            420                 425                 430

Ala Tyr Thr Phe Val Pro Phe Gly Gly Gly Arg Arg Thr Cys Pro Gly
            435                 440                 445

Trp Glu Tyr Ala Lys Val Glu Ile Leu Leu Phe Leu His His Phe Val
            450                 455                 460
```

-continued

```
Lys Ala Phe Ser Gly Tyr Thr Pro Thr Asp Pro His Glu Arg Ile Cys
465                 470                 475                 480

Gly Tyr Pro Val Pro Leu Val Pro Val Lys Gly Phe Pro Ile Lys Leu
                485                 490                 495

Ile Ala Arg Ser
            500

<210> SEQ ID NO 9
<211> LENGTH: 1476
<212> TYPE: DNA
<213> ORGANISM: Taxus cuspidata
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t

<400> SEQUENCE: 9
atggatacca tacgagcaag ttttggcgaa gttattcagc cagagtattc tcctctcatc     60
atttccgncg ctctggcagc ttttcttggt attgttattt tctcgatctt cagttccact    120
cgacgatcct atgtgaatct ccccccgga aatttaggtt tacctttcat tggcgagacg     180
atacagttct tgggggcact tcagtcagaa aaaccccata cattttttcga tgagagagtg    240 aagaaattcg gtaaggtctt caagacttct ctaattgggg atcccacggt ggtactctgc    300
gggccggcgg gaaaccgctt agttctgtcg aacgaagaca agctggtgca gtccgcaggg    360
cccaagtctt tcctgaaact gtttggggag gattccgttg cggccaaaag agaagagagc    420
catcgcatct tacgttcggc tctgggtcga tttctgggtc cccatgcttt acagaattat    480
attgggaaaa tgaattcaga aatgcaacgn catttcgatg acaaatggaa gggaaaagat    540
gaggtgaagg tgcttccttt ggttagaggc ctcattttct ccattgctac ctccctgttc    600
ttcaatataa atgatgacag acaacgtgag caactccatg gtctgctgga tacaatactt    660
gtgggaagta tgactattcc tctgaacatt ccaggaactc tttttcgtaa agctgtcaag    720
gcacgggcga agctggacga aattcttttt gctttgatag agaacagaag aagagagctg    780
agatcgggcc taaattctgg taatcaagat cttctgtcgt ccttgctcac cttcaaagat    840
gaaaaaggga atccactgac agacaaggag atcctcgaca acttctctgt tatgcttcat    900
gcctcgtatg acactactgt ttcaccaacg tccttgatat tgaagcttct cgcctccaat    960
cctgaatgct atgaaaaagt tgttcaagag cagttgggaa tacttgctag taaaaaggag   1020
ggagaagaag tcaattggaa ggatctgaaa gctatgccat atacatggca agcaattcag   1080
gaacccctaa gnatgccccn ccagcttttg gaatgtttcg aagagctttc cctgatattc   1140
agttggaagg ctatacaatt ccaaaaggat gggcaattgt gtggccanct tatagtcaat   1200
gggagagaag agttcttcaa tgaaccagac aaattcaagc cttccagatt cgaggaagga   1260
```

```
aagcccctgg atccttacac attcatacca ttcggagcag gggtacgcat atgtgcagga    1320
tgggaatttg caaaggctga actattactg tttgtccatc cctttgttaa aaacttcagc    1380
ggttgcatta taattgatcc gaatgaaaaa atttcagggg atccattccc tccactccct    1440
accagtggac aactcatgaa acttattccg agatca                              1476
```

<210> SEQ ID NO 10
<211> LENGTH: 500
<212> TYPE: PRT
<213> ORGANISM: Taxus cuspidata
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (402)..(402)
<223> OTHER INFORMATION: Xaa can be any naturally occurring amino acid

<400> SEQUENCE: 10

```
Met Asp Thr Ile Arg Ala Ser Phe Gly Glu Val Ile Gln Pro Glu Tyr
 1               5                  10                  15

Ser Pro Leu Ile Ile Ser Xaa Ala Ala Leu Ala Ala Phe Leu Gly
            20                  25                  30

Ile Val Ile Phe Ser Ile Phe Ser Ser Thr Arg Arg Ser Tyr Val Asn
            35                  40                  45

Leu Pro Pro Gly Asn Leu Gly Leu Pro Phe Ile Gly Glu Thr Ile Gln
     50                  55                  60

Phe Leu Gly Ala Leu Gln Ser Glu Lys Pro His Thr Phe Phe Asp Glu
65                  70                  75                  80

Arg Val Lys Lys Phe Gly Lys Val Phe Lys Thr Ser Leu Ile Gly Asp
                85                  90                  95

Pro Thr Val Val Leu Cys Gly Pro Ala Gly Asn Arg Leu Val Leu Ser
            100                 105                 110

Asn Glu Asp Lys Leu Val Gln Ser Ala Gly Pro Lys Ser Phe Leu Lys
        115                 120                 125

Leu Phe Gly Glu Asp Ser Val Ala Ala Lys Arg Glu Glu Ser His Arg
    130                 135                 140

Ile Leu Arg Ser Ala Leu Gly Arg Phe Leu Gly Pro His Ala Leu Gln
145                 150                 155                 160

Asn Tyr Ile Gly Lys Met Asn Ser Glu Met Gln Arg His Phe Asp Asp
                165                 170                 175

Lys Trp Lys Gly Lys Asp Glu Val Lys Val Leu Pro Leu Val Arg Gly
            180                 185                 190

Leu Ile Phe Ser Ile Ala Thr Ser Leu Phe Phe Asn Ile Asn Asp Asp
        195                 200                 205

Arg Gln Arg Glu Gln Leu His Gly Leu Leu Asp Thr Ile Leu Val Gly
    210                 215                 220

Ser Met Thr Ile Pro Leu Asn Ile Pro Gly Thr Leu Phe Arg Lys Ala
225                 230                 235                 240

Val Lys Ala Arg Ala Lys Leu Asp Glu Ile Leu Phe Ala Leu Ile Glu
                245                 250                 255
```

```
Asn Arg Arg Arg Glu Leu Arg Ser Gly Leu Asn Ser Gly Asn Gln Asp
            260                 265                 270

Leu Leu Ser Ser Leu Leu Thr Phe Lys Asp Glu Lys Gly Asn Pro Leu
        275                 280                 285

Thr Asp Lys Glu Ile Leu Asp Asn Phe Ser Val Met Leu His Ala Ser
        290                 295                 300

Tyr Asp Thr Thr Val Ser Pro Thr Val Leu Ile Leu Lys Leu Leu Ala
305                 310                 315                 320

Ser Asn Pro Glu Cys Tyr Glu Lys Val Gln Glu Gln Leu Gly Ile
                325                 330                 335

Leu Ala Ser Lys Lys Glu Gly Glu Val Asn Trp Lys Asp Leu Lys
        340                 345                 350

Ala Met Pro Tyr Thr Trp Gln Ala Ile Gln Glu Pro Leu Xaa Ala Ala
        355                 360                 365

Met Pro Xaa Ala Ala Gln Leu Leu Glu Cys Phe Glu Glu Leu Ser Leu
    370                 375                 380

Ile Phe Ser Trp Lys Ala Ile Gln Phe Gln Lys Asp Gly Gln Leu Cys
385                 390                 395                 400

Gly Xaa Ala Ala Leu Ile Val Asn Gly Arg Glu Glu Phe Phe Asn Glu
                405                 410                 415

Pro Asp Lys Phe Lys Pro Ser Arg Phe Glu Glu Gly Lys Pro Leu Asp
            420                 425                 430

Pro Tyr Thr Phe Ile Pro Phe Gly Ala Gly Val Arg Ile Cys Ala Gly
            435                 440                 445

Trp Glu Phe Ala Lys Ala Glu Leu Leu Leu Phe Val His Pro Phe Val
450                 455                 460

Lys Asn Phe Ser Gly Cys Ile Ile Asp Pro Asn Glu Lys Ile Ser
465                 470                 475                 480

Gly Asp Pro Phe Pro Pro Leu Pro Thr Ser Gly Gln Leu Met Lys Leu
            485                 490                 495

Ile Pro Arg Ser
            500

<210> SEQ ID NO 11
<211> LENGTH: 1530
<212> TYPE: DNA
<213> ORGANISM: Taxus cuspidata

<400> SEQUENCE: 11
atggatgtct tttatccgtt aaaaagtaca gtagcaaaat ttaacgaatg tttccctgct    60
attcttttca ttgtcctcag tgctgttgct ggcattgttc tgccccctgct gctgttccta   120 cgttctaaac gccgttcctc tgttggacta cccccaggga aattaggtta cccttttcatt  180 ggcgagtcgt tactgttcct gaaggctctt cgatcaaaca cagttgaaca attttttggac 240 gagagagtga agaatttcgg gaatgtcttc aagacgtcat taattgggca tccgacagta   300
gttctctgcg ggcctgcagg aaaccggcta atcctggcga acgaggagaa gctggtgcag   360
atgtcgtggc ccaaatcctc tatgaaactc atggggagaa gtctattac tgccaaaagg   420 ggcgaaggcc atatgatcat ccgctccgca ctgcaaggct ttttcagccc tggtgctctg  480
cagaaataca taggccaaat gagtaaaaca atagaaaata tattaatga aaatggaaag   540 ggaaacgacc aagtgagtgt agttgctttg gtaggagatc tcgtcttcga tatttcggcc   600
tgtttgttct tcaatataaa tgagaagcat gaacgggaac gactgtttga gcttttggag   660
```

```
attatagctg tcggagtttt ggctgttccg gtggatcttc ccgggtttgc ttaccatcgg    720
gcacttcaag cacggtcgaa gcttaatgca attctctccg gtttgataga aaagagaaaa    780
atggatctga gctcaggatt agcgactagc aatcaggatc ttctttctgt gtttctcacc    840
ttcaaagatg acagaggaaa tccatgcagc gatgaggaaa tcctcgacaa cttttccggg    900
ctgcttcatg gatcctatga caccactgtt tcagcaatgg cctgcgtttt taagcttttg    960
tcttccaatc ccgaatgcta tgaaaaagta gttcaagagc aattggggat actttcgaat   1020
aaattggaag gagacgaaat cacatggaaa gatgtgaaat ccatgaaata tacatggcaa   1080
gtcgttcagg aaacgttacg attgtatccg tcaattttg gatcatttcg ccaggccatc    1140
actgacattc attataatgg ttacataatt ccaaaagggt ggaagctttt gtggacacca   1200
tacacaacac atcccaagga aatgtatttc agtgagccgg agaaattcct gccttcgagg   1260
ttcgatcagg aagggaaact tgtagctcct tacacatttt taccctttgg tggaggccag   1320
cgttcatgtc caggatggga attttcaaag atggagattt tactgtcggt gcatcatttt   1380
gttaaaacat tcagcacctt cacccccagtt gacccagcag aaataattgc aagagattcc   1440
ctctgccctc tccttccaa tgggttttct gtaaaacttt ttcctagatc ctattcactt    1500
cacacaggca accaggtcaa gaaaatataa                                    1530
```

```
<210> SEQ ID NO 12
<211> LENGTH: 509
<212> TYPE: PRT
<213> ORGANISM: Taxus cuspidata

<400> SEQUENCE: 12
```

Met Asp Val Phe Tyr Pro Leu Lys Ser Thr Val Ala Lys Phe Asn Glu
1               5                   10                  15

Cys Phe Pro Ala Ile Leu Phe Ile Val Leu Ser Ala Val Ala Gly Ile
            20                  25                  30

Val Leu Pro Leu Leu Leu Phe Leu Arg Ser Lys Arg Arg Ser Ser Val
        35                  40                  45

Gly Leu Pro Pro Gly Lys Leu Gly Tyr Pro Phe Ile Gly Glu Ser Leu
    50                  55                  60

Leu Phe Leu Lys Ala Leu Arg Ser Asn Thr Val Glu Gln Phe Leu Asp
65                  70                  75                  80

Glu Arg Val Lys Asn Phe Gly Asn Val Phe Lys Thr Ser Leu Ile Gly
                85                  90                  95

His Pro Thr Val Val Leu Cys Gly Pro Ala Gly Asn Arg Leu Ile Leu
            100                 105                 110

Ala Asn Glu Glu Lys Leu Val Gln Met Ser Trp Pro Lys Ser Ser Met
        115                 120                 125

Lys Leu Met Gly Glu Lys Ser Ile Thr Ala Lys Arg Gly Glu Gly His
    130                 135                 140

Met Ile Ile Arg Ser Ala Leu Gln Gly Phe Phe Ser Pro Gly Ala Leu
145                 150                 155                 160

Gln Lys Tyr Ile Gly Gln Met Ser Lys Thr Ile Glu Asn His Ile Asn
                165                 170                 175

Glu Lys Trp Lys Gly Asn Asp Gln Val Ser Val Ala Leu Val Gly
            180                 185                 190

Asp Leu Val Phe Asp Ile Ser Ala Cys Leu Phe Phe Asn Ile Asn Glu
        195                 200                 205

Lys His Glu Arg Glu Arg Leu Phe Glu Leu Leu Glu Ile Ile Ala Val
    210                 215                 220

```
Gly Val Leu Ala Val Pro Val Asp Leu Pro Gly Phe Ala Tyr His Arg
225                 230                 235                 240

Ala Leu Gln Ala Arg Ser Lys Leu Asn Ala Ile Leu Ser Gly Leu Ile
            245                 250                 255

Glu Lys Arg Lys Met Asp Leu Ser Ser Gly Leu Ala Thr Ser Asn Gln
        260                 265                 270

Asp Leu Leu Ser Val Phe Leu Thr Phe Lys Asp Asp Arg Gly Asn Pro
    275                 280                 285

Cys Ser Asp Glu Glu Ile Leu Asp Asn Phe Ser Gly Leu Leu His Gly
290                 295                 300

Ser Tyr Asp Thr Thr Val Ser Ala Met Ala Cys Val Phe Lys Leu Leu
305                 310                 315                 320

Ser Ser Asn Pro Glu Cys Tyr Glu Lys Val Gln Glu Gln Leu Gly
                325                 330                 335

Ile Leu Ser Asn Lys Leu Glu Gly Asp Glu Ile Thr Trp Lys Asp Val
                340                 345                 350

Lys Ser Met Lys Tyr Thr Trp Gln Val Val Gln Glu Thr Leu Arg Leu
            355                 360                 365

Tyr Pro Ser Ile Phe Gly Ser Phe Arg Gln Ala Ile Thr Asp Ile His
370                 375                 380

Tyr Asn Gly Tyr Ile Ile Pro Lys Gly Trp Lys Leu Leu Trp Thr Pro
385                 390                 395                 400

Tyr Thr Thr His Pro Lys Glu Met Tyr Phe Ser Glu Pro Glu Lys Phe
                405                 410                 415

Leu Pro Ser Arg Phe Asp Gln Glu Gly Lys Leu Val Ala Pro Tyr Thr
            420                 425                 430

Phe Leu Pro Phe Gly Gly Gly Gln Arg Ser Cys Pro Gly Trp Glu Phe
        435                 440                 445

Ser Lys Met Glu Ile Leu Leu Ser Val His His Phe Val Lys Thr Phe
    450                 455                 460

Ser Thr Phe Thr Pro Val Asp Pro Ala Glu Ile Ile Ala Arg Asp Ser
465                 470                 475                 480

Leu Cys Pro Leu Pro Ser Asn Gly Phe Ser Val Lys Leu Phe Pro Arg
                485                 490                 495

Ser Tyr Ser Leu His Thr Gly Asn Gln Val Lys Lys Ile
            500                 505

<210> SEQ ID NO 13
<211> LENGTH: 1503
<212> TYPE: DNA
<213> ORGANISM: Taxus cuspidata
<220> FEATURE:
<221> NAME/KEY: misc_feature
<222> LOCATION: (1151)..(1151)
<223> OTHER INFORMATION: n is a, c, g, or t

<400> SEQUENCE: 13
atggatagct tcaatttctt gagaggcatt ggagcagatt ttgggggatt cattcagttc      60
cagtcttccc ctgctgttct ttcccttttcc ctgatcacaa ctattcttgg cgttctactt     120
ctctggttct tccttcataa aaacggttcc tctgttactc tccccctgg aaatttaggc      180 ttcccttca ttggggagac cataccattc ttgagggcac ttcgatcaga aacacctcag      240
acgttttttg atgagagggt gaagaaattc ggtgttgtat tcaagactcg gatagttggg      300
catcccacag ttgtactctg cgggcctgag ggaaaccgct tcttctctc caacgaggac      360
```

-continued

```
aaactggtgc aggcgtcatt gcccaactct tccgagaaac taattgggaa atattccatt    420
ctgtccaaaa gaggggagga gcatcgcata ttacgtgctg cacttgcccg cttttttgcga   480 ccccaagctt tgcagggtta tgttgctaaa atgagttcag aaatccaaca tcatatcaag   540
caaaaatgga agggaaatga tgaagtgaag gtgcttcctc tgataagaac cctgatcttc   600
aacattgcaa gcagcctgtt tttcggcata aatgatgaac accaacagga acagcttcat   660
catcttttgg aagccattgt tctgggaagt ctgtctgttc cgctcgactt tccaggaact   720
cgttttcgta agctcttga tgcgcggtct aagctggatg agattctttc ttctttaatg   780
gagagcagaa aagggatct gcgtttgggc acggcttctg agaatcaaga tcttctttct   840
gtgttgctca ccttcaaaga tgaaagaggg aatccactca cagacaagga atcttcgac    900 aatttttcat ttatgcttca tgcctcgtat gataccactg tttcaccaac gggtttgatg   960
cttaagcttc tcttctctag tcctgattgc tatgaaaaac tagttcaaga acaattggga  1020
atagttggca ataaaaagga gggagaagaa atcagctgga acgatctgaa agctatgaaa  1080
tatacatgca aggttgtgca ggaaagtatg aggatgctcc ctccagtttt tggatcgtat  1140
cgcaaggcta ncacctatat ccattatgat gggtatacaa ttccaaaagg atggaatata  1200
ttctggtcac cttatactac acacgggaaa gaagaatact tcaatgaagc ggacaagttc  1260
atgccttcga gattcgagga aggcaaatat gttgctcctt acacattctt gccattcgga  1320
gcaggtctgc gcgtatgtcc aggatgggaa tttgcaaaga ccgagatatt actgttcgtc  1380
catcatttta ttcaactttt cagcagctac atcccaattg accccaaaga taaaattcca  1440
ggggatccat ttcctcctct gcctaccaat ggattttcca tgaaactttt taccagatct  1500
taa                                                                1503
```

<210> SEQ ID NO 14
<211> LENGTH: 502
<212> TYPE: PRT
<213> ORGANISM: Taxus cuspidata
<220> FEATURE:
<221> NAME/KEY: misc_feature
<222> LOCATION: (384)..(384)
<223> OTHER INFORMATION: Xaa can be any naturally occurring amino acid

<400> SEQUENCE: 14

```
Met Asp Ser Phe Asn Phe Leu Arg Gly Ile Gly Ala Asp Phe Gly Gly
  1               5                  10                  15

Phe Ile Gln Phe Gln Ser Ser Pro Ala Val Leu Ser Leu Ser Leu Ile
             20                  25                  30

Thr Thr Ile Leu Gly Val Leu Leu Leu Trp Phe Phe Leu His Lys Asn
         35                  40                  45

Gly Ser Ser Val Thr Leu Pro Pro Gly Asn Leu Gly Phe Pro Phe Ile
     50                  55                  60

Gly Glu Thr Ile Pro Phe Leu Arg Ala Leu Arg Ser Glu Thr Pro Gln
 65                  70                  75                  80

Thr Phe Phe Asp Glu Arg Val Lys Lys Phe Gly Val Val Phe Lys Thr
                 85                  90                  95

Arg Ile Val Gly His Pro Thr Val Val Leu Cys Gly Pro Glu Gly Asn
            100                 105                 110

Arg Phe Leu Leu Ser Asn Glu Asp Lys Leu Val Gln Ala Ser Leu Pro
        115                 120                 125

Asn Ser Ser Glu Lys Leu Ile Gly Lys Tyr Ser Ile Leu Ser Lys Arg
    130                 135                 140
```

```
Gly Glu Glu His Arg Ile Leu Arg Ala Ala Leu Ala Arg Phe Leu Arg
145                 150                 155                 160

Pro Gln Ala Leu Gln Gly Tyr Val Ala Lys Met Ser Ser Glu Ile Gln
            165                 170                 175

His His Ile Lys Gln Lys Trp Lys Gly Asn Asp Glu Val Lys Val Leu
        180                 185                 190

Pro Leu Ile Arg Thr Leu Ile Phe Asn Ile Ala Ser Ser Leu Phe Phe
    195                 200                 205

Gly Ile Asn Asp Glu His Gln Gln Glu Gln Leu His His Leu Leu Glu
210                 215                 220

Ala Ile Val Leu Gly Ser Leu Ser Val Pro Leu Asp Phe Pro Gly Thr
225                 230                 235                 240

Arg Phe Arg Lys Ala Leu Asp Ala Arg Ser Lys Leu Asp Glu Ile Leu
            245                 250                 255

Ser Ser Leu Met Glu Ser Arg Arg Asp Leu Arg Leu Gly Thr Ala
        260                 265                 270

Ser Glu Asn Gln Asp Leu Leu Ser Val Leu Leu Thr Phe Lys Asp Glu
    275                 280                 285

Arg Gly Asn Pro Leu Thr Asp Lys Glu Ile Phe Asp Asn Phe Ser Phe
290                 295                 300

Met Leu His Ala Ser Tyr Asp Thr Thr Val Ser Pro Thr Gly Leu Met
305                 310                 315                 320

Leu Lys Leu Leu Phe Ser Ser Pro Asp Cys Tyr Glu Lys Leu Val Gln
            325                 330                 335

Glu Gln Leu Gly Ile Val Gly Asn Lys Lys Glu Gly Glu Glu Ile Ser
        340                 345                 350

Trp Asn Asp Leu Lys Ala Met Lys Tyr Thr Cys Lys Val Val Gln Glu
    355                 360                 365

Ser Met Arg Met Leu Pro Pro Val Phe Gly Ser Tyr Arg Lys Ala Xaa
370                 375                 380

Ala Ala Thr Tyr Ile His Tyr Asp Gly Tyr Thr Ile Pro Lys Gly Trp
385                 390                 395                 400

Asn Ile Phe Trp Ser Pro Tyr Thr Thr His Gly Lys Glu Glu Tyr Phe
            405                 410                 415

Asn Glu Ala Asp Lys Phe Met Pro Ser Arg Phe Glu Glu Gly Lys Tyr
        420                 425                 430

Val Ala Pro Tyr Thr Phe Leu Pro Phe Gly Ala Gly Leu Arg Val Cys
    435                 440                 445

Pro Gly Trp Glu Phe Ala Lys Thr Glu Ile Leu Leu Phe Val His His
450                 455                 460

Phe Ile Thr Thr Phe Ser Ser Tyr Ile Pro Ile Asp Pro Lys Asp Lys
465                 470                 475                 480

Ile Ser Gly Asp Pro Phe Pro Pro Leu Pro Thr Asn Gly Phe Ser Met
            485                 490                 495

Lys Leu Phe Thr Arg Ser
        500
```

<210> SEQ ID NO 15
<211> LENGTH: 1494
<212> TYPE: DNA
<213> ORGANISM: Taxus cuspidata

<400> SEQUENCE: 15
atggatagct tcattttct gagaagcata ggaacaaaat ttgggcagct ggagtcttcc      60

```
cctgctattc tttcccttac cctcgcacct attctcgcca ttattcttct cttgctcttc    120
cgttacaatc accgatcctc tgttaaactt cccccctggaa agttaggttt tcctctcatc    180
ggggagacca tacaattatt gcggacactc cgatcagaaa cacctcaaaa gttttttgat    240
gatagattga agaaattcgg tcctgtttac atgacttccc taattgggca tcccacagtt    300
gtactctgcg ggcctgcggg aaacaaatta gttctttcga acgaggacaa gctggtagag    360
atggaagggc ccaagtcttt catgaaactg attggggaag attccattgt tgctaaaaga    420
ggcgaggatc atcgcatctt acgcactgca cttgctcggt ttttgggcgc tcaagcttta    480
caaaattatc tgggtagaat gagttcagaa ataggacacc atttcaatga aaatggaag    540 ggtaaagatg aagtgaaggt gcttcctttg gtaagagggc ttatcttctc cattgcaagc    600
accctgtttt tcgatgtaaa tgatggacac caacagaagc aacttcatca tcttctggaa    660
actattcttg tgggaagttt gtcagtcccg ctggactttc caggaactcg ttatcgtaaa    720
gggcttcagg cgcggctgaa gcttgatgaa attctctcct ctctaataaa acgcagaaga    780
agagatctgc gttcaggcat agcttctgat gatcaagatc tactgtcggt gttgctcacc    840
ttcagagatg aaaaagggaa ctcactgaca gaccagggga ttctggacaa ctttctgct    900 atgtttcatg cttcatatga caccactgtt gcaccaatgg ccttgatatt taagcttcta    960
tactccaatc ctgaatacca tgaaaaagta tttcaagagc agttgaaaat aattggcaat    1020
aaaaaggaag gggaagaaat cagttggaag gatttgaaat ctatgaaata tacatggcaa    1080
gcagttcaag aatcactacg aatgtaccca ccagttttttg gaatatttcg taaggctatc    1140
actgatattc attatgatgg gtatacaatt ccaaaaggat ggagggtttt atgttcacct    1200
tatactacac atctgagaga agagtacttc cctgagcctg aagaattcag gccttcaaga    1260
tttgaggatg aaggcaggca tgtgactcct tacacatatg taccatttgg aggaggcctg    1320
cgcacatgtc caggatggga attttcaaag attgaaatat tactgtttgt ccatcatttc    1380
gttaaaaatt tcagcagcta cattccagtt gatcccaatg aaaaagtttt atcagatcca    1440
ctacctcctc tccctgccaa tggatttttcc ataaaacttt ttccgagatc ctaa    1494
```

<210> SEQ ID NO 16
<211> LENGTH: 497
<212> TYPE: PRT
<213> ORGANISM: Taxus cuspidata

<400> SEQUENCE: 16

```
Met Asp Ser Phe Ile Phe Leu Arg Ser Ile Gly Thr Lys Phe Gly Gln
  1               5                  10                  15

Leu Glu Ser Ser Pro Ala Ile Leu Ser Leu Thr Leu Ala Pro Ile Leu
             20                  25                  30

Ala Ile Ile Leu Leu Leu Phe Arg Tyr Asn His Arg Ser Ser Val
         35                  40                  45

Lys Leu Pro Pro Gly Lys Leu Gly Phe Pro Leu Ile Gly Glu Thr Ile
     50                  55                  60

Gln Leu Leu Arg Thr Leu Arg Ser Glu Thr Pro Gln Lys Phe Phe Asp
 65                  70                  75                  80

Asp Arg Leu Lys Lys Phe Gly Pro Val Tyr Met Thr Ser Leu Ile Gly
                 85                  90                  95

His Pro Thr Val Val Leu Cys Gly Pro Ala Gly Asn Lys Leu Val Leu
            100                 105                 110

Ser Asn Glu Asp Lys Leu Val Glu Met Glu Gly Pro Lys Ser Phe Met
        115                 120                 125
```

```
Lys Leu Ile Gly Glu Asp Ser Ile Val Ala Lys Arg Gly Glu Asp His
    130                 135                 140
Arg Ile Leu Arg Thr Ala Leu Ala Arg Phe Leu Gly Ala Gln Ala Leu
145                 150                 155                 160
Gln Asn Tyr Leu Gly Arg Met Ser Ser Glu Ile Gly His His Phe Asn
                165                 170                 175
Glu Lys Trp Lys Gly Lys Asp Glu Val Lys Val Leu Pro Leu Val Arg
            180                 185                 190
Gly Leu Ile Phe Ser Ile Ala Ser Thr Leu Phe Phe Asp Val Asn Asp
        195                 200                 205
Gly His Gln Gln Lys Gln Leu His His Leu Leu Glu Thr Ile Leu Val
    210                 215                 220
Gly Ser Leu Ser Val Pro Leu Asp Phe Pro Gly Thr Arg Tyr Arg Lys
225                 230                 235                 240
Gly Leu Gln Ala Arg Leu Lys Leu Asp Glu Ile Leu Ser Ser Leu Ile
                245                 250                 255
Lys Arg Arg Arg Arg Asp Leu Arg Ser Gly Ile Ala Ser Asp Asp Gln
            260                 265                 270
Asp Leu Leu Ser Val Leu Leu Thr Phe Arg Asp Glu Lys Gly Asn Ser
        275                 280                 285
Leu Thr Asp Gln Gly Ile Leu Asp Asn Phe Ser Ala Met Phe His Ala
    290                 295                 300
Ser Tyr Asp Thr Thr Val Ala Pro Met Ala Leu Ile Phe Lys Leu Leu
305                 310                 315                 320
Tyr Ser Asn Pro Glu Tyr His Glu Lys Val Phe Gln Glu Gln Leu Glu
                325                 330                 335
Ile Ile Gly Asn Lys Lys Glu Gly Glu Ile Ser Trp Lys Asp Leu
            340                 345                 350
Lys Ser Met Lys Tyr Thr Trp Gln Ala Val Gln Glu Ser Leu Arg Met
        355                 360                 365
Tyr Pro Pro Val Phe Gly Ile Phe Arg Lys Ala Ile Thr Asp Ile His
    370                 375                 380
Tyr Asp Gly Tyr Thr Ile Pro Lys Gly Trp Arg Val Leu Cys Ser Pro
385                 390                 395                 400
Tyr Thr Thr His Leu Arg Glu Glu Tyr Phe Pro Glu Pro Glu Glu Phe
                405                 410                 415
Arg Pro Ser Arg Phe Glu Asp Glu Gly Arg His Val Thr Pro Tyr Thr
            420                 425                 430
Tyr Val Pro Phe Gly Gly Gly Leu Arg Thr Cys Pro Gly Trp Glu Phe
        435                 440                 445
Ser Lys Ile Glu Ile Leu Leu Phe Val His His Phe Val Lys Asn Phe
    450                 455                 460
Ser Ser Tyr Ile Pro Val Asp Pro Asn Glu Lys Val Leu Ser Asp Pro
465                 470                 475                 480
Leu Pro Pro Leu Pro Ala Asn Gly Phe Ser Ile Lys Leu Phe Pro Arg
                485                 490                 495
Ser
```

<210> SEQ ID NO 17
<211> LENGTH: 1458
<212> TYPE: DNA
<213> ORGANISM: Taxus cuspidata

<400> SEQUENCE: 17

```
atggatgccc ttaagcaatt ggaagtttcc ccttccattc ttttcgttac cctcgcagta      60
atggcaggca ttatcctctt cttccgctct aaacgccatt cctctgtaaa actccccct      120 ggaaatctag gcttccctct ggttggggag acactgcagt tcgtgaggtc acttggctcg     180
agcactccac agcagtttat tgaagagaga atgagcaaat ttggggatgt gttcaagact     240
tccataatcg gcatcccac agtagtgctg tgtggacctg ccggaaaccg gttggttctg     300
tcgaacgaga acaagctggt gcagatgtca tggccgagct ccatgatgaa actcatcggc     360
gaagattgtc tcggcggcaa aacgggagag cagcatcgga tcgtacgcgc tgcactaact     420 cggttttgg gtcctcaagc attgcagaat catttcgcta aaatgagctc gggaatccaa      480
cgccacatca atgaaaaatg gaagggaaag gatgaggcca ctgtacttcc tttggtaaaa     540
gacctcgtct ctccgtcgc aagccgcttg ttttttggta taactgagga gcacctgcag      600
gagcaacttc ataacttgtt ggaagttatt cttgtgggat cttttctgt tccactcaac      660 attcccggat tcagttacca taaagcgatt caggcaaggg ccaccctcgc tgacatcatg     720
acccatttga tagaaaagag gagaaatgag ctgcgtgcag gcactgcatc tgagaatcaa     780
gatttgctct ctgtttttgct cactttcact gacgaaaggg ggaattcact ggcggacaag     840
gagatcctcg acaactttc tatgttactt catggatcat atgactccac caattcccca      900
cttaccatgt tgattaaagt cttggcctcc catccagaaa gctatgaaaa agtggctcaa     960
gagcaatttg gaatactctc caccaaaatg gagggagaag aaattgcttg gaaagacctg    1020
aaggagatga aatattcatg gcaagttgtt caggaaacat tgcgcatgta tcctcccatt    1080
tttggaacat ttcgcaaagc catcactgac attcattaca atggttatac aattccaaaa    1140
ggatggaaac ttttatggac aacttacagt actcaaacca aggaagagta tttcaaggac    1200
gccgatcaat tcaagccatc aagatttgag gaggaaggga agcatgtaac cccttacaca    1260
tacttacctt tcggaggagg catgcgtgtt tgtccagggt gggaattcgc caagatggag    1320
acattactgt ttctccatca ttttgttaaa gccttctctg gttgaaggc aattgatcca    1380 aatgaaaaac tttcagggaa accacttcct cctctccctg tcaatgggct tcccattaaa    1440
ctctattcca gatcttaa                                                  1458
```

<210> SEQ ID NO 18
<211> LENGTH: 485
<212> TYPE: PRT
<213> ORGANISM: Taxus cuspidata

<400> SEQUENCE: 18

```
Met Asp Ala Leu Lys Gln Leu Glu Val Ser Pro Ser Ile Leu Phe Val
1               5                   10                  15

Thr Leu Ala Val Met Ala Gly Ile Ile Leu Phe Phe Arg Ser Lys Arg
            20                  25                  30

His Ser Val Lys Leu Pro Pro Gly Asn Leu Gly Phe Pro Leu Val
            35                  40                  45

Gly Glu Thr Leu Gln Phe Val Arg Ser Leu Gly Ser Ser Thr Pro Gln
        50                  55                  60

Gln Phe Ile Glu Glu Arg Met Ser Lys Phe Gly Asp Val Phe Lys Thr
65                  70                  75                  80

Ser Ile Ile Gly His Pro Thr Val Val Leu Cys Gly Pro Ala Gly Asn
                85                  90                  95

Arg Leu Val Leu Ser Asn Glu Asn Lys Leu Val Gln Met Ser Trp Pro
            100                 105                 110
```

Ser Ser Met Met Lys Leu Ile Gly Glu Asp Cys Leu Gly Gly Lys Thr
        115                 120                 125

Gly Glu Gln His Arg Ile Val Arg Ala Ala Leu Thr Arg Phe Leu Gly
    130                 135                 140

Pro Gln Ala Leu Gln Asn His Phe Ala Lys Met Ser Ser Gly Ile Gln
145                 150                 155                 160

Arg His Ile Asn Glu Lys Trp Lys Gly Lys Asp Glu Ala Thr Val Leu
                165                 170                 175

Pro Leu Val Lys Asp Leu Val Phe Ser Val Ala Ser Arg Leu Phe Phe
            180                 185                 190

Gly Ile Thr Glu Glu His Leu Gln Glu Gln Leu His Asn Leu Leu Glu
        195                 200                 205

Val Ile Leu Val Gly Ser Phe Ser Val Pro Leu Asn Ile Pro Gly Phe
    210                 215                 220

Ser Tyr His Lys Ala Ile Gln Ala Arg Ala Thr Leu Ala Asp Ile Met
225                 230                 235                 240

Thr His Leu Ile Glu Lys Arg Arg Asn Glu Leu Arg Ala Gly Thr Ala
                245                 250                 255

Ser Glu Asn Gln Asp Leu Leu Ser Val Leu Leu Thr Phe Thr Asp Glu
            260                 265                 270

Arg Gly Asn Ser Leu Ala Asp Lys Glu Ile Leu Asp Asn Phe Ser Met
        275                 280                 285

Leu Leu His Gly Ser Tyr Asp Ser Thr Asn Ser Pro Leu Thr Met Leu
    290                 295                 300

Ile Lys Val Leu Ala Ser His Pro Glu Ser Tyr Glu Lys Val Ala Gln
305                 310                 315                 320

Glu Gln Phe Gly Ile Leu Ser Thr Lys Met Glu Gly Glu Glu Ile Ala
                325                 330                 335

Trp Lys Asp Leu Lys Glu Met Lys Tyr Ser Trp Gln Val Val Gln Glu
            340                 345                 350

Thr Leu Arg Met Tyr Pro Pro Ile Phe Gly Thr Phe Arg Lys Ala Ile
        355                 360                 365

Thr Asp Ile His Tyr Asn Gly Tyr Thr Ile Pro Lys Gly Trp Lys Leu
    370                 375                 380

Leu Trp Thr Thr Tyr Ser Thr Gln Thr Lys Glu Glu Tyr Phe Lys Asp
385                 390                 395                 400

Ala Asp Gln Phe Lys Pro Ser Arg Phe Glu Glu Gly Lys His Val
                405                 410                 415

Thr Pro Tyr Thr Tyr Leu Pro Phe Gly Gly Gly Met Arg Val Cys Pro
            420                 425                 430

Gly Trp Glu Phe Ala Lys Met Glu Thr Leu Leu Phe Leu His His Phe
        435                 440                 445

Val Lys Ala Phe Ser Gly Leu Lys Ala Ile Asp Pro Asn Glu Lys Leu
    450                 455                 460

Ser Gly Lys Pro Leu Pro Pro Leu Pro Val Asn Gly Leu Pro Ile Lys
465                 470                 475                 480

Leu Tyr Ser Arg Ser
                485

<210> SEQ ID NO 19
<211> LENGTH: 2700
<212> TYPE: DNA
<213> ORGANISM: Taxus brevifolia
<220> FEATURE:

<221> NAME/KEY: CDS
<222> LOCATION: (22)..(2610)
<223> OTHER INFORMATION: coding sequence

<400> SEQUENCE: 19

```
ttcccctgcc tctctggaga a atg gct cag ctc tca ttt aat gca gcg ctg        51
                       Met Ala Gln Leu Ser Phe Asn Ala Ala Leu
                        1               5                  10 aag atg aac gca ttg ggg aac aag gca atc cac gat cca acg aat tgc        99
Lys Met Asn Ala Leu Gly Asn Lys Ala Ile His Asp Pro Thr Asn Cys
             15                  20                  25 aga gcc aaa tct gag cgc caa atg atg tgg gtt tgc tcc aga tca ggg       147
Arg Ala Lys Ser Glu Arg Gln Met Met Trp Val Cys Ser Arg Ser Gly
         30                  35                  40 cga acc aga gta aaa atg tcg aga gga agt ggt ggt cct ggt cct gtc       195
Arg Thr Arg Val Lys Met Ser Arg Gly Ser Gly Gly Pro Gly Pro Val
     45                  50                  55 gta atg atg agc agc agc act ggc act agc aag gtg gtt tcc gag act       243
Val Met Met Ser Ser Ser Thr Gly Thr Ser Lys Val Val Ser Glu Thr
 60                  65                  70 tcc agt acc att gtg gat gat atc cct cga ctc tcc gcc aat tat cat       291
Ser Ser Thr Ile Val Asp Asp Ile Pro Arg Leu Ser Ala Asn Tyr His
 75                  80                  85                  90 ggc gat ctg tgg cac cac aat gtt ata caa act ctg gag aca ccg ttt       339
Gly Asp Leu Trp His His Asn Val Ile Gln Thr Leu Glu Thr Pro Phe
                 95                 100                 105 cgt gag agt tct act tac caa gaa cgg gca gat gag ctg gtt gtg aaa       387
Arg Glu Ser Ser Thr Tyr Gln Glu Arg Ala Asp Glu Leu Val Val Lys
             110                 115                 120 att aaa gat atg ttc aat gcg ctc gga gac gga gat atc agt ccg tct       435
Ile Lys Asp Met Phe Asn Ala Leu Gly Asp Gly Asp Ile Ser Pro Ser
         125                 130                 135 gca tac gac act gcg tgg gtg gcg agg ctg gcg acc att tcc tct gat       483
Ala Tyr Asp Thr Ala Trp Val Ala Arg Leu Ala Thr Ile Ser Ser Asp
     140                 145                 150 gga tct gag aag cca cgg ttt cct cag gcc ctc aac tgg gtt ttc aac       531
Gly Ser Glu Lys Pro Arg Phe Pro Gln Ala Leu Asn Trp Val Phe Asn
155                 160                 165                 170 aac cag ctc cag gat gga tcg tgg ggt atc gaa tcg cac ttt agt tta       579
Asn Gln Leu Gln Asp Gly Ser Trp Gly Ile Glu Ser His Phe Ser Leu
                 175                 180                 185 tgc gat cga ttg ctt aac acg acc aat tct gtt atc gcc ctc tcg gtt       627
Cys Asp Arg Leu Leu Asn Thr Thr Asn Ser Val Ile Ala Leu Ser Val
             190                 195                 200 tgg aaa aca ggg cac agc caa gta caa caa ggt gct gag ttt att gca       675
Trp Lys Thr Gly His Ser Gln Val Gln Gln Gly Ala Glu Phe Ile Ala
         205                 210                 215 gag aat cta aga tta ctc aat gag gaa gat gag ttg tcc ccg gat ttc       723
Glu Asn Leu Arg Leu Leu Asn Glu Glu Asp Glu Leu Ser Pro Asp Phe
     220                 225                 230 caa ata atc ttt cct gct ctg ctg caa aag gca aaa gcg ttg ggg atc       771
Gln Ile Ile Phe Pro Ala Leu Leu Gln Lys Ala Lys Ala Leu Gly Ile
235                 240                 245                 250 aat ctt cct tac gat ctt cca ttt atc aaa tat ttg tcg aca aca cgg       819
Asn Leu Pro Tyr Asp Leu Pro Phe Ile Lys Tyr Leu Ser Thr Thr Arg
                 255                 260                 265 gaa gcc agg ctt aca gat gtt tct gcg gca gca gac aat att cca gcc       867
Glu Ala Arg Leu Thr Asp Val Ser Ala Ala Ala Asp Asn Ile Pro Ala
             270                 275                 280 aac atg ttg aat gcg ttg gaa ggt ctc gag gaa gtt att gac tgg aac       915
Asn Met Leu Asn Ala Leu Glu Gly Leu Glu Glu Val Ile Asp Trp Asn
```

```
        Asn Met Leu Asn Ala Leu Glu Gly Leu Glu Val Ile Asp Trp Asn
                    285                 290                 295 aag att atg agg ttt caa agt aaa gat gga tct ttc ctg agc tcc cct    963
Lys Ile Met Arg Phe Gln Ser Lys Asp Gly Ser Phe Leu Ser Ser Pro
300                 305                 310 gcc tcc act gcc tgt gta ctg atg aat aca ggg gac gaa aaa tgt ttc   1011
Ala Ser Thr Ala Cys Val Leu Met Asn Thr Gly Asp Glu Lys Cys Phe
315                 320                 325                 330 act ttt ctc aac aat ctg ctc gac aaa ttc ggc ggc tgc gtg ccc tgt   1059
Thr Phe Leu Asn Asn Leu Leu Asp Lys Phe Gly Gly Cys Val Pro Cys
                335                 340                 345 atg tat tcc atc gat ctg ctg gaa cgc ctt tcg ctg gtt gat aac att   1107
Met Tyr Ser Ile Asp Leu Leu Glu Arg Leu Ser Leu Val Asp Asn Ile
            350                 355                 360 gag cat ctc gga atc ggt cgc cat ttc aaa caa gaa atc aaa gga gct   1155
Glu His Leu Gly Ile Gly Arg His Phe Lys Gln Glu Ile Lys Gly Ala
        365                 370                 375 ctt gat tat gtc tac aga cat tgg agt gaa agg ggc atc ggt tgg ggc   1203
Leu Asp Tyr Val Tyr Arg His Trp Ser Glu Arg Gly Ile Gly Trp Gly
    380                 385                 390 aga gac agc ctt gtt cca gat ctc aac acc aca gcc ctc ggc ctg cga   1251
Arg Asp Ser Leu Val Pro Asp Leu Asn Thr Thr Ala Leu Gly Leu Arg
395                 400                 405                 410 act ctt cgc atg cac gga tac aat gtt tct tca gac gtt ttg aat aat   1299
Thr Leu Arg Met His Gly Tyr Asn Val Ser Ser Asp Val Leu Asn Asn
                415                 420                 425 ttc aaa gat gaa aac ggg cgg ttc ttc tcc tct gcg ggc caa acc cat   1347
Phe Lys Asp Glu Asn Gly Arg Phe Phe Ser Ser Ala Gly Gln Thr His
                430                 435                 440 gtc gaa ttg aga agc gtg gtg aat ctt ttc aga gct tcc gac ctt gca   1395
Val Glu Leu Arg Ser Val Val Asn Leu Phe Arg Ala Ser Asp Leu Ala
            445                 450                 455 ttt cct gac gaa aga gct atg gac gat gct aga aaa ttt gca gaa cca   1443
Phe Pro Asp Glu Arg Ala Met Asp Asp Ala Arg Lys Phe Ala Glu Pro
        460                 465                 470 tat ctt aga gag gca ctt gca acg aaa atc tca acc aat aca aaa cta   1491
Tyr Leu Arg Glu Ala Leu Ala Thr Lys Ile Ser Thr Asn Thr Lys Leu
475                 480                 485                 490 ttc aaa gag att gag tac gtg gtg gag tac cct tgg cac atg agt atc   1539
Phe Lys Glu Ile Glu Tyr Val Val Glu Tyr Pro Trp His Met Ser Ile
                495                 500                 505 cca cgc tta gaa gcc aga agt tat att gat tca tat gac gac aat tat   1587
Pro Arg Leu Glu Ala Arg Ser Tyr Ile Asp Ser Tyr Asp Asp Asn Tyr
                510                 515                 520 gta tgg cag agg aag act cta tat aga atg cca tct ttg agt aat tca   1635
Val Trp Gln Arg Lys Thr Leu Tyr Arg Met Pro Ser Leu Ser Asn Ser
            525                 530                 535 aaa tgt tta gaa ttg gca aaa ttg gac ttc aat atc gta caa tct ttg   1683
Lys Cys Leu Glu Leu Ala Lys Leu Asp Phe Asn Ile Val Gln Ser Leu
        540                 545                 550 cat caa gag gag ttg aag ctt cta aca aga tgg tgg aag gaa tcc ggc   1731
His Gln Glu Glu Leu Lys Leu Leu Thr Arg Trp Trp Lys Glu Ser Gly
555                 560                 565                 570 atg gca gat ata aat ttc act cga cac cga gtg gcg gag gtt tat ttt   1779
Met Ala Asp Ile Asn Phe Thr Arg His Arg Val Ala Glu Val Tyr Phe
                575                 580                 585 tca tca gct aca ttt gaa ccc gaa tat tct gcc act aga att gcc ttc   1827
Ser Ser Ala Thr Phe Glu Pro Glu Tyr Ser Ala Thr Arg Ile Ala Phe
                590                 595                 600
```

```
aca aaa att ggt tgt tta caa gtc ctt ttt gat gat atg gct gac atc      1875
Thr Lys Ile Gly Cys Leu Gln Val Leu Phe Asp Asp Met Ala Asp Ile
        605                 610                 615 ttt gca aca cta gat gaa ttg aaa agt ttc act gag gga gta aag aga      1923
Phe Ala Thr Leu Asp Glu Leu Lys Ser Phe Thr Glu Gly Val Lys Arg
620                 625                 630 tgg gat aca tct ttg cta cat gag att cca gag tgt atg caa act tgc      1971
Trp Asp Thr Ser Leu Leu His Glu Ile Pro Glu Cys Met Gln Thr Cys
635                 640                 645                 650 ttt aaa gtt tgg ttc aaa tta atg gaa gaa gta aat aat gat gtg gtt      2019
Phe Lys Val Trp Phe Lys Leu Met Glu Glu Val Asn Asn Asp Val Val
                655                 660                 665 aag gta caa gga cgt gac atg ctc gct cac ata aga aaa ccc tgg gag      2067
Lys Val Gln Gly Arg Asp Met Leu Ala His Ile Arg Lys Pro Trp Glu
            670                 675                 680 ttg tac ttc aat tgt tat gta caa gaa agg gag tgg ctt gaa gcc ggg      2115
Leu Tyr Phe Asn Cys Tyr Val Gln Glu Arg Glu Trp Leu Glu Ala Gly
        685                 690                 695 tat ata cca act ttt gaa gag tac tta aag act tat gct ata tca gta      2163
Tyr Ile Pro Thr Phe Glu Glu Tyr Leu Lys Thr Tyr Ala Ile Ser Val
700                 705                 710 ggc ctt gga ccg tgt acc cta caa cca ata cta cta atg ggt gag ctt      2211
Gly Leu Gly Pro Cys Thr Leu Gln Pro Ile Leu Leu Met Gly Glu Leu
715                 720                 725                 730 gtg aaa gat gat gtt gtt gag aaa gtg cac tat ccc tca aat atg ttt      2259
Val Lys Asp Asp Val Val Glu Lys Val His Tyr Pro Ser Asn Met Phe
                735                 740                 745 gag ctt gta tcc ttg agc tgg cga cta aca aac gac acc aaa aca tat      2307
Glu Leu Val Ser Leu Ser Trp Arg Leu Thr Asn Asp Thr Lys Thr Tyr
            750                 755                 760 cag gct gaa aag gct cga gga caa caa gcc tca ggc ata gca tgc tat      2355
Gln Ala Glu Lys Ala Arg Gly Gln Gln Ala Ser Gly Ile Ala Cys Tyr
        765                 770                 775 atg aag gat aat cca gga gca act gag gaa gat gcc att aag cac ata      2403
Met Lys Asp Asn Pro Gly Ala Thr Glu Glu Asp Ala Ile Lys His Ile
780                 785                 790 tgt cgt gtt gtt gat cgg gcc ttg aaa gaa gca agc ttt gaa tat ttc      2451
Cys Arg Val Val Asp Arg Ala Leu Lys Glu Ala Ser Phe Glu Tyr Phe
795                 800                 805                 810 aaa cca tcc aat gat atc cca atg ggt tgc aag tcc ttt att ttt aac      2499
Lys Pro Ser Asn Asp Ile Pro Met Gly Cys Lys Ser Phe Ile Phe Asn
                815                 820                 825 ctt aga ttg tgt gtc caa atc ttt tac aag ttt ata gat ggg tac gga      2547
Leu Arg Leu Cys Val Gln Ile Phe Tyr Lys Phe Ile Asp Gly Tyr Gly
            830                 835                 840 atc gcc aat gag gag att aag gac tat ata aga aaa gtt tat att gat      2595
Ile Ala Asn Glu Glu Ile Lys Asp Tyr Ile Arg Lys Val Tyr Ile Asp
        845                 850                 855 cca att caa gta tga tatatcatgt aaaacctctt tttcatgata aattgactta     2650
Pro Ile Gln Val
        860 ttattgtatt ggcaaaaaaa aaaaaaaaaa aaaaaaaaaa aaaaaaaaaa              2700

<210> SEQ ID NO 20
<211> LENGTH: 862
<212> TYPE: PRT
<213> ORGANISM: Taxus brevifolia

<400> SEQUENCE: 20

Met Ala Gln Leu Ser Phe Asn Ala Ala Leu Lys Met Asn Ala Leu Gly
```

-continued

```
1               5                   10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
            35                  40                  45

Ser Arg Gly Ser Gly Gly Pro Gly Pro Val Val Met Met Ser Ser Ser
50                          55                  60

Thr Gly Thr Ser Lys Val Val Ser Glu Thr Ser Ser Thr Ile Val Asp
65                      70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Lys Ile Lys Asp Met Phe Asn
            115                 120                 125

Ala Leu Gly Asp Gly Asp Ile Ser Pro Ser Ala Tyr Asp Thr Ala Trp
            130                 135                 140

Val Ala Arg Leu Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175

Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
            195                 200                 205

Gln Val Gln Gln Gly Ala Glu Phe Ile Ala Glu Asn Leu Arg Leu Leu
            210                 215                 220

Asn Glu Glu Asp Glu Leu Ser Pro Asp Phe Gln Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Tyr Leu Ser Thr Thr Arg Glu Ala Arg Leu Thr Asp
                260                 265                 270

Val Ser Ala Ala Asp Asn Ile Pro Ala Asn Met Leu Asn Ala Leu
                275                 280                 285

Glu Gly Leu Glu Glu Val Ile Asp Trp Asn Lys Ile Met Arg Phe Gln
290                 295                 300

Ser Lys Asp Gly Ser Phe Leu Ser Pro Ala Ser Thr Ala Cys Val
305                 310                 315                 320

Leu Met Asn Thr Gly Asp Glu Lys Cys Phe Thr Phe Leu Asn Asn Leu
                325                 330                 335

Leu Asp Lys Phe Gly Gly Cys Val Pro Cys Met Tyr Ser Ile Asp Leu
                340                 345                 350

Leu Glu Arg Leu Ser Leu Val Asp Asn Ile Glu His Leu Gly Ile Gly
                355                 360                 365

Arg His Phe Lys Gln Glu Ile Lys Gly Ala Leu Asp Tyr Val Tyr Arg
            370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Met His Gly
                405                 410                 415

Tyr Asn Val Ser Ser Asp Val Leu Asn Asn Phe Lys Asp Glu Asn Gly
            420                 425                 430
```

```
Arg Phe Phe Ser Ser Ala Gly Gln Thr His Val Glu Leu Arg Ser Val
            435                 440                 445

Val Asn Leu Phe Arg Ala Ser Asp Leu Ala Phe Pro Asp Glu Arg Ala
    450                 455                 460

Met Asp Asp Ala Arg Lys Phe Ala Glu Pro Tyr Leu Arg Glu Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Leu Glu Ala Arg
                500                 505                 510

Ser Tyr Ile Asp Ser Tyr Asp Asn Tyr Val Trp Gln Arg Lys Thr
            515                 520                 525

Leu Tyr Arg Met Pro Ser Leu Ser Asn Ser Lys Cys Leu Glu Leu Ala
    530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
            595                 600                 605

Gln Val Leu Phe Asp Asp Met Ala Asp Ile Phe Ala Thr Leu Asp Glu
    610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
            660                 665                 670

Met Leu Ala His Ile Arg Lys Pro Trp Glu Leu Tyr Phe Asn Cys Tyr
            675                 680                 685

Val Gln Glu Arg Glu Trp Leu Glu Ala Gly Tyr Ile Pro Thr Phe Glu
    690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
            755                 760                 765

Gly Gln Gln Ala Ser Gly Ile Ala Cys Tyr Met Lys Asp Asn Pro Gly
    770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
            820                 825                 830

Ile Phe Tyr Lys Phe Ile Asp Gly Tyr Gly Ile Ala Asn Glu Glu Ile
            835                 840                 845
```

```
                            Lys Asp Tyr Ile Arg Lys Val Tyr Ile Asp Pro Ile Gln Val
                                850                 855                 860

<210> SEQ ID NO 21
<211> LENGTH: 1419
<212> TYPE: DNA
<213> ORGANISM: Taxus cuspidata
<220> FEATURE:
<221> NAME/KEY: CDS
<222> LOCATION: (11)..(1330)
<223> OTHER INFORMATION: coding sequence

<400> SEQUENCE: 21
cacagttaga atg gag aag aca gat tta cac gta aat ctg att gag aaa            49
            Met Glu Lys Thr Asp Leu His Val Asn Leu Ile Glu Lys
                1               5                   10 gtg atg gtt ggg cca tcc ccg cct ctg ccc aaa acc acc ctg caa ctc           97
Val Met Val Gly Pro Ser Pro Pro Leu Pro Lys Thr Thr Leu Gln Leu
 15              20                  25 tcc tcc ata gac aac ctg cca ggg gta aga gga agc att ttc aat gcc          145
Ser Ser Ile Asp Asn Leu Pro Gly Val Arg Gly Ser Ile Phe Asn Ala
 30              35                  40                  45 ttg tta att tac aat gcc tct ccc tct ccc acc atg atc tct gca gat          193
Leu Leu Ile Tyr Asn Ala Ser Pro Ser Pro Thr Met Ile Ser Ala Asp
             50                  55                  60 cct gca aaa cca att aga gaa gct ctc gcc aag atc ctg gtt tat tat          241
Pro Ala Lys Pro Ile Arg Glu Ala Leu Ala Lys Ile Leu Val Tyr Tyr
         65                  70                  75 ccc cct ttt gct ggg cgc ctc aga gag aca gaa aat ggg gat ctg gaa          289
Pro Pro Phe Ala Gly Arg Leu Arg Glu Thr Glu Asn Gly Asp Leu Glu
     80                  85                  90 gtg gaa tgc aca ggg gag ggt gct atg ttt ttg gaa gcc atg gca gac          337
Val Glu Cys Thr Gly Glu Gly Ala Met Phe Leu Glu Ala Met Ala Asp
 95                 100                 105 aat gag ctg tct gtg ttg gga gat ttt gat gac agc aat cca tca ttt          385
Asn Glu Leu Ser Val Leu Gly Asp Phe Asp Asp Ser Asn Pro Ser Phe
110                 115                 120                 125 cag cag cta ctt ttt tcg ctt cca ctc gat acc aat ttc aaa gac ctc          433
Gln Gln Leu Leu Phe Ser Leu Pro Leu Asp Thr Asn Phe Lys Asp Leu
                130                 135                 140 tct ctt ctg gtt gtt cag gta act cgt ttt aca tgt gga ggc ttt gtt          481
Ser Leu Leu Val Val Gln Val Thr Arg Phe Thr Cys Gly Gly Phe Val
            145                 150                 155 gtt gga gtg agt ttc cac cat ggt gta tgt gat ggt cga gga gcg gcc          529
Val Gly Val Ser Phe His His Gly Val Cys Asp Gly Arg Gly Ala Ala
        160                 165                 170 caa ttt ctt aaa ggt ttg gca gag atg gca cgg gga gag gtt aag ctc          577
Gln Phe Leu Lys Gly Leu Ala Glu Met Ala Arg Gly Glu Val Lys Leu
    175                 180                 185 tca ttg gaa cca ata tgg aat agg gaa cta gtg aag ctt gat gac cct          625
Ser Leu Glu Pro Ile Trp Asn Arg Glu Leu Val Lys Leu Asp Asp Pro
190                 195                 200                 205 aaa tac ctt caa ttt ttt cac ttt gaa ttc cta cga gcg cct tca att          673
Lys Tyr Leu Gln Phe Phe His Phe Glu Phe Leu Arg Ala Pro Ser Ile
                210                 215                 220 gtt gag aaa att gtt caa aca tat ttt att ata gat ttt gag acc ata          721
Val Glu Lys Ile Val Gln Thr Tyr Phe Ile Ile Asp Phe Glu Thr Ile
            225                 230                 235 aat tat atc aaa caa tct gtt atg gaa gaa tgt aaa gaa ttt tgc tct          769
Asn Tyr Ile Lys Gln Ser Val Met Glu Glu Cys Lys Glu Phe Cys Ser
        240                 245                 250
```

```
tca ttc gaa gtt gca tca gca atg act tgg ata gca agg aca aga gct      817
Ser Phe Glu Val Ala Ser Ala Met Thr Trp Ile Ala Arg Thr Arg Ala
    255                 260                 265 ttt caa att cca gaa agt gag tac gtg aaa att ctc ttc gga atg gac      865
Phe Gln Ile Pro Glu Ser Glu Tyr Val Lys Ile Leu Phe Gly Met Asp
270                 275                 280                 285 atg agg aac tca ttt aat ccc cct ctt cca agc gga tac tat ggt aac      913
Met Arg Asn Ser Phe Asn Pro Pro Leu Pro Ser Gly Tyr Tyr Gly Asn
                290                 295                 300 tcc att ggt acc gca tgt gca gtg gat aat gtt caa gac ctc tta agt      961
Ser Ile Gly Thr Ala Cys Ala Val Asp Asn Val Gln Asp Leu Leu Ser
                    305                 310                 315 gga tct ctt ttg cgt gct ata atg att ata aag aaa tca aag gtc tct     1009
Gly Ser Leu Leu Arg Ala Ile Met Ile Ile Lys Lys Ser Lys Val Ser
320                 325                 330 tta aat gat aat ttc aag tca aga gct gtg gtg aag cca tct gaa ttg     1057
Leu Asn Asp Asn Phe Lys Ser Arg Ala Val Val Lys Pro Ser Glu Leu
335                 340                 345 gat gtg aat atg aat cat gaa aac gta gtt gca ttt gct gat tgg agc     1105
Asp Val Asn Met Asn His Glu Asn Val Val Ala Phe Ala Asp Trp Ser
350                 355                 360                 365 cga ttg gga ttt gat gaa gtg gat ttt ggt tgg ggg aat gcg gtg agt     1153
Arg Leu Gly Phe Asp Glu Val Asp Phe Gly Trp Gly Asn Ala Val Ser
                370                 375                 380 gta agc cct gtg caa caa cag tct gcg tta gca atg caa aat tat ttt     1201
Val Ser Pro Val Gln Gln Gln Ser Ala Leu Ala Met Gln Asn Tyr Phe
                    385                 390                 395 ctt ttc cta aaa cct tcc aag aac aag ccc gat gga atc aaa ata tta     1249
Leu Phe Leu Lys Pro Ser Lys Asn Lys Pro Asp Gly Ile Lys Ile Leu
                400                 405                 410 atg ttt ctg ccc cta tca aaa atg aag tca ttc aaa att gaa atg gaa     1297
Met Phe Leu Pro Leu Ser Lys Met Lys Ser Phe Lys Ile Glu Met Glu
415                 420                 425 gcc atg atg aaa aaa tat gtg gct aaa gta tga aagtgcaacg atggaaggct   1350
Ala Met Met Lys Lys Tyr Val Ala Lys Val
430                 435 tgtattttgg aaataatatt tcaaataatc tcgtggttca atactttgt taaaaaaaaa    1410 aaaaaaaaa                                                           1419

<210> SEQ ID NO 22
<211> LENGTH: 439
<212> TYPE: PRT
<213> ORGANISM: Taxus cuspidata

<400> SEQUENCE: 22

Met Glu Lys Thr Asp Leu His Val Asn Leu Ile Glu Lys Val Met Val
1               5                   10                  15

Gly Pro Ser Pro Pro Leu Pro Lys Thr Thr Leu Gln Leu Ser Ser Ile
                20                  25                  30

Asp Asn Leu Pro Gly Val Arg Gly Ser Ile Phe Asn Ala Leu Leu Ile
            35                  40                  45

Tyr Asn Ala Ser Pro Ser Pro Thr Met Ile Ser Ala Asp Pro Ala Lys
        50                  55                  60

Pro Ile Arg Glu Ala Leu Ala Lys Ile Leu Val Tyr Tyr Pro Pro Phe
65                  70                  75                  80

Ala Gly Arg Leu Arg Glu Thr Glu Asn Gly Asp Leu Glu Val Glu Cys
                85                  90                  95

Thr Gly Glu Gly Ala Met Phe Leu Glu Ala Met Ala Asp Asn Glu Leu
```

```
                100                 105                 110
Ser Val Leu Gly Asp Phe Asp Asp Ser Asn Pro Ser Phe Gln Gln Leu
            115                 120                 125

Leu Phe Ser Leu Pro Leu Asp Thr Asn Phe Lys Asp Leu Ser Leu Leu
130                 135                 140

Val Val Gln Val Thr Arg Phe Thr Cys Gly Gly Phe Val Val Gly Val
145                 150                 155                 160

Ser Phe His His Gly Val Cys Asp Gly Arg Gly Ala Ala Gln Phe Leu
                165                 170                 175

Lys Gly Leu Ala Glu Met Ala Arg Gly Glu Val Lys Leu Ser Leu Glu
            180                 185                 190

Pro Ile Trp Asn Arg Glu Leu Val Lys Leu Asp Asp Pro Lys Tyr Leu
        195                 200                 205

Gln Phe Phe His Phe Glu Phe Leu Arg Ala Pro Ser Ile Val Glu Lys
    210                 215                 220

Ile Val Gln Thr Tyr Phe Ile Ile Asp Phe Glu Thr Ile Asn Tyr Ile
225                 230                 235                 240

Lys Gln Ser Val Met Glu Glu Cys Lys Glu Phe Cys Ser Ser Phe Glu
                245                 250                 255

Val Ala Ser Ala Met Thr Trp Ile Ala Arg Thr Arg Ala Phe Gln Ile
            260                 265                 270

Pro Glu Ser Glu Tyr Val Lys Ile Leu Phe Gly Met Asp Met Arg Asn
        275                 280                 285

Ser Phe Asn Pro Pro Leu Pro Ser Gly Tyr Tyr Gly Asn Ser Ile Gly
    290                 295                 300

Thr Ala Cys Ala Val Asp Asn Val Gln Asp Leu Leu Ser Gly Ser Leu
305                 310                 315                 320

Leu Arg Ala Ile Met Ile Ile Lys Lys Ser Lys Val Ser Leu Asn Asp
                325                 330                 335

Asn Phe Lys Ser Arg Ala Val Val Lys Pro Ser Glu Leu Asp Val Asn
            340                 345                 350

Met Asn His Glu Asn Val Val Ala Phe Ala Asp Trp Ser Arg Leu Gly
        355                 360                 365

Phe Asp Glu Val Asp Phe Gly Trp Gly Asn Ala Val Ser Val Ser Pro
    370                 375                 380

Val Gln Gln Gln Ser Ala Leu Ala Met Gln Asn Tyr Phe Leu Phe Leu
385                 390                 395                 400

Lys Pro Ser Lys Asn Lys Pro Asp Gly Ile Lys Ile Leu Met Phe Leu
                405                 410                 415

Pro Leu Ser Lys Met Lys Ser Phe Lys Ile Glu Met Glu Ala Met Met
            420                 425                 430

Lys Lys Tyr Val Ala Lys Val
        435

<210> SEQ ID NO 23
<211> LENGTH: 1388
<212> TYPE: DNA
<213> ORGANISM: Taxus cuspidata
<220> FEATURE:
<221> NAME/KEY: CDS
<222> LOCATION: (22)..(1344)
<223> OTHER INFORMATION: coding sequence

<400> SEQUENCE: 23
aggagagtcc aaatatctac a atg ggc agg ttc aat gta gat atg att gag      51
                        Met Gly Arg Phe Asn Val Asp Met Ile Glu
```

-continued

```
              1               5              10
cga gtg atc gtg gcg cca tgc ctt caa tcg ccc aaa aat atc ctg cac    99
Arg Val Ile Val Ala Pro Cys Leu Gln Ser Pro Lys Asn Ile Leu His
                15              20              25 ctc tcc ccc att gac aac aaa act aga gga cta acc aac ata tta tca   147
Leu Ser Pro Ile Asp Asn Lys Thr Arg Gly Leu Thr Asn Ile Leu Ser
        30              35              40 gtc tac aat gcc tcc cag aga gtt tct gtt tct gca gat cct gca aaa   195
Val Tyr Asn Ala Ser Gln Arg Val Ser Val Ser Ala Asp Pro Ala Lys
            45              50              55 aca att cga gag gct ctc tcc aag gtg ctg gtt tat tat ccc cct ttt   243
Thr Ile Arg Glu Ala Leu Ser Lys Val Leu Val Tyr Tyr Pro Pro Phe
        60              65              70 gct gga agg ctg aga aac aca gaa aat ggg gat ctt gaa gtg gag tgc   291
Ala Gly Arg Leu Arg Asn Thr Glu Asn Gly Asp Leu Glu Val Glu Cys
75              80              85              90 aca ggg gag ggt gcc gtc ttt gtg gaa gcc atg gcg gac aac gac ctt   339
Thr Gly Glu Gly Ala Val Phe Val Glu Ala Met Ala Asp Asn Asp Leu
            95             100             105 tca gta tta caa gat ttc aat gag tac gat cca tca ttt cag cag cta   387
Ser Val Leu Gln Asp Phe Asn Glu Tyr Asp Pro Ser Phe Gln Gln Leu
        110             115             120 gtt ttt aat ctt cga gag gat gtc aat att gag gac ctc cat ctt cta   435
Val Phe Asn Leu Arg Glu Asp Val Asn Ile Glu Asp Leu His Leu Leu
        125             130             135 act gtt cag gta act cgt ttt aca tgt gga gga ttt gtt gtg ggc aca   483
Thr Val Gln Val Thr Arg Phe Thr Cys Gly Gly Phe Val Val Gly Thr
    140             145             150 aga ttc cac cat agt gta tct gat gga aaa gga atc ggc cag tta ctt   531
Arg Phe His His Ser Val Ser Asp Gly Lys Gly Ile Gly Gln Leu Leu
155             160             165             170 aaa ggc atg gga gag atg gca agg ggg gag ttt aag ccc tcg tta gaa   579
Lys Gly Met Gly Glu Met Ala Arg Gly Glu Phe Lys Pro Ser Leu Glu
            175             180             185 cca ata tgg aat aga gaa atg gtg aag cct gaa gac att atg tac ctc   627
Pro Ile Trp Asn Arg Glu Met Val Lys Pro Glu Asp Ile Met Tyr Leu
        190             195             200 cag ttt gat cac ttt gat ttc ata cac cca cct ctt aat ctt gag aag   675
Gln Phe Asp His Phe Asp Phe Ile His Pro Pro Leu Asn Leu Glu Lys
    205             210             215 tct att caa gca tct atg gta ata agc ttt gag aga ata aat tat atc   723
Ser Ile Gln Ala Ser Met Val Ile Ser Phe Glu Arg Ile Asn Tyr Ile
    220             225             230 aaa cga tgc atg atg gaa gaa tgc aaa gaa ttt ttt tct gca ttt gaa   771
Lys Arg Cys Met Met Glu Glu Cys Lys Glu Phe Phe Ser Ala Phe Glu
235             240             245             250 gtt gta gta gca ttg att tgg ctg gca agg aca aag tct ttt cga att   819
Val Val Val Ala Leu Ile Trp Leu Ala Arg Thr Lys Ser Phe Arg Ile
            255             260             265 cca ccc aat gag tat gtg aaa att atc ttt cca atc gac atg agg aat   867
Pro Pro Asn Glu Tyr Val Lys Ile Ile Phe Pro Ile Asp Met Arg Asn
        270             275             280 tca ttt gac tcc cct ctt cca aag gga tac tat ggt aat gct att ggt   915
Ser Phe Asp Ser Pro Leu Pro Lys Gly Tyr Tyr Gly Asn Ala Ile Gly
    285             290             295 aat gca tgt gca atg gat aat gtc aaa gac ctc tta aat gga tct ctt   963
Asn Ala Cys Ala Met Asp Asn Val Lys Asp Leu Leu Asn Gly Ser Leu
300             305             310 tta tat gct cta atg ctt ata aag aaa tca aag ttt gct tta aat gag  1011
```

```
Leu Tyr Ala Leu Met Leu Ile Lys Lys Ser Lys Phe Ala Leu Asn Glu
315                 320                 325                 330 aat ttc aaa tca aga atc ttg aca aaa cca tct aca tta gat gcg aat       1059
Asn Phe Lys Ser Arg Ile Leu Thr Lys Pro Ser Thr Leu Asp Ala Asn
                335                 340                 345 atg aag cat gaa aat gta gtc gga tgt ggc gat tgg agg aat ttg gga       1107
Met Lys His Glu Asn Val Val Gly Cys Gly Asp Trp Arg Asn Leu Gly
            350                 355                 360 ttt tat gaa gca gat ttt gga tgg gga aat gca gtg aat gta agc ccc       1155
Phe Tyr Glu Ala Asp Phe Gly Trp Gly Asn Ala Val Asn Val Ser Pro
        365                 370                 375 atg cag caa caa aga gag cat gaa tta gct atg caa aat tat ttt ctt       1203
Met Gln Gln Gln Arg Glu His Glu Leu Ala Met Gln Asn Tyr Phe Leu
    380                 385                 390 ttt ctc cga tca gct aag aac atg att gat gga atc aag ata cta atg       1251
Phe Leu Arg Ser Ala Lys Asn Met Ile Asp Gly Ile Lys Ile Leu Met
395                 400                 405                 410 ttc atg cct gca tca atg gtg aaa cca ttc aaa att gaa atg gaa gtc       1299
Phe Met Pro Ala Ser Met Val Lys Pro Phe Lys Ile Glu Met Glu Val
                415                 420                 425 aca ata aac aaa tat gtg gct aaa ata tgt aac tct aag tta taa           1344
Thr Ile Asn Lys Tyr Val Ala Lys Ile Cys Asn Ser Lys Leu
                430                 435                 440 agtatgtatg actgcaaaat agtaaaatat tgcatggtgg atgc                      1388

<210> SEQ ID NO 24
<211> LENGTH: 440
<212> TYPE: PRT
<213> ORGANISM: Taxus cuspidata

<400> SEQUENCE: 24

Met Gly Arg Phe Asn Val Asp Met Ile Glu Arg Val Ile Val Ala Pro
1               5                   10                  15

Cys Leu Gln Ser Pro Lys Asn Ile Leu His Leu Ser Pro Ile Asp Asn
                20                  25                  30

Lys Thr Arg Gly Leu Thr Asn Ile Leu Ser Val Tyr Asn Ala Ser Gln
            35                  40                  45

Arg Val Ser Val Ser Ala Asp Pro Ala Lys Thr Ile Arg Glu Ala Leu
        50                  55                  60

Ser Lys Val Leu Val Tyr Tyr Pro Pro Phe Ala Gly Arg Leu Arg Asn
65                  70                  75                  80

Thr Glu Asn Gly Asp Leu Glu Val Glu Cys Thr Gly Glu Gly Ala Val
                85                  90                  95

Phe Val Glu Ala Met Ala Asp Asn Asp Leu Ser Val Leu Gln Asp Phe
            100                 105                 110

Asn Glu Tyr Asp Pro Ser Phe Gln Gln Leu Val Phe Asn Leu Arg Glu
        115                 120                 125

Asp Val Asn Ile Glu Asp Leu His Leu Leu Thr Val Gln Val Thr Arg
130                 135                 140

Phe Thr Cys Gly Gly Phe Val Val Gly Thr Arg Phe His His Ser Val
145                 150                 155                 160

Ser Asp Gly Lys Gly Ile Gly Gln Leu Leu Lys Gly Met Gly Glu Met
                165                 170                 175

Ala Arg Gly Glu Phe Lys Pro Ser Leu Glu Pro Ile Trp Asn Arg Glu
            180                 185                 190

Met Val Lys Pro Glu Asp Ile Met Tyr Leu Gln Phe Asp His Phe Asp
        195                 200                 205
```

```
Phe Ile His Pro Pro Leu Asn Leu Glu Lys Ser Ile Gln Ala Ser Met
        210                 215                 220

Val Ile Ser Phe Glu Arg Ile Asn Tyr Ile Lys Arg Cys Met Met Glu
225                 230                 235                 240

Glu Cys Lys Glu Phe Phe Ser Ala Phe Glu Val Val Ala Leu Ile
                245                 250                 255

Trp Leu Ala Arg Thr Lys Ser Phe Arg Ile Pro Pro Asn Glu Tyr Val
            260                 265                 270

Lys Ile Ile Phe Pro Ile Asp Met Arg Asn Ser Phe Asp Ser Pro Leu
        275                 280                 285

Pro Lys Gly Tyr Tyr Gly Asn Ala Ile Gly Asn Ala Cys Ala Met Asp
        290                 295                 300

Asn Val Lys Asp Leu Leu Asn Gly Ser Leu Leu Tyr Ala Leu Met Leu
305                 310                 315                 320

Ile Lys Lys Ser Lys Phe Ala Leu Asn Glu Asn Phe Lys Ser Arg Ile
                325                 330                 335

Leu Thr Lys Pro Ser Thr Leu Asp Ala Asn Met Lys His Glu Asn Val
            340                 345                 350

Val Gly Cys Gly Asp Trp Arg Asn Leu Gly Phe Tyr Glu Ala Asp Phe
        355                 360                 365

Gly Trp Gly Asn Ala Val Asn Val Ser Pro Met Gln Gln Gln Arg Glu
        370                 375                 380

His Glu Leu Ala Met Gln Asn Tyr Phe Leu Phe Leu Arg Ser Ala Lys
385                 390                 395                 400

Asn Met Ile Asp Gly Ile Lys Ile Leu Met Phe Met Pro Ala Ser Met
                405                 410                 415

Val Lys Pro Phe Lys Ile Glu Met Glu Val Thr Ile Asn Lys Tyr Val
            420                 425                 430

Ala Lys Ile Cys Asn Ser Lys Leu
        435                 440

<210> SEQ ID NO 25
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (14)..(14)
<223> OTHER INFORMATION: I

<400> SEQUENCE: 25
ttymgnccna gmgnttygar                                              20

<210> SEQ ID NO 26
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
```

```
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (15)..(15)
<223> OTHER INFORMATION: I

<400> SEQUENCE: 26
ttymgnccnt cnmgnttyga r                                             21

<210> SEQ ID NO 27
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (3)..(6)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (18)..(18)
<223> OTHER INFORMATION: I

<400> SEQUENCE: 27
cknnnnccng cnccraangg                                               20

<210> SEQ ID NO 28
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (15)..(15)
<223> OTHER INFORMATION: I

<400> SEQUENCE: 28
gargarttym gnccngarmg                                               20

<210> SEQ ID NO 29
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (10)..(12)
<223> OTHER INFORMATION: I
<220> FEATURE:
```

<221> NAME/KEY: modified_base
<222> LOCATION: (15)..(15)
<223> OTHER INFORMATION: I
<220> FEATURE:
<221> NAME/KEY: modified_base
<222> LOCATION: (18)..(18)
<223> OTHER INFORMATION: I

<400> SEQUENCE: 29
garaarttyn nnccnganar gtty                                          24

<210> SEQ ID NO 30
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)..(9)
<223> OTHER INFORMATION: I
<220> FEATURE:
<221> NAME/KEY: modified_base
<222> LOCATION: (12)..(15)
<223> OTHER INFORMATION: I
<220> FEATURE:
<221> NAME/KEY: modified_base
<222> LOCATION: (18)..(18)
<223> OTHER INFORMATION: I
<220> FEATURE:
<221> NAME/KEY: modified_base
<222> LOCATION: (21)..(21)
<223> OTHER INFORMATION: I
<220> FEATURE:
<221> NAME/KEY: modified_base
<222> LOCATION: (27)..(27)
<223> OTHER INFORMATION: I

<400> SEQUENCE: 30
ggrcannnnc knnnnccncc nccraangg                                     29

<210> SEQ ID NO 31
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (18)..(18)
<223> OTHER INFORMATION: I
<220> FEATURE:
<221> NAME/KEY: modified_base
<222> LOCATION: (21)..(21)
<223> OTHER INFORMATION: I
<220> FEATURE:
<221> NAME/KEY: modified_base
<222> LOCATION: (24)..(24)
<223> OTHER INFORMATION: I
<220> FEATURE:
<221> NAME/KEY: modified_base
<222> LOCATION: (30)..(30)
<223> OTHER INFORMATION: I

```
<400> SEQUENCE: 31
ccnggrcana tnmkyytncc ngcnccraan gg                                  32

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
atggacgccc tgtataagag                                                20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tcaattgact atggtctcgg                                                20

<210> SEQ ID NO 34
<211> LENGTH: 1488
<212> TYPE: DNA
<213> ORGANISM: Taxus cuspidata
<220> FEATURE:
<221> NAME/KEY: CDS
<222> LOCATION: (24)..(1346)
<223> OTHER INFORMATION: coding sequence

<400> SEQUENCE: 34
gcaccagctg agcttgatct gag atg gca ggc tca aca gaa ttt gtg gta aga      53
                         Met Ala Gly Ser Thr Glu Phe Val Val Arg
                          1               5                  10 agc tta gag aga gtg atg gtg gct cca agc cag cca tcg ccc aaa gct      101
Ser Leu Glu Arg Val Met Val Ala Pro Ser Gln Pro Ser Pro Lys Ala
             15                  20                  25 ttc ctg cag ctc tcc acc ctt gac aat cta cca ggg gtg aga gaa aac      149
Phe Leu Gln Leu Ser Thr Leu Asp Asn Leu Pro Gly Val Arg Glu Asn
         30                  35                  40 att ttt aac acc ttg tta gtc tac aat gcc tca gac aga gtt tcc gta      197
Ile Phe Asn Thr Leu Leu Val Tyr Asn Ala Ser Asp Arg Val Ser Val
     45                  50                  55 gat cct gca aaa gta att cgg cag gct ctc tcc aag gtg ttg gtg tac      245
Asp Pro Ala Lys Val Ile Arg Gln Ala Leu Ser Lys Val Leu Val Tyr
 60                  65                  70 tat tcc cct ttt gca ggg cgt ctc agg aaa aaa gaa aat gga gat ctt      293
Tyr Ser Pro Phe Ala Gly Arg Leu Arg Lys Lys Glu Asn Gly Asp Leu
75                  80                  85                  90 gaa gtg gag tgc aca ggg gag ggt gct ctg ttt gtg gaa gcc atg gct      341
Glu Val Glu Cys Thr Gly Glu Gly Ala Leu Phe Val Glu Ala Met Ala
                 95                 100                 105 gac act gac ctc tca gtc tta gga gat ttg gat gac tac agt cct tca      389
Asp Thr Asp Leu Ser Val Leu Gly Asp Leu Asp Asp Tyr Ser Pro Ser
            110                 115                 120 ctt gag caa cta ctt ttt tgt ctt ccg cct gat aca gat att gag gac      437
Leu Glu Gln Leu Leu Phe Cys Leu Pro Pro Asp Thr Asp Ile Glu Asp
        125                 130                 135 atc cat cct ctg gtg gtt cag gta act cgt ttt aca tgt gga ggt ttt      485
Ile His Pro Leu Val Val Gln Val Thr Arg Phe Thr Cys Gly Gly Phe
```

```
                140                 145                 150
gtt gta ggg gtg agt ttc tgc cat ggt ata tgt gat gga cta gga gca    533
Val Val Gly Val Ser Phe Cys His Gly Ile Cys Asp Gly Leu Gly Ala
155                 160                 165                 170 ggc cag ttt ctt ata gcc atg gga gag atg gca agg gga gag att aag    581
Gly Gln Phe Leu Ile Ala Met Gly Glu Met Ala Arg Gly Glu Ile Lys
                175                 180                 185 ccc tcc tcg gag cca ata tgg aag aga gaa ttg ctg aag ccg gaa gac    629
Pro Ser Ser Glu Pro Ile Trp Lys Arg Glu Leu Leu Lys Pro Glu Asp
            190                 195                 200 cct tta tac cgg ttc cag tat tat cac ttt caa ttg att tgc ccg cct    677
Pro Leu Tyr Arg Phe Gln Tyr Tyr His Phe Gln Leu Ile Cys Pro Pro
        205                 210                 215 tca aca ttc ggg aaa ata gtt caa gga tct ctt gtt ata acc tct gag    725
Ser Thr Phe Gly Lys Ile Val Gln Gly Ser Leu Val Ile Thr Ser Glu
    220                 225                 230 aca ata aat tgt atc aaa caa tgc ctt agg gaa gaa agt aaa gaa ttt    773
Thr Ile Asn Cys Ile Lys Gln Cys Leu Arg Glu Glu Ser Lys Glu Phe
235                 240                 245                 250 tgc tct gcg ttc gaa gtt gta tct gca ttg gct tgg ata gca agg aca    821
Cys Ser Ala Phe Glu Val Val Ser Ala Leu Ala Trp Ile Ala Arg Thr
                255                 260                 265 agg gct ctt caa att cca cat agt gag aat gtg aag ctt att ttt gca    869
Arg Ala Leu Gln Ile Pro His Ser Glu Asn Val Lys Leu Ile Phe Ala
            270                 275                 280 atg gac atg aga aaa tta ttt aat cca cca ctt tcg aag gga tac tac    917
Met Asp Met Arg Lys Leu Phe Asn Pro Pro Leu Ser Lys Gly Tyr Tyr
        285                 290                 295 ggt aat ttt gtt ggt acc gta tgt gca atg gat aat gtc aag gac cta    965
Gly Asn Phe Val Gly Thr Val Cys Ala Met Asp Asn Val Lys Asp Leu
    300                 305                 310 tta agt gga tct ctt ttg cgt gtt gta agg att ata aag aaa gca aag   1013
Leu Ser Gly Ser Leu Leu Arg Val Val Arg Ile Ile Lys Lys Ala Lys
315                 320                 325                 330 gtc tct tta aat gag cat ttc acg tca aca atc gtg aca ccc cgt tct   1061
Val Ser Leu Asn Glu His Phe Thr Ser Thr Ile Val Thr Pro Arg Ser
                335                 340                 345 gga tca gat gag agt atc aat tat gaa aac ata gtt gga ttt ggt gat   1109
Gly Ser Asp Glu Ser Ile Asn Tyr Glu Asn Ile Val Gly Phe Gly Asp
            350                 355                 360 cga agg cga ttg gga ttt gat gaa gta gac ttt ggg tgg ggg cat gca   1157
Arg Arg Arg Leu Gly Phe Asp Glu Val Asp Phe Gly Trp Gly His Ala
        365                 370                 375 gat aat gta agt ctc gtg caa cat gga ttg aag gat gtt tca gtc gtg   1205
Asp Asn Val Ser Leu Val Gln His Gly Leu Lys Asp Val Ser Val Val
    380                 385                 390 caa agt tat ttt ctt ttc ata cga cct ccc aag aat aac ccc gat gga   1253
Gln Ser Tyr Phe Leu Phe Ile Arg Pro Pro Lys Asn Asn Pro Asp Gly
395                 400                 405                 410 atc aag atc cta tcg ttc atg ccc ccg tca ata gtg aaa tcc ttc aaa   1301
Ile Lys Ile Leu Ser Phe Met Pro Pro Ser Ile Val Lys Ser Phe Lys
                415                 420                 425 ttt gaa atg gaa acc atg aca aac aaa tat gta act aag cct tga       1346
Phe Glu Met Glu Thr Met Thr Asn Lys Tyr Val Thr Lys Pro
            430                 435                 440 aattgtagta acttaagcct tgcattttca gaataagttt tggcactggg ttgtggttga  1406
agtaatgtac ttttgaattt tgatttaaag ttctattcaa agttataaaa tgtattatgt  1466
gaaaatatgt tgcaattatg gt                                          1488
```

<210> SEQ ID NO 35
<211> LENGTH: 440
<212> TYPE: PRT
<213> ORGANISM: Taxus cuspidata

<400> SEQUENCE: 35

```
Met Ala Gly Ser Thr Glu Phe Val Val Arg Ser Leu Glu Arg Val Met
1               5                   10                  15

Val Ala Pro Ser Gln Pro Ser Pro Lys Ala Phe Leu Gln Leu Ser Thr
            20                  25                  30

Leu Asp Asn Leu Pro Gly Val Arg Glu Asn Ile Phe Asn Thr Leu Leu
        35                  40                  45

Val Tyr Asn Ala Ser Asp Arg Val Ser Val Asp Pro Ala Lys Val Ile
    50                  55                  60

Arg Gln Ala Leu Ser Lys Val Leu Val Tyr Tyr Ser Pro Phe Ala Gly
65                  70                  75                  80

Arg Leu Arg Lys Lys Glu Asn Gly Asp Leu Glu Val Glu Cys Thr Gly
                85                  90                  95

Glu Gly Ala Leu Phe Val Glu Ala Met Ala Asp Thr Asp Leu Ser Val
            100                 105                 110

Leu Gly Asp Leu Asp Asp Tyr Ser Pro Ser Leu Glu Gln Leu Leu Phe
        115                 120                 125

Cys Leu Pro Pro Asp Thr Asp Ile Glu Asp Ile His Pro Leu Val Val
    130                 135                 140

Gln Val Thr Arg Phe Thr Cys Gly Gly Phe Val Gly Val Ser Phe
145                 150                 155                 160

Cys His Gly Ile Cys Asp Gly Leu Gly Ala Gly Gln Phe Leu Ile Ala
                165                 170                 175

Met Gly Glu Met Ala Arg Gly Glu Ile Lys Pro Ser Ser Glu Pro Ile
            180                 185                 190

Trp Lys Arg Glu Leu Leu Lys Pro Glu Asp Pro Leu Tyr Arg Phe Gln
        195                 200                 205

Tyr Tyr His Phe Gln Leu Ile Cys Pro Pro Ser Thr Phe Gly Lys Ile
    210                 215                 220

Val Gln Gly Ser Leu Val Ile Thr Ser Glu Thr Ile Asn Cys Ile Lys
225                 230                 235                 240

Gln Cys Leu Arg Glu Glu Ser Lys Glu Phe Cys Ser Ala Phe Glu Val
                245                 250                 255

Val Ser Ala Leu Ala Trp Ile Ala Arg Thr Arg Ala Leu Gln Ile Pro
            260                 265                 270

His Ser Glu Asn Val Lys Leu Ile Phe Ala Met Asp Met Arg Lys Leu
        275                 280                 285

Phe Asn Pro Pro Leu Ser Lys Gly Tyr Tyr Gly Asn Phe Val Gly Thr
    290                 295                 300

Val Cys Ala Met Asp Asn Val Lys Asp Leu Leu Ser Gly Ser Leu Leu
305                 310                 315                 320

Arg Val Val Arg Ile Ile Lys Lys Ala Lys Val Ser Leu Asn Glu His
                325                 330                 335

Phe Thr Ser Thr Ile Val Thr Pro Arg Ser Gly Ser Asp Glu Ser Ile
            340                 345                 350

Asn Tyr Glu Asn Ile Val Gly Phe Gly Asp Arg Arg Leu Gly Phe
        355                 360                 365

Asp Glu Val Asp Phe Gly Trp Gly His Ala Asp Asn Val Ser Leu Val
```

```
                370                 375                 380
Gln His Gly Leu Lys Asp Val Ser Val Gln Ser Tyr Phe Leu Phe
385                 390                 395                 400

Ile Arg Pro Pro Lys Asn Asn Pro Asp Gly Ile Lys Ile Leu Ser Phe
                405                 410                 415

Met Pro Pro Ser Ile Val Lys Ser Phe Lys Phe Glu Met Glu Thr Met
                420                 425                 430

Thr Asn Lys Tyr Val Thr Lys Pro
                435                 440

<210> SEQ ID NO 36
<211> LENGTH: 1338
<212> TYPE: DNA
<213> ORGANISM: Taxus cuspidata
<220> FEATURE:
<221> NAME/KEY: CDS
<222> LOCATION: (1)..(1326)
<223> OTHER INFORMATION: coding sequence

<400> SEQUENCE: 36 atg aag aag aca ggt tcg ttt gca gag ttc cat gtg aat atg att gag      48
Met Lys Lys Thr Gly Ser Phe Ala Glu Phe His Val Asn Met Ile Glu
1               5                   10                  15 cga gtc atg gtg aga ccg tgc ctg cct tcg ccc aaa aca atc ctc cct      96
Arg Val Met Val Arg Pro Cys Leu Pro Ser Pro Lys Thr Ile Leu Pro
                20                  25                  30 ctc tcc gcc att gac aac atg gca aga gct ttt tct aac gta ttg ctg     144
Leu Ser Ala Ile Asp Asn Met Ala Arg Ala Phe Ser Asn Val Leu Leu
            35                  40                  45 gtc tac gct gcc aac atg gac aga gtc tct gca gat cct gca aaa gtg     192
Val Tyr Ala Ala Asn Met Asp Arg Val Ser Ala Asp Pro Ala Lys Val
        50                  55                  60 att cga gag gct ctc tcc aag gtg ctg gtt tat tat tac cct ttt gct     240
Ile Arg Glu Ala Leu Ser Lys Val Leu Val Tyr Tyr Tyr Pro Phe Ala
65                  70                  75                  80 ggg cgg ctc aga aat aaa gaa aat ggg gaa ctt gaa gtg gag tgc aca     288
Gly Arg Leu Arg Asn Lys Glu Asn Gly Glu Leu Glu Val Glu Cys Thr
                85                  90                  95 ggg cag ggt gtt ctg ttt ctg gaa gcc atg gct gac agc gac ctt tca     336
Gly Gln Gly Val Leu Phe Leu Glu Ala Met Ala Asp Ser Asp Leu Ser
            100                 105                 110 gtc tta aca gat ctg gat aac tac aat cca tcg ttt cag cag ttg att     384
Val Leu Thr Asp Leu Asp Asn Tyr Asn Pro Ser Phe Gln Gln Leu Ile
        115                 120                 125 ttt tct cta cca cag gat aca gat att gag gac ctc cat ctc ttg att     432
Phe Ser Leu Pro Gln Asp Thr Asp Ile Glu Asp Leu His Leu Leu Ile
    130                 135                 140 gtt cag gta act cgt ttt aca tgt ggg ggt ttt gtt gtg gga gcg aat     480
Val Gln Val Thr Arg Phe Thr Cys Gly Gly Phe Val Val Gly Ala Asn
145                 150                 155                 160 gtg tat ggt agt gca tgc gat gca aaa gga ttt ggc cag ttt ctt caa     528
Val Tyr Gly Ser Ala Cys Asp Ala Lys Gly Phe Gly Gln Phe Leu Gln
                165                 170                 175 agt atg gca gag atg gcg aga gga gag gtt aag ccc tcg att gaa ccg     576
Ser Met Ala Glu Met Ala Arg Gly Glu Val Lys Pro Ser Ile Glu Pro
            180                 185                 190 ata tgg aat aga gaa ctg gtg aag cta gaa cat tgt atg ccc ttc cgg     624
Ile Trp Asn Arg Glu Leu Val Lys Leu Glu His Cys Met Pro Phe Arg
        195                 200                 205 atg agt cat ctt caa att ata cat gca cct gta att gag gag aaa ttt     672
```

```
Met Ser His Leu Gln Ile Ile His Ala Pro Val Ile Glu Glu Lys Phe
    210                 215                 220 gtt caa aca tct ctt gtt ata aac ttt gag ata ata aat cat atc aga    720
Val Gln Thr Ser Leu Val Ile Asn Phe Glu Ile Ile Asn His Ile Arg
225                 230                 235                 240 cga cgc atc atg gaa gaa cgc aaa gaa agt tta tct tca ttt gaa att    768
Arg Arg Ile Met Glu Glu Arg Lys Glu Ser Leu Ser Ser Phe Glu Ile
                245                 250                 255 gta gca gca ttg gtt tgg cta gca aag ata aag gct ttt caa att cca    816
Val Ala Ala Leu Val Trp Leu Ala Lys Ile Lys Ala Phe Gln Ile Pro
            260                 265                 270 cat agt gag aat gtg aag ctt ctt ttt gca atg gac ttg agg aga tca    864
His Ser Glu Asn Val Lys Leu Leu Phe Ala Met Asp Leu Arg Arg Ser
        275                 280                 285 ttt aat ccc cct ctt cca cat gga tac tat ggc aat gcc ttt ggt att    912
Phe Asn Pro Pro Leu Pro His Gly Tyr Tyr Gly Asn Ala Phe Gly Ile
    290                 295                 300 gca tgt gca atg gat aat gtc cat gac ctt cta agt gga tct ctt ttg    960
Ala Cys Ala Met Asp Asn Val His Asp Leu Leu Ser Gly Ser Leu Leu
305                 310                 315                 320 cgc act ata atg atc ata aag aaa tca aag ttc tct tta cac aaa gaa   1008
Arg Thr Ile Met Ile Ile Lys Lys Ser Lys Phe Ser Leu His Lys Glu
                325                 330                 335 ctc aac tca aaa acc gtg atg agc tca tct gta gta gat gtc aat acg   1056
Leu Asn Ser Lys Thr Val Met Ser Ser Val Val Asp Val Asn Thr
            340                 345                 350 aag ttt gaa gat gta gtt tca att agt gat tgg agg cat tct ata tat   1104
Lys Phe Glu Asp Val Val Ser Ile Ser Asp Trp Arg His Ser Ile Tyr
        355                 360                 365 tat gaa gtg gac ttt ggg tgg gga gat gca atg aac gtg agc act atg   1152
Tyr Glu Val Asp Phe Gly Trp Gly Asp Ala Met Asn Val Ser Thr Met
    370                 375                 380 cta caa caa cag gag cac gag aaa tct ctg cca act tat ttt tct ttc   1200
Leu Gln Gln Gln Glu His Glu Lys Ser Leu Pro Thr Tyr Phe Ser Phe
385                 390                 395                 400 cta caa tct act aag aac atg cca gat gga atc aag atg cta atg ttt   1248
Leu Gln Ser Thr Lys Asn Met Pro Asp Gly Ile Lys Met Leu Met Phe
                405                 410                 415 atg cct cca tca aaa ctg aaa aaa ttc aaa att gaa ata gaa gct atg   1296
Met Pro Pro Ser Lys Leu Lys Lys Phe Lys Ile Glu Ile Glu Ala Met
            420                 425                 430 ata aaa aaa tat gtg act aaa gtg tgt ccg tcaaagttat ga             1338
Ile Lys Lys Tyr Val Thr Lys Val Cys Pro
        435                 440

<210> SEQ ID NO 37
<211> LENGTH: 442
<212> TYPE: PRT
<213> ORGANISM: Taxus cuspidata

<400> SEQUENCE: 37

Met Lys Lys Thr Gly Ser Phe Ala Glu Phe His Val Asn Met Ile Glu
1               5                   10                  15

Arg Val Met Val Arg Pro Cys Leu Pro Ser Pro Lys Thr Ile Leu Pro
                20                  25                  30

Leu Ser Ala Ile Asp Asn Met Ala Arg Ala Phe Ser Asn Val Leu Leu
            35                  40                  45

Val Tyr Ala Ala Asn Met Asp Arg Val Ser Ala Asp Pro Ala Lys Val
        50                  55                  60
```

```
Ile Arg Glu Ala Leu Ser Lys Val Leu Val Tyr Tyr Pro Phe Ala
65                  70                  75                  80

Gly Arg Leu Arg Asn Lys Glu Asn Gly Glu Leu Glu Val Glu Cys Thr
                85                  90                  95

Gly Gln Gly Val Leu Phe Leu Glu Ala Met Ala Asp Ser Asp Leu Ser
                100                 105                 110

Val Leu Thr Asp Leu Asp Asn Tyr Asn Pro Ser Phe Gln Gln Leu Ile
                115                 120                 125

Phe Ser Leu Pro Gln Asp Thr Asp Ile Glu Asp Leu His Leu Leu Ile
130                 135                 140

Val Gln Val Thr Arg Phe Thr Cys Gly Gly Phe Val Val Gly Ala Asn
145                 150                 155                 160

Val Tyr Gly Ser Ala Cys Asp Ala Lys Gly Phe Gly Gln Phe Leu Gln
                165                 170                 175

Ser Met Ala Glu Met Ala Arg Gly Glu Val Lys Pro Ser Ile Glu Pro
                180                 185                 190

Ile Trp Asn Arg Glu Leu Val Lys Leu Glu His Cys Met Pro Phe Arg
                195                 200                 205

Met Ser His Leu Gln Ile Ile His Ala Pro Val Ile Glu Glu Lys Phe
210                 215                 220

Val Gln Thr Ser Leu Val Ile Asn Phe Glu Ile Ile Asn His Ile Arg
225                 230                 235                 240

Arg Arg Ile Met Glu Glu Arg Lys Glu Ser Leu Ser Ser Phe Glu Ile
                245                 250                 255

Val Ala Ala Leu Val Trp Leu Ala Lys Ile Lys Ala Phe Gln Ile Pro
                260                 265                 270

His Ser Glu Asn Val Lys Leu Leu Phe Ala Met Asp Leu Arg Arg Ser
                275                 280                 285

Phe Asn Pro Pro Leu Pro His Gly Tyr Tyr Gly Asn Ala Phe Gly Ile
290                 295                 300

Ala Cys Ala Met Asp Asn Val His Asp Leu Leu Ser Gly Ser Leu Leu
305                 310                 315                 320

Arg Thr Ile Met Ile Ile Lys Lys Ser Lys Phe Ser Leu His Lys Glu
                325                 330                 335

Leu Asn Ser Lys Thr Val Met Ser Ser Ser Val Val Asp Val Asn Thr
                340                 345                 350

Lys Phe Glu Asp Val Val Ser Ile Ser Asp Trp Arg His Ser Ile Tyr
                355                 360                 365

Tyr Glu Val Asp Phe Gly Trp Gly Asp Ala Met Asn Val Ser Thr Met
                370                 375                 380

Leu Gln Gln Gln Glu His Glu Lys Ser Leu Pro Thr Tyr Phe Ser Phe
385                 390                 395                 400

Leu Gln Ser Thr Lys Asn Met Pro Asp Gly Ile Lys Met Leu Met Phe
                405                 410                 415

Met Pro Pro Ser Lys Leu Lys Lys Phe Lys Ile Glu Ile Glu Ala Met
                420                 425                 430

Ile Lys Lys Tyr Val Thr Lys Val Cys Pro
                435                 440
```

<210> SEQ ID NO 38
<211> LENGTH: 1326
<212> TYPE: DNA
<213> ORGANISM: Taxus canadensis
<220> FEATURE:
<221> NAME/KEY: CDS
<222> LOCATION: (1)..(1326)
<223> OTHER INFORMATION: coding sequence

<400> SEQUENCE: 38

| | | | | | | | | | | | | | | | | |
|---|---|---|---|---|---|---|---|---|---|---|---|---|---|---|---|---|
| atg | gag | aag | gca | ggc | tca | aca | gac | ttc | cat | gta | aag | aaa | ttt | gat | cca | 48 |
| Met | Glu | Lys | Ala | Gly | Ser | Thr | Asp | Phe | His | Val | Lys | Lys | Phe | Asp | Pro | |
| 1 | | | | 5 | | | | | 10 | | | | | 15 | | |
| gtc | atg | gta | gcc | cca | agc | ctt | cca | tcg | ccc | aaa | gct | acc | gtc | cag | ctc | 96 |
| Val | Met | Val | Ala | Pro | Ser | Leu | Pro | Ser | Pro | Lys | Ala | Thr | Val | Gln | Leu | |
| | | | 20 | | | | | 25 | | | | | 30 | | | |
| tct | gtc | gtt | gat | agc | cta | aca | atc | tgc | agg | gga | att | ttt | aac | acg | ttg | 144 |
| Ser | Val | Val | Asp | Ser | Leu | Thr | Ile | Cys | Arg | Gly | Ile | Phe | Asn | Thr | Leu | |
| | | 35 | | | | | 40 | | | | | 45 | | | | |
| ttg | gtt | ttc | aat | gcc | cct | gac | aac | att | tct | gca | gat | cct | gta | aaa | ata | 192 |
| Leu | Val | Phe | Asn | Ala | Pro | Asp | Asn | Ile | Ser | Ala | Asp | Pro | Val | Lys | Ile | |
| 50 | | | | | 55 | | | | | 60 | | | | | | |
| att | aga | gag | gct | ctc | tcc | aag | gtg | ttg | gtg | tat | tat | ttc | cct | ctt | gct | 240 |
| Ile | Arg | Glu | Ala | Leu | Ser | Lys | Val | Leu | Val | Tyr | Tyr | Phe | Pro | Leu | Ala | |
| 65 | | | | 70 | | | | | 75 | | | | | 80 | | |
| ggg | cgg | ctc | aga | agt | aaa | gaa | att | ggg | gaa | ctt | gaa | gtg | gag | tgc | aca | 288 |
| Gly | Arg | Leu | Arg | Ser | Lys | Glu | Ile | Gly | Glu | Leu | Glu | Val | Glu | Cys | Thr | |
| | | | | 85 | | | | | 90 | | | | | 95 | | |
| ggg | gat | ggt | gct | ctg | ttt | gtg | gaa | gcc | atg | gtg | gaa | gac | acc | att | tca | 336 |
| Gly | Asp | Gly | Ala | Leu | Phe | Val | Glu | Ala | Met | Val | Glu | Asp | Thr | Ile | Ser | |
| | | | 100 | | | | | 105 | | | | | 110 | | | |
| gtc | tta | cga | gat | ctg | gat | gac | ctc | aat | cca | tca | ttt | cag | cag | tta | gtt | 384 |
| Val | Leu | Arg | Asp | Leu | Asp | Asp | Leu | Asn | Pro | Ser | Phe | Gln | Gln | Leu | Val | |
| | | 115 | | | | | 120 | | | | | 125 | | | | |
| ttt | tgg | cat | cca | ttg | gac | act | gct | att | gag | gat | ctt | cat | ctt | gtg | att | 432 |
| Phe | Trp | His | Pro | Leu | Asp | Thr | Ala | Ile | Glu | Asp | Leu | His | Leu | Val | Ile | |
| 130 | | | | | 135 | | | | | 140 | | | | | | |
| gtt | cag | gta | aca | cgt | ttt | aca | tgt | ggg | ggc | att | gcc | gtt | gga | gtg | act | 480 |
| Val | Gln | Val | Thr | Arg | Phe | Thr | Cys | Gly | Gly | Ile | Ala | Val | Gly | Val | Thr | |
| 145 | | | | | 150 | | | | | 155 | | | | | 160 | |
| ttg | ccc | cat | agt | gta | tgt | gat | gga | cgt | gga | gca | gcc | cag | ttt | gtt | aca | 528 |
| Leu | Pro | His | Ser | Val | Cys | Asp | Gly | Arg | Gly | Ala | Ala | Gln | Phe | Val | Thr | |
| | | | | 165 | | | | | 170 | | | | | 175 | | |
| gca | ctg | gca | gag | atg | gcg | agg | gga | gag | gtt | aag | ccc | tca | cta | gaa | cca | 576 |
| Ala | Leu | Ala | Glu | Met | Ala | Arg | Gly | Glu | Val | Lys | Pro | Ser | Leu | Glu | Pro | |
| | | | 180 | | | | | 185 | | | | | 190 | | | |
| ata | tgg | aat | aga | gaa | ttg | ttg | aac | cct | gaa | gac | cct | cta | cat | ctc | cag | 624 |
| Ile | Trp | Asn | Arg | Glu | Leu | Leu | Asn | Pro | Glu | Asp | Pro | Leu | His | Leu | Gln | |
| | | 195 | | | | | 200 | | | | | 205 | | | | |
| tta | aat | caa | ttt | gat | tcg | ata | tgc | cca | cct | cca | atg | ctg | gag | gaa | ttg | 672 |
| Leu | Asn | Gln | Phe | Asp | Ser | Ile | Cys | Pro | Pro | Pro | Met | Leu | Glu | Glu | Leu | |
| | 210 | | | | | 215 | | | | | 220 | | | | | |
| ggt | caa | gct | tct | ttt | gtt | ata | aac | gtt | gac | acc | ata | gaa | tat | atg | aag | 720 |
| Gly | Gln | Ala | Ser | Phe | Val | Ile | Asn | Val | Asp | Thr | Ile | Glu | Tyr | Met | Lys | |
| 225 | | | | | 230 | | | | | 235 | | | | | 240 | |
| caa | tgt | gtc | atg | gag | gaa | tgt | aat | gaa | ttt | tgt | tcg | tct | ttt | gaa | gta | 768 |
| Gln | Cys | Val | Met | Glu | Glu | Cys | Asn | Glu | Phe | Cys | Ser | Ser | Phe | Glu | Val | |
| | | | | 245 | | | | | 250 | | | | | 255 | | |
| gtg | gca | gca | ttg | gtt | tgg | ata | gca | cgg | aca | aag | gct | ctt | caa | att | cca | 816 |
| Val | Ala | Ala | Leu | Val | Trp | Ile | Ala | Arg | Thr | Lys | Ala | Leu | Gln | Ile | Pro | |
| | | | 260 | | | | | 265 | | | | | 270 | | | |
| cat | act | gag | aat | gtg | aag | ctt | ctc | ttt | gcg | atg | gat | ttg | agg | aaa | tta | 864 |
| His | Thr | Glu | Asn | Val | Lys | Leu | Leu | Phe | Ala | Met | Asp | Leu | Arg | Lys | Leu | |
| | | 275 | | | | | 280 | | | | | 285 | | | | |
| ttt | aat | ccc | cca | ctt | cca | aat | gga | tat | tat | ggt | aat | gcc | att | ggt | act | 912 |
| Phe | Asn | Pro | Pro | Leu | Pro | Asn | Gly | Tyr | Tyr | Gly | Asn | Ala | Ile | Gly | Thr | |

-continued

```
             290                 295                 300
gca tat gca atg gat aat gtc caa gac ctc tta aat gga tct ctt ttg      960
Ala Tyr Ala Met Asp Asn Val Gln Asp Leu Leu Asn Gly Ser Leu Leu
305                 310                 315                 320 cgt gct ata atg att ata aaa aaa gca aag gct gat tta aaa gat aat     1008
Arg Ala Ile Met Ile Ile Lys Lys Ala Lys Ala Asp Leu Lys Asp Asn
                325                 330                 335 tat tcg agg tca agg gta gtt aca aac cca tat tca tta gat gtg aac     1056
Tyr Ser Arg Ser Arg Val Val Thr Asn Pro Tyr Ser Leu Asp Val Asn
            340                 345                 350 aag aaa tcc gac aac att ctt gca ttg agt gac tgg agg cgg ttg gga     1104
Lys Lys Ser Asp Asn Ile Leu Ala Leu Ser Asp Trp Arg Arg Leu Gly
        355                 360                 365 ttt tat gaa gcc gat ttt ggg tgg gga ggt cca ctg aat gta agt tcc     1152
Phe Tyr Glu Ala Asp Phe Gly Trp Gly Gly Pro Leu Asn Val Ser Ser
    370                 375                 380 ctg caa cgg ttg gaa aat gga ttg cct atg ttt agt act ttt cta tac     1200
Leu Gln Arg Leu Glu Asn Gly Leu Pro Met Phe Ser Thr Phe Leu Tyr
385                 390                 395                 400 cta cta cct gcc aaa aac aag tct gat gga atc aag ctg cta ctg tct     1248
Leu Leu Pro Ala Lys Asn Lys Ser Asp Gly Ile Lys Leu Leu Leu Ser
                405                 410                 415 tgt atg cca cca aca aca ttg aaa tca ttt aaa att gta atg gaa gct     1296
Cys Met Pro Pro Thr Thr Leu Lys Ser Phe Lys Ile Val Met Glu Ala
            420                 425                 430 atg ata gag aaa tat gta agt aaa gtg tga                             1326
Met Ile Glu Lys Tyr Val Ser Lys Val
        435                 440

<210> SEQ ID NO 39
<211> LENGTH: 441
<212> TYPE: PRT
<213> ORGANISM: Taxus canadensis

<400> SEQUENCE: 39

Met Glu Lys Ala Gly Ser Thr Asp Phe His Val Lys Lys Phe Asp Pro
1               5                   10                  15

Val Met Val Ala Pro Ser Leu Pro Ser Pro Lys Ala Thr Val Gln Leu
            20                  25                  30

Ser Val Val Asp Ser Leu Thr Ile Cys Arg Gly Ile Phe Asn Thr Leu
        35                  40                  45

Leu Val Phe Asn Ala Pro Asp Asn Ile Ser Ala Asp Pro Val Lys Ile
    50                  55                  60

Ile Arg Glu Ala Leu Ser Lys Val Leu Val Tyr Tyr Phe Pro Leu Ala
65                  70                  75                  80

Gly Arg Leu Arg Ser Lys Glu Ile Gly Glu Leu Glu Val Glu Cys Thr
                85                  90                  95

Gly Asp Gly Ala Leu Phe Val Glu Ala Met Val Glu Asp Thr Ile Ser
            100                 105                 110

Val Leu Arg Asp Leu Asp Leu Asn Pro Ser Phe Gln Gln Leu Val
        115                 120                 125

Phe Trp His Pro Leu Asp Thr Ala Ile Glu Asp Leu His Leu Val Ile
    130                 135                 140

Val Gln Val Thr Arg Phe Thr Cys Gly Gly Ile Ala Val Gly Val Thr
145                 150                 155                 160

Leu Pro His Ser Val Cys Asp Gly Arg Gly Ala Ala Gln Phe Val Thr
                165                 170                 175
```

```
Ala Leu Ala Glu Met Ala Arg Gly Glu Val Lys Pro Ser Leu Glu Pro
            180                 185                 190

Ile Trp Asn Arg Glu Leu Leu Asn Pro Glu Asp Pro Leu His Leu Gln
        195                 200                 205

Leu Asn Gln Phe Asp Ser Ile Cys Pro Pro Met Leu Glu Glu Leu
    210                 215                 220

Gly Gln Ala Ser Phe Val Ile Asn Val Asp Thr Ile Glu Tyr Met Lys
225                 230                 235                 240

Gln Cys Val Met Glu Glu Cys Asn Glu Phe Cys Ser Ser Phe Glu Val
                245                 250                 255

Val Ala Ala Leu Val Trp Ile Ala Arg Thr Lys Ala Leu Gln Ile Pro
                260                 265                 270

His Thr Glu Asn Val Lys Leu Leu Phe Ala Met Asp Leu Arg Lys Leu
            275                 280                 285

Phe Asn Pro Pro Leu Pro Asn Gly Tyr Tyr Gly Asn Ala Ile Gly Thr
        290                 295                 300

Ala Tyr Ala Met Asp Asn Val Gln Asp Leu Leu Asn Gly Ser Leu Leu
305                 310                 315                 320

Arg Ala Ile Met Ile Ile Lys Lys Ala Lys Ala Asp Leu Lys Asp Asn
                325                 330                 335

Tyr Ser Arg Ser Arg Val Val Thr Asn Pro Tyr Ser Leu Asp Val Asn
            340                 345                 350

Lys Lys Ser Asp Asn Ile Leu Ala Leu Ser Asp Trp Arg Arg Leu Gly
        355                 360                 365

Phe Tyr Glu Ala Asp Phe Gly Trp Gly Pro Leu Asn Val Ser Ser
    370                 375                 380

Leu Gln Arg Leu Glu Asn Gly Leu Pro Met Phe Ser Thr Phe Leu Tyr
385                 390                 395                 400

Leu Leu Pro Ala Lys Asn Lys Ser Asp Gly Ile Lys Leu Leu Leu Ser
                405                 410                 415

Cys Met Pro Pro Thr Thr Leu Lys Ser Phe Lys Ile Val Met Glu Ala
                420                 425                 430

Met Ile Glu Lys Tyr Val Ser Lys Val
            435                 440

<210> SEQ ID NO 40
<211> LENGTH: 1488
<212> TYPE: DNA
<213> ORGANISM: Taxus canadensis
<220> FEATURE:
<221> NAME/KEY: CDS
<222> LOCATION: (1)..(1488)
<223> OTHER INFORMATION: coding sequence

<400> SEQUENCE: 40 atg gac gcc atg gat ctc aca gtt gca aag ttt aag gaa ttc acg cag        48
Met Asp Ala Met Asp Leu Thr Val Ala Lys Phe Lys Glu Phe Thr Gln
1               5                   10                  15 cta cag tcc tct gct att ctt ctc act gtt gtt tct gga atc atc gtc        96
Leu Gln Ser Ser Ala Ile Leu Leu Thr Val Val Ser Gly Ile Ile Val
            20                  25                  30 atc gta atc ctg ctc ctc cgt tct aaa cgc cgc tcc tct ctc aaa ctt       144
Ile Val Ile Leu Leu Leu Arg Ser Lys Arg Arg Ser Ser Leu Lys Leu
        35                  40                  45 cct ccg ggg aaa tta ggc ctc cct ctc att ggg gaa tcg tta tca ttc       192
Pro Pro Gly Lys Leu Gly Leu Pro Leu Ile Gly Glu Ser Leu Ser Phe
    50                  55                  60
```

```
                                                       -continued ctg tgg gct ctt cga tca aac aca ctc gaa cag ttt gtg gac aaa aga     240
Leu Trp Ala Leu Arg Ser Asn Thr Leu Glu Gln Phe Val Asp Lys Arg
 65              70                  75                  80 gtg aag aaa tac ggc aat gtc ttc aag aca tcg tta ctt ggg caa ccc     288
Val Lys Lys Tyr Gly Asn Val Phe Lys Thr Ser Leu Leu Gly Gln Pro
                     85                  90                  95 aca gta gta ctg tgt ggc gca gcc gga aac cgc cta att ctg tcg aac     336
Thr Val Val Leu Cys Gly Ala Ala Gly Asn Arg Leu Ile Leu Ser Asn
                100                 105                 110 cag gag aag ctg ttg agc cga acg gtg tcg gat cga gta gcg aaa ctg     384
Gln Glu Lys Leu Leu Ser Arg Thr Val Ser Asp Arg Val Ala Lys Leu
            115                 120                 125 acg ggt gat act tct att tcg gtt ata gcg gga gac agt cat cgc atc     432
Thr Gly Asp Thr Ser Ile Ser Val Ile Ala Gly Asp Ser His Arg Ile
130                 135                 140 ata cgc gca gca gtt gca ggg ttt ttg ggg cca gca gga ctc aag att     480
Ile Arg Ala Ala Val Ala Gly Phe Leu Gly Pro Ala Gly Leu Lys Ile
145                 150                 155                 160 cac att ggc gaa atg agc gca cat atc cga aat cat atc aac caa gta     528
His Ile Gly Glu Met Ser Ala His Ile Arg Asn His Ile Asn Gln Val
                165                 170                 175 tgg aag gga aaa gat gaa gtg aac gtg ctt agt ttg gca aga gag ctg     576
Trp Lys Gly Lys Asp Glu Val Asn Val Leu Ser Leu Ala Arg Glu Leu
                180                 185                 190 gtc ttc gcc atg tcg gcc agt ttg ttt tta aat ata aat gat aga gag     624
Val Phe Ala Met Ser Ala Ser Leu Phe Leu Asn Ile Asn Asp Arg Glu
            195                 200                 205 gaa cag cac caa ttg cat aag act ctc gaa act att ctt ccc gga tat     672
Glu Gln His Gln Leu His Lys Thr Leu Glu Thr Ile Leu Pro Gly Tyr
        210                 215                 220 ttt tct gtt cct ata aac ttc ccc gga ttt gcc ttt cgc aag gca ctg     720
Phe Ser Val Pro Ile Asn Phe Pro Gly Phe Ala Phe Arg Lys Ala Leu
225                 230                 235                 240 gag gga aac tcg aag cgt agg aaa cat ttc tct gtt tta caa gaa aag     768
Glu Gly Asn Ser Lys Arg Arg Lys His Phe Ser Val Leu Gln Glu Lys
                245                 250                 255 aga aga agg gat ctg agc gta ggg tta gca tcc cgc act cag gat ctg     816
Arg Arg Arg Asp Leu Ser Val Gly Leu Ala Ser Arg Thr Gln Asp Leu
                260                 265                 270 ctt tct gtt ttg ctc gcc tac gaa gat gac aaa ggg aat cca ctc acc     864
Leu Ser Val Leu Leu Ala Tyr Glu Asp Asp Lys Gly Asn Pro Leu Thr
            275                 280                 285 gat gag gag gtc ctc gac aac att tct gcg ctc att gat ggc tcc tac     912
Asp Glu Glu Val Leu Asp Asn Ile Ser Ala Leu Ile Asp Gly Ser Tyr
290                 295                 300 gag agc acc tct tca caa atg gcc atg ctt tta aag ctg ttg tct gac     960
Glu Ser Thr Ser Ser Gln Met Ala Met Leu Leu Lys Leu Leu Ser Asp
305                 310                 315                 320 cat cca gaa tgc tat gaa aaa gta gtt caa gag caa ttg gag ata gct    1008
His Pro Glu Cys Tyr Glu Lys Val Val Gln Glu Gln Leu Glu Ile Ala
                325                 330                 335 tca cat aaa aag gaa gga gaa gaa atc aca tgg aag gat gtg aaa gcc    1056
Ser His Lys Lys Glu Gly Glu Glu Ile Thr Trp Lys Asp Val Lys Ala
                340                 345                 350 atg aga tac aca tgg caa gta atg cag gag acg ctg cgg atg ttt gcc    1104
Met Arg Tyr Thr Trp Gln Val Met Gln Glu Thr Leu Arg Met Phe Ala
            355                 360                 365 cct gtt ttt gga cct cga ggg aaa gct ata act gac att cat tat gac    1152
Pro Val Phe Gly Pro Arg Gly Lys Ala Ile Thr Asp Ile His Tyr Asp
370                 375                 380
```

-continued

```
ggt tac acc att cca aaa gga tgg caa ctt tca tgg gca act tat tca     1200
Gly Tyr Thr Ile Pro Lys Gly Trp Gln Leu Ser Trp Ala Thr Tyr Ser
385                 390                 395                 400 acc cat cag aat gat aca tat ttc aat gag ccg gac aaa ttc atg ccg     1248
Thr His Gln Asn Asp Thr Tyr Phe Asn Glu Pro Asp Lys Phe Met Pro
                405                 410                 415 tcc aga ttc gac gag gaa gga ggg cgt ttg gct cct tac aca ttc gtg     1296
Ser Arg Phe Asp Glu Glu Gly Gly Arg Leu Ala Pro Tyr Thr Phe Val
            420                 425                 430 cca ttt gga gga ggg aga agg aaa tgc cca gga tgg gaa ttc gca aag     1344
Pro Phe Gly Gly Gly Arg Arg Lys Cys Pro Gly Trp Glu Phe Ala Lys
        435                 440                 445 act gag ata tta ctg ttc gtc cat cat ttt gtt aaa aca ttc agt gcc     1392
Thr Glu Ile Leu Leu Phe Val His His Phe Val Lys Thr Phe Ser Ala
    450                 455                 460 tac acc cca atc gat cct cac gaa agt att tgg ggg cgt cca ctc cct     1440
Tyr Thr Pro Ile Asp Pro His Glu Ser Ile Trp Gly Arg Pro Leu Pro
465                 470                 475                 480 cct gtc cct gcc aat gga ttt cct att aaa ctt att tct cga tcc taa    1488
Pro Val Pro Ala Asn Gly Phe Pro Ile Lys Leu Ile Ser Arg Ser
                485                 490                 495

<210> SEQ ID NO 41
<211> LENGTH: 495
<212> TYPE: PRT
<213> ORGANISM: Taxus canadensis

<400> SEQUENCE: 41

Met Asp Ala Met Asp Leu Thr Val Ala Lys Phe Lys Glu Phe Thr Gln
1               5                   10                  15

Leu Gln Ser Ser Ala Ile Leu Leu Thr Val Val Ser Gly Ile Ile Val
                20                  25                  30

Ile Val Ile Leu Leu Leu Arg Ser Lys Arg Arg Ser Ser Leu Lys Leu
            35                  40                  45

Pro Pro Gly Lys Leu Gly Leu Pro Leu Ile Gly Glu Ser Leu Ser Phe
        50                  55                  60

Leu Trp Ala Leu Arg Ser Asn Thr Leu Glu Gln Phe Val Asp Lys Arg
65                  70                  75                  80

Val Lys Lys Tyr Gly Asn Val Phe Lys Thr Ser Leu Leu Gly Gln Pro
                85                  90                  95

Thr Val Val Leu Cys Gly Ala Ala Gly Asn Arg Leu Ile Leu Ser Asn
            100                 105                 110

Gln Glu Lys Leu Leu Ser Arg Thr Val Ser Asp Arg Val Ala Lys Leu
        115                 120                 125

Thr Gly Asp Thr Ser Ile Ser Val Ile Ala Gly Asp Ser His Arg Ile
    130                 135                 140

Ile Arg Ala Ala Val Ala Gly Phe Leu Gly Pro Ala Gly Leu Lys Ile
145                 150                 155                 160

His Ile Gly Glu Met Ser Ala His Ile Arg Asn His Ile Asn Gln Val
                165                 170                 175

Trp Lys Gly Lys Asp Glu Val Asn Val Leu Ser Leu Ala Arg Glu Leu
            180                 185                 190

Val Phe Ala Met Ser Ala Ser Leu Phe Leu Asn Ile Asn Asp Arg Glu
        195                 200                 205

Glu Gln His Gln Leu His Lys Thr Leu Glu Thr Ile Leu Pro Gly Tyr
    210                 215                 220
```

-continued

```
Phe Ser Val Pro Ile Asn Phe Pro Gly Phe Ala Phe Arg Lys Ala Leu
225                 230                 235                 240

Glu Gly Asn Ser Lys Arg Arg Lys His Phe Ser Val Leu Gln Glu Lys
                245                 250                 255

Arg Arg Arg Asp Leu Ser Val Gly Leu Ala Ser Arg Thr Gln Asp Leu
            260                 265                 270

Leu Ser Val Leu Leu Ala Tyr Glu Asp Asp Lys Gly Asn Pro Leu Thr
                275                 280                 285

Asp Glu Glu Val Leu Asp Asn Ile Ser Ala Leu Ile Asp Gly Ser Tyr
    290                 295                 300

Glu Ser Thr Ser Ser Gln Met Ala Met Leu Leu Lys Leu Leu Ser Asp
305                 310                 315                 320

His Pro Glu Cys Tyr Glu Lys Val Val Gln Glu Gln Leu Glu Ile Ala
                325                 330                 335

Ser His Lys Lys Glu Gly Glu Glu Ile Thr Trp Lys Asp Val Lys Ala
                340                 345                 350

Met Arg Tyr Thr Trp Gln Val Met Gln Glu Thr Leu Arg Met Phe Ala
            355                 360                 365

Pro Val Phe Gly Pro Arg Gly Lys Ala Ile Thr Asp Ile His Tyr Asp
    370                 375                 380

Gly Tyr Thr Ile Pro Lys Gly Trp Gln Leu Ser Trp Ala Thr Tyr Ser
385                 390                 395                 400

Thr His Gln Asn Asp Thr Tyr Phe Asn Glu Pro Asp Lys Phe Met Pro
            405                 410                 415

Ser Arg Phe Asp Glu Glu Gly Gly Arg Leu Ala Pro Tyr Thr Phe Val
            420                 425                 430

Pro Phe Gly Gly Gly Arg Arg Lys Cys Pro Gly Trp Glu Phe Ala Lys
        435                 440                 445

Thr Glu Ile Leu Leu Phe Val His His Phe Val Lys Thr Phe Ser Ala
    450                 455                 460

Tyr Thr Pro Ile Asp Pro His Glu Ser Ile Trp Gly Arg Pro Leu Pro
465                 470                 475                 480

Pro Val Pro Ala Asn Gly Phe Pro Ile Lys Leu Ile Ser Arg Ser
                485                 490                 495
```